United States Patent
Holcroft et al.

(10) Patent No.: US 10,239,044 B2
(45) Date of Patent: Mar. 26, 2019

(54) CARBOHYDRATE-MEDIATED PURIFICATION OF PETROCHEMICALS

(71) Applicants: Northwestern University, Evanston, IL (US); King Abdulaziz City for Science and Technology, Riyadh (SA)

(72) Inventors: James M. Holcroft, Evanston, IL (US); Karel J. Hartlieb, Evanston, IL (US); James Fraser Stoddart, Evanston, IL (US)

(73) Assignees: Northwestern University, Evanston, IL (US); King Abdulaziz City for Science and Technology (KACST), Riyadh (SA)

( * ) Notice: Subject to any disclaimer, the term of this patent is extended or adjusted under 35 U.S.C. 154(b) by 0 days.

(21) Appl. No.: 15/316,393

(22) PCT Filed: Jun. 8, 2015

(86) PCT No.: PCT/US2015/034754
§ 371 (c)(1),
(2) Date: Dec. 6, 2016

(87) PCT Pub. No.: WO2015/188199
PCT Pub. Date: Dec. 10, 2015

(65) Prior Publication Data
US 2017/0189890 A1    Jul. 6, 2017

Related U.S. Application Data

(60) Provisional application No. 62/008,671, filed on Jun. 6, 2014.

(51) Int. Cl.
*C07C 7/12* (2006.01)
*B01J 20/22* (2006.01)
(Continued)

(52) U.S. Cl.
CPC ....... *B01J 20/226* (2013.01); *B01J 20/28004* (2013.01); *B01J 20/305* (2013.01);
(Continued)

(58) Field of Classification Search
CPC ..... B01J 20/226; B01J 20/28004; C07C 7/12; C07C 17/389
(Continued)

(56) References Cited

U.S. PATENT DOCUMENTS 2,985,589 A   5/1961   Broughton et al.
3,959,978 A   6/1976   Lindley et al.
(Continued)

FOREIGN PATENT DOCUMENTS

EP   2588433       1/2012
WO   2011116222    9/2011
(Continued)

OTHER PUBLICATIONS

Alaerts, L. et. al. "Activation of the metal-organic framework MIL-47 for selective adsorption of xylenes and other difunctionalized aromatics", Phys. Chem. Chem. Phys. (2008), 10, pp. 2979-2985.*

(Continued)

*Primary Examiner* — Philip Y Louie
*Assistant Examiner* — Aaron W Pierpont
(74) *Attorney, Agent, or Firm* — Andrus Intellectual Property Law, LLP

(57) ABSTRACT

A separation medium consisting of a cyclodextrin metalorganic framework (CD-MOF) for separating aromatic compounds and methods of preparing the same are presented. Bottom-up preparations include the following steps: (a) preparing a first mixture comprising a cyclodextrin, an alkali metal salt, water and an alcohol; (b) performing one of the following two steps: (i) stirring the first mixture; or (ii)
(Continued)

adding an amount of a surfactant to the first mixture to form a second mixture; and (c) crystallizing the CD-MOF from the first mixture or the second mixture. Top-down preparations include the following steps: (a) preparing a first mixture comprising the cyclodextrin, an alkali metal salt, water and an alcohol; (b) crystallizing the CD-MOF from the first mixture; and (c) optionally performing particle size reduction of the crystallized CD-MOF. The CD-MOFs are amenable for use in methods for separating alkylaromatic and haloaromatic compounds from a mixture of hydrocarbons.

13 Claims, 60 Drawing Sheets
(41 of 60 Drawing Sheet(s) Filed in Color)

(51) Int. Cl.
| | | |
|---|---|---|
| B01J 20/30 | (2006.01) | |
| C07C 7/13 | (2006.01) | |
| C07C 17/38 | (2006.01) | |
| B01J 20/28 | (2006.01) | |
| C07C 17/389 | (2006.01) | |

(52) U.S. Cl.
CPC ....... *B01J 20/3021* (2013.01); *B01J 20/3085* (2013.01); *C07C 7/12* (2013.01); *C07C 7/13* (2013.01); *C07C 17/38* (2013.01); *C07C 17/389* (2013.01); *C07C 2601/16* (2017.05); *C07C 2602/42* (2017.05); *Y02P 20/582* (2015.11)

(58) Field of Classification Search
USPC .................................. 585/804, 820, 830, 831
See application file for complete search history.

(56) References Cited

U.S. PATENT DOCUMENTS

| | | | |
|---|---|---|---|
| 5,498,822 | A | 3/1996 | Eccli et al. |
| 5,811,629 | A | 9/1998 | Hubbell et al. |
| 2012/0004491 | A1 | 1/2012 | Kulprathipanja et al. |
| 2012/0070904 | A1* | 3/2012 | Stoddart ................ B01J 20/226 436/133 |
| 2014/0061540 | A1 | 3/2014 | Long et al. |

FOREIGN PATENT DOCUMENTS

| | | |
|---|---|---|
| WO | 2011116222 A2 | 9/2011 |
| WO | 2012012125 | 1/2012 |
| WO | 2013011210 | 1/2013 |
| WO | 2013118011 | 8/2013 |

OTHER PUBLICATIONS

Zhao, W. et. al. "Adsorption Properties of β Cyclodextrin for adsorbing Aromatic Hydrocarbons from the Gas Phase and Water", Journal of Marcromolecular Science, Part B., (Jan. 3, 2008), Abstract.*
Chen, W. et. al. "Calculations of Cyclodextrin Binding Affinities: Energy, Entropy, and Implications for Drug Design", Biophysical Journal (2004), 87, pp. 3035-3049.*
Andronikashvili, T. G. et. al. "Gas Chromatographic Separation of Isomeric Benzene Derivatives Using Molecular Sieves, Combined with Partition Columns", Chromatographia (1994), 38, pp. 613-616.*
International Search Report for PCT/US2015/034754 dated Sep. 28, 2015, four pages.
Written Opinion of the International Searching Authority for PCT/US2015/034754 dated Sep. 28, 2015, eight pages.
Smaldone et al., "Metal-Organic Frameworks from Edible Natural Products," Ang. Chem. Int. Ed. 49(46):8630-8634 (2010).
Alaerts, L.; Kirschhock, C. E. A.; Maes, M; van der Veen, M. A.; Finsy, V.; Depla, A.; Martens, J. A.; Baron, G. V.; Jacobs, P. A.; Denayer, J. F. M.; De Vos, D. E. Angew. Chem., Int. Ed. 2007, 46, 4293.
Alaerts, L.; Maes, M.; Giebeler, L.; Jacobs, P. A.; Martens, J. A.; Denayer, J. F. M.; Kirschhock, C. E. A.; De Vos, D. E. J. Am. Chem. Soc. 2008, 130, 14170.
Alaerts, L.; Maes, M.; Jacobs, P. A.; Denayer, J. F. M.; De Vos, D. E. Phys. Chem. Chem. Phys. 2008, 10, 2979.
Al-Maythalony, B. A.; Shekhah, O.; Swaiden, R.; Belmabkhout, Y.; Pinnau, I.; Eddaoudi, M. J. Am. Chem. Soc. 2015, 137, 1754.
Bell, J. G.; Zhao, X.; Uygur, Y.; Thomas, K. M. J. Phys. Chem. C 2011, 115, 2776.
Bender. M. L.; Komiyama, M. Cyclodextrin Chemistry; Springer-Verlag: New York, 1978.
Bemini, M. C.; Jimenez, D. F.; Pasinetti, M.; Ramirez-Pastor, A. J.; Snurr, R. Q. J. Mater. Chem. B 2014, 2, 766.
Beyzavi, M. H.; Klet, R. C.; Tussupbayev, S.; Borycz, J.; Vermeulen, N. A.; Cramer, C. J.; Stoddart, J. F.; Hupp, J. T.; Farha, O. K. J. Am. Chem. Soc. 2014, 136, 15861.
Bloch, E. D.; Queen, W. L.; Krishna, R.; Zadrozny, J. M.; Brown, C. M.; Long, J. R. Science 2012, 335, 1606.
Bordewijk, P., Chem. Phys. Lett., 1975, 32, 592.
Bradshaw, D.; Prior, T. J.; Cussen, E. J.; Claridge, J. B.; Rosseinsky, M. J. J. Am. Chem. Soc. 2004, 126, 6106.
Chen, B.; Zhao, X.; Putkham, A.; Hong, K.; Lobkovsky, E. B.; Hurtado, E. J.; Fletcher, A. J.; Thomas, K. M., J. Am. Chem. Soc., 2008, 130, 6411.
Chen, Y.; Liu, Y. Chem. Soc. Rev. 2010, 39, 495.
Cole, J. H.; Everett, D. H.; Marshall, C. T.; Paniego, A. R.; Powl, J. C.; Rodriguez-Reinoso, F. J. Chem. Soc., Faraday Trans. 1974, 70, 2154.
Cottier, V.; Bellat, J.-P.; Simonot-Grange, M.-H.; Methivier,A.J. Phys.Chem.B 1997,101,4798.
Crank, J. The mathematics of diffusion, 2nd ed.; Clarendon Press: Oxford, 1975.
Das, M. C.; Guo, Q.; He, Y.; Kim, J.; Zhao, C.-G.; Hong, K.; Xiang, S.; Zhang, Z.; Thomas, K. M.; Krishna, R.; Chen, B. J. Am. Chem. Soc. 2012, 134, 8703.
Demessence, A.; D'Alessandro, D. M.; Foo, M. L.; Long, J. R. J. Am. Chem. Soc. 2009, 131, 8784.
Dinca, M.; Yu, A. F.; Long, J. R. J. Am. Chem. Soc. 2006, 128, 8904.
Douhal, A. Chem. Rev. 2004, 104, 1955.
Dufner, H.; Kast, S. M.; Brickmann, J.; Schlenkrich, M. J. Comput. Chem., 1997, 18, 660.
Eddaoudi, M.; Kim, J.; Rosi, N.; Vodak, D.; Wachter, J.; O'Keeffe, M.; Yaghi, O. M. Science 2002, 295, 469.
Eddaoudi, M.; Moler, D. B.; Li, H.; Chen, B.; Reineke, T. M.; O'Keeffe, M.; Yaghi, O. M. Acc. Chem. Res. 2001, 34, 319.
El Osta, R., et al., Chem. Mater. 2012, 24, 2781.
Farha, O. K.; Eryazici, I.; Jeong, N. C.; Hauser, B. G.; Wilmer, C. E.; Sarjeant, A. A.; Snurr, R. Q.; Nguyen, S. T.; Yazaydin, A. Ö.; Hupp, J. T. J. Am. Chem. Soc. 2012, 134, 15016.
Fei, H.; Cohen, S. M. J. Am. Chem. Soc. 2015, 137, 2191.
Ferey, G. Chem. Soc. Rev. 2008, 37, 191.
Ferey, G.; Serre, C. Chem. Soc. Rev. 2009, 38, 1380.
Fletcher, A. J.; Cussen, E. J.; Bradshaw, D.; Rosseinsky, M. J.; Thomas, K. M., J. Am. Chem. Soc., 2004, 126, 9750.
Fletcher, A. J.; Thomas, K. M., J. Phys. Chem. C, 2007, 111, 2107.
Fletcher, A. J.; Yuzak, Y.; Thomas, K. M., Carbon, 2006, 44, 989.
Fletcher, A.J. et al., J. Am. Chem. Soc. 2001, 123, 10001.
Forgan, R. S.; Smaldone, R. A.; Gassensmith, J. J.; Furukawa, H.; Cordes, D. B.; Li, Q.; Wilmer, C. E.; Botros, Y. Y.; Snurr, R. Q.; Slawin, A. M. Z.; Stoddart, J. F. J. Am. Chem. Soc. 2011, 134, 406.
Forster, T., Z. Naturforsch. Teil A, 1949, 4, 321.
Fracaroli, A. M.; Furukawa, H.;Suzuki,M.; Dodd,M.; Okajima,S.; Gańdara,F.; Reimer,J.A.; Yaghi, O. M. J. Am. Chem. Soc. 2014, 136, 8863.
Fujita, M.; Kwon, Y. J.; Washizu, S.; Ogura, K. J. Am. Chem. Soc. 1994, 116, 1151.

(56) References Cited

OTHER PUBLICATIONS

Furukawa, H.; Mueller, U.; Yaghi, O. M. Angew. Chem., Int. Ed. 2015, 54, 3417.
Furukawa, Y.; Ishiwata, T.; Sugikawa, K.; Kokado, K.; Sada, K. Angew. Chem. Int. Ed. 2012, 51, 10566.
Glarum, S. H., J. Chem. Phys., 1960, 33, 1371.
Glueckauf, E. Trans. Faraday Soc. 1955, 51, 1540.
Glueckauf, E.; Coates, J. I. J. Chem. Soc. 1947, 1315.
Goeppert, A.; Czaun, M.; Surya Prakash, G. K.; Olah, G. A. Energy Environ. Sci. 2012, 5, 7833.
Gupta, A., et al., Mol. Simul. 2003, 29, 29.
Han, S.; Wei, Y.; Valente, C.; Forgan, R. S.; Gassensmith, J. J.; Smaldone, R. A.; Nakanishi, H.; Coskun, A.; Stoddart, J. F.; Grzybowski, B. A. Angew. Chem, Int. Ed. 2011, 50, 276.
Harada, A.; Kobayashi, R.; Takashima, Y.; Hashidzume, A.; Yamaguchi, H. Nat. Chem. 2011, 3, 34.
Harada, A.; Li, J.; Kamachi, M. Macromolecules 1993, 26, 5267.
Harada, A.; Li, J.; Kamachi, M. Nature 1994, 370, 126.
Harada, A.; Takashima, Y. Chem. Res. 2013, 13, 420.
Harada, A.; Takashima, Y.; Nakahata, M. Acc. Chem. Res. 2014, 47, 2128.
Harada, A.; Takashima, Y.; Yamaguchi, H. Chem. Soc. Rev. 2009, 38, 875.
Hayashi, H.; Cote, A. P.; Furukawa, H.; O'Keeffe, M.; Yaghi, O. M. Nat. Mater. 2007, 6, 501.
He, Y.; Zhang, Z.; Xiang, S.; Fronczek, F. R.; Krishna, R.; Chen, B. Chem. Commun. 2012, 48, 6493.
Herm, Z. R.; Wiers, B. M.; Mason, J. A.; van Baten, J. M; Hudson, M. R.; Zajdel, P.; Brown, C. M.; Masciocchi, N.; Krishna, R.; Long, J. R. Science 2013, 340, 960.
Holcroft, J.M. et al. "Carbohydrate-Mediated Purification of Petrochemicals," J. Am. Chem. Soc. 2015, 137:5706-5719 (including Supporting Information).
Hoskins, B. F.; Robson, R. J. Am. Chem. Soc. 1989, 111, 5962.
Hoskins, B. F.; Robson, R. J. Am. Chem. Soc. 1990, 112, 1546.
Hu, J.; Sun, T.; Ren, X.; Wang, S. Microporous Mesoporous Mater. 2015, 204, 73.
Hulme, R.; Rosensweig, R. E.; Ruthven, D. M. Ind. Eng. Chem. Res. 1991, 30, 752.
Ikeda, H.; Nihei, T.; Ueno, A. J. Org. Chem. 2005, 70, 1237.
Jee, S. E.; Sholl, D. S. J. Am. Chem. Soc. 2009, 131, 7896.
Jiang, H.-L.; Xu, Q. Chem. Commun. 2011, 47, 3351.
Jorgensen, W. L.; Nguyen, T. B. J. Comput. Chem., 1993, 14, 195.
Ke, C.; Yang, C.; Mori, T.; Wada, T.; Liu, Y.; Inoue, Y. Angew. Chem., Int. Ed. 2009, 48, 6675.
Keskin, S.; Kizilel, S. Ind. Eng. Chem. Res. 2011, 50, 1799.
Keskin, S.; Sholl, D. S. J. Phys. Chem. C 2007, 111, 14055.
Kitagawa, S.; Kitaura, R.; Noro, S.-i. Angew. Chem., Int. Ed. 2004, 43, 2334.
Klafter, J.; Shlesinger, M. F., Proc. Natl. Acad. Sci. U. S. A., 1986, 83, 848.
Kuang, X.; Ma, Y.; Su, H.; Zhang, J.; Dong, Y.-B.; Tang, B. Anal. Chem. 2013, 86, 1277.
Kulprathipanja, S. J.; James, R. B. Zeolites in Industrial Separation; Wiley-VCH: Weinheim, 2010.
Latroche, M.; Surble, S.; Serre, C.; Mellot-Draznieks, C.; Llewellyn, P.L.;Lee, J.-H.;Chang,J.-S.;Jhung,S.H.;Fefey,G. Angew. Chem, Int. Ed. 2006, 45, 8227.
Lee, C. Y.; Bae, Y.-S.; Jeong, N. C.; Farha, O. K.; Sarjeant, A. A.; Stern, C. L.; Nickias, P.; Snurr, R. Q.; Hupp, J. T.; Nguyen, S. T. J. Am. Chem. Soc. 2011, 133, 5228.
LeVan, M.D., Adsorption Science and Technology, NATO ASI Series E Applied Science; A.E. Rodriguez, LeVan, M.D., Eds.; Kluwer: Dordrecht, 1989, 158, 149.
Li, B.; Wen, H.-M.; Wang, H.; Wu, H.; Tyagi, M.; Yildirim, T.; Zhou, W.; Chen, B. J. Am. Chem. Soc. 2014, 136, 6207.
Li, G.; McGown, L. B. Science 1994, 264, 249.
Li, H.; Eddaoudi, M.; O'Keeffe, M.;Yaghi, O. M. Nature 1999, 402, 276.
Li, J.-R.; Kuppler, R. J.; Zhou, H.-C. Chem. Soc. Rev. 2009, 38, 1477.
Li, L. J.; Bell, J. G.; Tang, S. F.; Lv, X. X.; Wang, C.; Xing, Y. L.; Zhao, X. B.; Thomas, K. M. Chem. Mater. 2014, 26, 4679.
Lima, R. M.; Grossmann, I. E. AIChE J. 2009, 55, 354.
Liu, Y.; Eubank, J. F.; Cairns, A. J.; Eckert, J.; Kravtsov, V. C.; Luebke, R.; Eddaoudi, M. Angew. Chem., Int. Ed. 2007, 46, 3278.
Liu, Y.; Xuan, W.; Cui, Y. Adv. Mater. 2010, 22, 4112.
Loughlin, K. F.; Hassan, M. M.; Fatehi, A. I.; Zahur, M. Gas Sep. Purif. 1993, 7, 264.
Lucena, S. M. P.; Snurr, R. Q.; Cavalcante, C. L., Jr. Adsorption 2007, 13, 477.
Luebbers, M. T.; Wu, T.; Shen, L.; Masel, R. I. Langmuir 2010, 26, 11319.
Lusi, M.; Barbour, L. J. Angew. Chem., Int. Ed. 2012, 51, 3928.
Ma, X.; Tian, H. Acc. Chem. Res. 2014, 47, 1971.
Maes, M.; Alaerts, L.; Vermoortele, F.; Ameloot, R.; Couck, S.; Finsy, V.; Denayer, J. F. M.; De Vos, D. E. J. Am. Chem. Soc. 2010, 132, 2284.
Maes, M.; Vermoortele, F.; Boulhout, M.; Boudewijns, T.; Kirschhock, C.; Ameloot, R.; Beurroies, I.; Denoyel, R.; De Vos, D. E. Microporous Mesoporous Mater. 2012, 157, 82.
Matsuda, R.; Kitaura, R.; Kitagawa, S.; Kubota, Y.; Belosludov, R. V.; Kobayashi, T. C.; Sakamoto, H.; Chiba, T.; Takata, M.; Kawazoe, Y.; Mita, Y. Nature 2005, 436, 238.
Minceva, M.; Rodrigues, A. E. AIChE J. 2007, 53, 138.
Minceva, M.; Rodrigues, A. E. Chem. Eng. Res. Des. 2004, 82, 667.
Mitra, T.; Jelfs, K. E.; Schmidtmann, M.; Ahmed, A.; Chong, S. Y.; Adams, D. J.; Cooper, A. I. Nat. Chem. 2013, 5, 276.
Moulton, B.; Zaworotko, M. J. Chem. Rev. 2001, 101, 1629.
Mueller, U.; Schubert, M.; Teich, F.; Puetter, H.; Schierle-Arndt, K.; Pastre, J. J. Mater. Chem. 2006, 16, 626.
Munch, A. S.; Mertens, F. O. R. L. J. Mater. Chem. 2012, 22, 10228.
Murray, L. J.; Dinca, M.; Long, J. R. Chem. Soc. Rev. 2009, 38, 1294.
Nakahata, M.; Takashima, Y.; Yamaguchi, H.; Harada, A. Nat. Commun. 2011, 2, 511.
Nalluri, S. K. M.; Voskuhl, J.; Bultema, J. B.; Boekema, E. J.; Ravoo, B. J. Angew. Chem., Int. Ed. 2011, 50, 9747.
Nuzhdin, A. L.; Dybtsev, D. N.; Bryliakov, K. P.; Talsi, E. P.; Fedin, V. P. J. Am. Chem. Soc. 2007, 129, 12958.
O'Keeffe, M. Chem. Soc. Rev. 2009, 38, 1215.
Padmanaban, M.; Muller, P.; Lieder, C.; Gedrich, K.; Grunker, R.; Bon, V.; Senkovska, I.; Baumgartner, S.; Opelt, S.; Paasch, S.; Brunner, E.; Glorius, F.; Klemm, E.; Kaskel, S. Chem. Commun. 2011, 47, 12089.
Palmer, R. G.; Stein, D. L.; Abrahams, E.; Anderson, P. W., Phys. Rev. Lett., 1984, 53, 958.
Rappe, A. K.; et al., J. Am. Chem. Soc., 1992 114, 10024.
Reid, C. R.; Thomas, K. M. J. Phys. Chem. B 2001, 105, 10619.
Rekharsky, M. V.; Inoue, Y. Chem. Rev. 1998, 98, 1875.
Remy, T.; Ma, L.; Maes, M.; De Vos, D. E.; Baron, G. V.; Denayer, J. F. M. Ind. Eng. Chem. Res. 2012, 51, 14824.
Sallas, F.; Darcy, R. Eur. J. Org. Chem. 2008, 957.
Sarkisov, L. Phys. Chem. Chem. Phys. 2012, 14, 15438.
Sato, H.; Kosaka, W.; Matsuda, R.; Hori, A.; Hijikata, Y.; Belosludov, R. V.; Sakaki, S.; Takata, M.; Kitagawa, S. Science 2014, 343, 167.
Schmidt, B. V. K. J.; Hetzer, M.; Ritter, H.; Bamer-Kowollik, C. Prog. Polym. Sci. 2014, 39, 235.
Schneider, H.-J. Angew. Chem., Int. Ed. 2009, 48, 3924.
Shlesinger, M. F.; Montroll, E. W. Proceedings of the National Academy of Sciences of the United States of America—Physical Sciences, 1984, 81, 1280.
Takei, M.; Yui, H.; Hirose, Y.; Sawada, T. J. Phys. Chem. A 2001, 105, 11395.
Tamaki, T.; Kokubu, T. J. Incl. Phenom. Macrocycl. Chem. 1984, 2, 815.
Torres-Knoop, A.; Krishna, R.; Dubbeldam, D. Angew. Chem., Int. Ed. 2014, 53, 7774.
Tozawa, T.; Jones, J. T. A.; Swamy, S. I.; Jiang, S.; Adams, D. J.; Shakespeare, S.; Clowes, R.; Bradshaw, D.; Hasell, T.; Chong, S. Y.; Tang, C.; Thompson, S.; Parker, J.; Trewin, A.; Bacsa, J.; Slawin, A. M. Z.; Steiner, A.; Cooper, A. I. Nat. Mater. 2009, 8, 973.

(56) References Cited

OTHER PUBLICATIONS

Vaidhyana- than, R.; Bradshaw, D.; Rebilly, J.-N.; Barrio, J. P.; Gould, J. A.; Berry, N. G.; Rosseinsky, M. J. Angew. Chem., Int. Ed. 2006, 118, 6645.
Vajda, S.; Jimenez, R.; Rosenthal, S. J.; Fidler, V.; Fleming, G. R.; Castner, E. W. J. Chem. Soc., Faraday Trans. 1995, 91, 867.
Van de Manakker, F.; Vermonden, T.; van Nostrum, C. F.; Hennink, W. E. Biomacromolecules 2009, 10, 3157.
Vermoortele, F.; Maes, M.; Moghadam, P. Z.; Lennox, M. J.; Ragon, F.; Boulhout, M.; Biswas, S.; Laurier, K. G. M.; Beurroies, I.; Denoyel, R.; Roeffaers, M.; Stock, N.; Düren, T.; Serre, C.; De Vos, D. E. J. Am. Chem. Soc. 2011, 133, 18526.
Wang, C.; Li, L.; Bell, J. G.; Lv, X. X.; Tang, S.; Zhao, X. B.; Thomas, K. M. Chem. Mater. 2015, 27, 1502.
Wang, H. M.; Wenz, G. Beilstein J. Org. Chem. 2012, 8, 1644.
Wang, H. M.; Wenz, G. Chem. Asian J. 2011, 6, 2390.
Wang, H.; Cao, D. J. Phys. Chem. C 2015, 119, 6324.
Wang, W.; Dong, X.; Nan, J.; Jin, W.; Hu, Z.; Chen, Y.; Jiang, J. Chem. Commun. 2012, 48, 7022.
Warren, J. E.; Perkins, C. G.; Jelfs, K. E.; Boldrin, P.; Chater, P. A.; Miller, G. J.; Manning, T. D.; Briggs, M. E.; Stylianou, K. C.; Claridge, J. B.; Rosseinsky, M. J. Angew. Chem., Int. Ed. 2014, 126, 4680.
Webster, C. E.; Drago, R. S.; Zerner, M. C. J. Am. Chem. Soc. 1998, 120, 5509.
Wei, Y.; Han, S.; Walker, D. A.; Fuller, P. E.; Grzybowski, B. A. Angew. Chem., Int. Ed. 2012, 51, 7435.
Wenz, G. Angew. Chem., Int. Ed. Engl. 1994, 33, 803.
Wenz, G.; Han, B.-H.; Müller, A. Chem. Rev. 2006, 106, 782.
Wilmer, C. E.; Kim, K. C.; Snurr, R. Q. J. Phys. Chem. Lett., 2012, 3, 2506.
Yang, C.; Inoue, Y. Chem. Soc. Rev. 2014, 43, 4123.
Yang, S.; Lin, X.; Lewis, W.; Suyetin, M.; Bichoutskaia, E.; Parker, J. E.; Tang, C. C.; Allan, D. R.; Rizkallah, P. J.; Hubberstey, P.; Champness, N. R.; Mark Thomas, K.; Blake, A. J.; Schröder, M. Nat. Mater. 2012, 11, 710.
Yoon, S. M.; Warren, S. C.; Grzybowski, B. A. Angew. Chem., Int. Ed. 2014, 53, 4437.
Zhao, X.; Bu, X.; Zhai, Q. C.; Tran, H.; Feng, P. J. Am. Chem. Soc. 2015, 137, 1396.
Zhao, X.; Villar-Rodil, S.; Fletcher, A. J.; Thomas, K. M., J. Phys. Chem. B, 2006, 110, 9947.
Zheng, B.; Bai, J.; Duan, J.; Wojtas, L.; Zaworotko, M. J. J. Am. Chem. Soc. 2010, 133, 748.
Jiang, J.; Sandler, S. I. Langmuir 2006, 22, 5702.
Farrusseng, D. et al. Langmuir 2009, 25, 7383.
Trung, T. K. et al. J. Am. Chem. Soc. 2008, 130, 16926.
Couck, S.; et al. Phys. Chem. Chem. Phys. 2010, 12, 9413.
Fairen-Jimenez, D. et al. Dalton Trans. 2012, 41, 10752.
Ma, S. et al. Angew. Chem., Int. Ed. 2007, 46, 2458.
Pan, L. et al. Angew. Chem., Int. Ed. 2006, 45, 616.
Finsy, V. et al. Phys. Chem. Chem. Phys. 2009, 11, 3515.
Trung, T. K. et al. Microporous Mesoporous Mater. 2010, 134, 134.
Ramsahye, N. A. et al. Chem. Mater. 2013, 25, 479.
Lee, J. Y. et al Adv. Funct. Mater. 2007, 17, 1255.
Herm, Z. R. et al. Science 2013, 340, 960.
Dubbeldam, D. et al. J. Am. Chem. Soc. 2008, 130, 10884.
Barcia, P. S. et al. Phys. Chem. B 2007, 111, 6101.
Plaza, M. G. et al. Microporous Mesoporous Mater. 2012, 157, 101.
Mika, T. et al. Nat. Chem. 2013, 5, 276.
Chermisinoff, P.N. et al Carbon Adsorption Handbook; Ann Arbor Science Publishers: Ann Arbor, MI, 1978.
Gassensmith et al. Jour. Amer. Chem. Soc. 2014, 136, 8277-8282.
Snyder et al. Practical HPLC method development Second Edition, John Wiley & Sons, Inc., 1997.
Mattson et al. Activated Carbon; Marcel Dekker: New York, 1971.
Kirk-Othmer Separation Technology, 2nd ed.; Wiley: Hoboken, NJ, 2008; two-volume set; vol. 1.

* cited by examiner

US 10,239,044 B2

CARBOHYDRATE-MEDIATED PURIFICATION OF PETROCHEMICALS

CROSS-REFERENCE TO RELATED APPLICATIONS

The present application is the U.S. National Stage of International Patent Application No. PCT/US2015/034754, filed Jun. 8, 2015, which claims benefit of priority under 35 U.S.C. 119 to U.S. provisional patent application Ser. No. 62/008,671, filed Jun. 6, 2014, and entitled "CARBOHYDRATE-MEDIATED PURIFICATION OF PETROCHEMICALS," the contents of which are herein incorporated by reference in its entirety.

BACKGROUND

1. Technical Field

The present disclosure relates to carbohydrates for the purification of petrochemical compounds.

2. Description of Related Art

With the expanding global demand for petrochemical feed-stocks, the development of novel, low-cost materials that reduce the impact of chemical processing on the environment is critically important. Improving the efficiency of the refinement and separation of aromatic hydrocarbons is of particular importance, given the large volumes on which these compounds are produced. The sustained interest in metal-organic frameworks[1] (MOFs) as adsorbents and sequestering agents for industrially important gases,[2-4] e.g., $H_2$, $CH_4$, $CO_2$ and $N_2$, as well as for the liquid-phase separation of larger molecular compounds, which include (1) constitutional isomers,[5] (2) chiral compounds,[6] (3) aliphatic hydro-carbons,[3b,5b,7] and (4) pharmaceuticals,[8] is leading to MOFs being investigated as alternatives to zeolites[9] and activated carbon[10] as separation media. The improvements[5-7] in separation efficiencies using MOFs over traditional size- and shape-selective materials can be attributed primarily to (i) the physiochemical properties imbedded in their diverse building blocks, (ii) their higher surface areas, and (iii) their larger adsorption capacities, which reduce the amount of adsorbent required for industrial processes.[7a,11] Consequently, MOFs represent emergent materials for separation technologies in many different industrial settings.

In the chemical industry, one of the most challenging separations is that of BTEX (that is, benzene, toluene, ethylbenzene, and the three regioisomers of xylene) obtained from the refining of crude oil. The xylene isomers, together with ethylbenzene, constitute the $C_8$ aromatics that are derived[12] from crude oil by catalytic reforming, toluene disproportionation, and the distillation of pyrolysis gasoline. These $C_8$ aromatics not only act[12b] as octane and antiknocking additives in gasoline, but they are also important chemical feedstocks, thus bringing about the necessity for their processing and separation. The difficulty in separating p-xylene from the BTEX mixture can be ascribed to the similar physical properties of these $C_8$ aromatics. Industrial practices[12,13] focus on separation by adsorption strategies or crystallization procedures, with 60% of p-xylene produced today relying on simulated moving bed (SMB) technologies.[12,13] Here, $C_8$ aromatics are separated based on differences in adsorbate-adsorbent interactions within faujasite-type zeolites. The xylene adsorption equilibrium can be tuned by ion-exchange within the zeolite to attain[9a,12a,14] p-xylene purities of approximately 95 wt % per pass. Crystallization techniques account for the purification of the remaining 40% of p-xylene produced.[13b, c,15]

These energy-intensive processes highlight the need for further improvements in the technologies currently available, especially in relation to materials that can discriminate among BTEX molecules. A wide variety of materials have been investigated for the separation of aromatic hydrocarbons, such as zeolites,[9,12a] discrete metal complexes,[16] and organic cages.[17] MOFs have exhibited varying degrees of success in separating xylenes from mixtures of $C_8$ aromatics, e.g., classical rigid MOFs, such as copper benzenetricarboxylate [$Cu_3(btc)_2$], have been employed to separate BTEX mixtures chromotographically,[18] while MOF-5 shows little to no separation of the xylene isomers.[19] The most widely investigated MOFs for separating aromatic hydro-carbons are the terephthalate-based structures with one-dimensional channels,[20-24] namely MIL-47 and MIL-53. Both MOFs exhibit high o-xylene selectivity, separating the xylene regioisomers based on molecular packing and entropic differences.[21-23,25] More recently,[26,27] MIL-125 and MAF-X8 have exhibited high p-xylene affinity due to pore morphology and commensurate stacking, respectively. The guest-driven restructuring of a flexible cerium tetradentate carboxylate MOF led to high selectivity by restructuring of the framework around p- and m-xylene, displaying molecular-level recognition,[28] and adding to the growing number of flexible MOFs having potential utility for separations.[6h, 21,28]

BRIEF SUMMARY

In a first aspect, a method of preparing a separation medium consisting of a cyclodextrin metal-organic framework (CD-MOF) is provided. The method includes several steps. The first step includes preparing a first mixture comprising a cyclodextrin, an alkali metal salt, water and an alcohol. The second step includes performing one of the following two steps: stirring the first mixture; or adding an amount of a surfactant to the first mixture to form a second mixture. The third step includes crystallizing the CD-MOF from the first mixture or the second mixture.

In a second aspect, a method of preparing a separation medium consisting of a cyclodextrin metal-organic framework (CD-MOF) is provided. The method includes several steps. The step includes preparing a first mixture comprising the cyclodextrin, an alkali metal salt, water and an alcohol. The second step includes crystallizing the CD-MOF from the first mixture. A third step includes optionally performing particle size reduction of the crystallized CD-MOF.

In a third aspect, a separation medium consisting of a γ-cyclodextrin metal-organic framework (CD-MOF) is provided. The separation medium is prepared according to the method of the first or second aspect.

In a fourth aspect, a method of separating an aromatic compound from a mixture of hydrocarbons is provided. The method includes several steps. The first step includes contacting the mixture of hydrocarbons with a separation medium. The second step includes resolving the aromatic compound from the mixture of hydrocarbons. The third step includes isolating the aromatic compound from the mixture of hydrocarbons. The separation medium consists of a cyclodextrin metal-organic framework (CD-MOF) that is prepared according to a method of the first or second aspect.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects and advantages other than those set forth above will become more readily apparent when consideration is given to the detailed description below. Such detailed description makes reference to the following drawings.

Figure 1A:
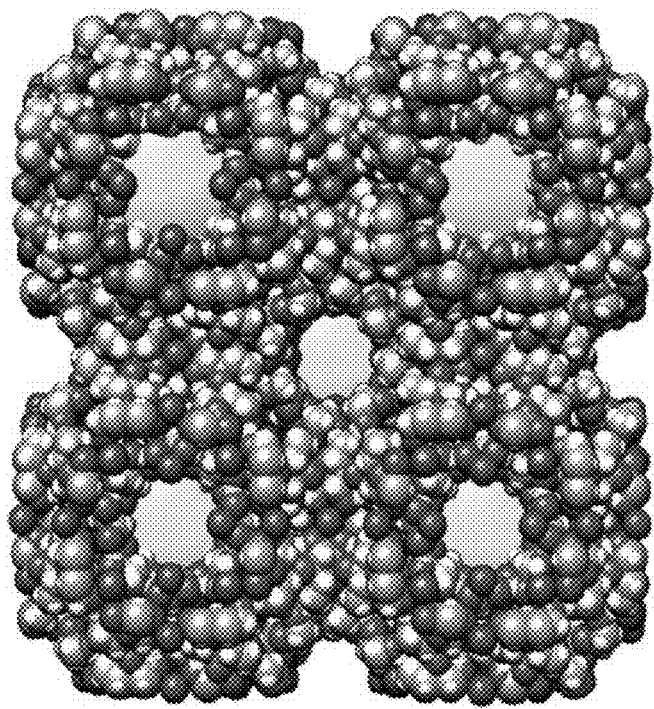
FIG. 1A shows an exemplary space-filling representation, viewed along the ⟨1 0 0⟩ axis, revealing the extended structure of the body-centered cubic packing arrangement in CD-MOF-1 (C, light gray; 0, red; K, purple). Note that CD-MOF-2 has an identical extended structure but with $Rb^+$ instead of $K^+$ ions.
Figure 1B:
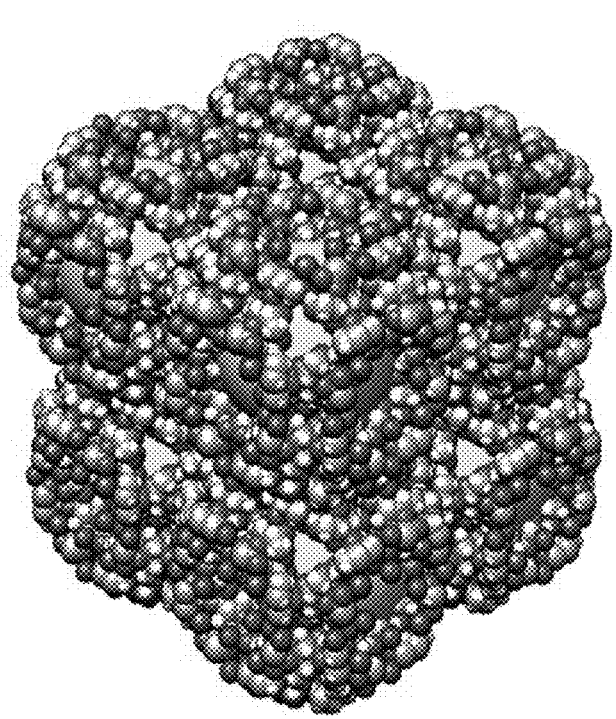
FIG. 1B depicts an exemplary space-filling representation of CD-MOF-1, viewed along the ⟨1 1 1⟩ axis, revealing the triangular windows. The large cavities are filled will yellow spheres.
Figure 1C:
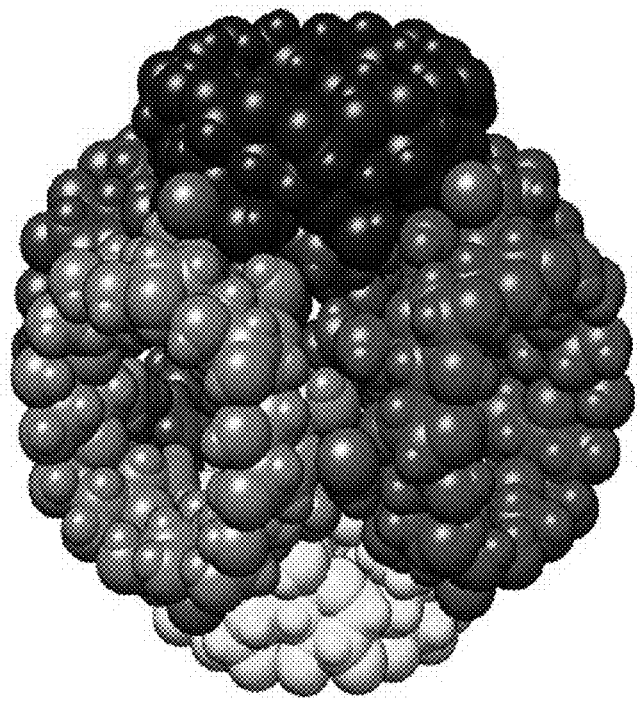
FIG. 1C depicts an exemplary cuboidal topology of the $(\gamma\text{-CD})_6$ units, viewed along the ⟨1 1 1⟩, where each γ-CD is represented as a space-filling display in a contrasting color.
Figure 1D:
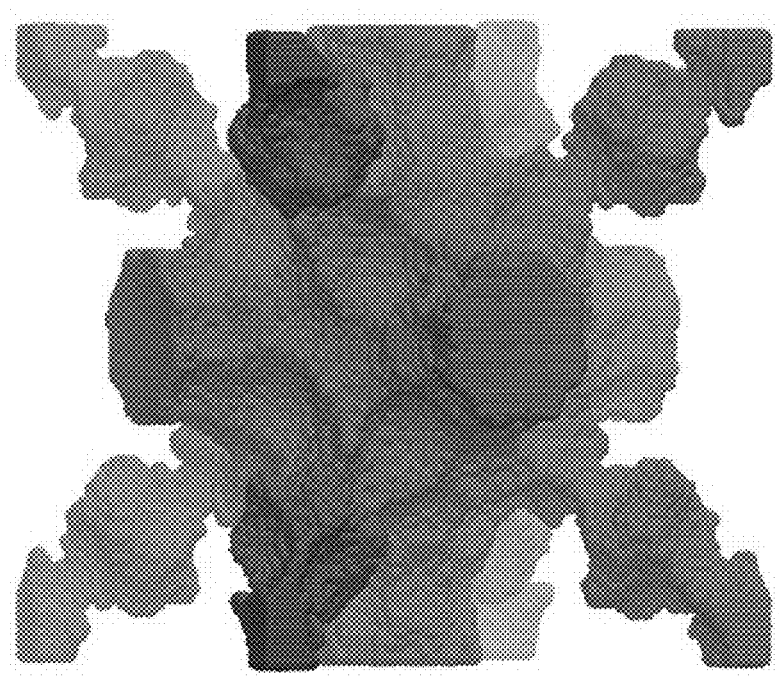
FIG. 1D depicts an exemplary illustration of the pore void within CD-MOF-1, viewed along the ⟨1 1 1⟩ axis, where the void is colored purple and the atoms of CD-MOF-1 are removed for the sake of clarity.

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The compositions and methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "cyclodextrin" includes cyclodextrin, γ-cyclodextrin and derivatives thereof.

Overview

Applicants have discovered a novel set of γ-cyclodextrin metal-organic frameworks (CD-MOFs) as a separation medium for purifying alkylaromatic and haloaromatic compounds from a mixture of hydrocarbons (see, for example, FIG. 1). The CD-MOFs are composed of "green" (that is, renewable and recyclable) starting materials that are readily available. The CD-MOFs can be tailor-made on the kilogram scale, thereby enabling their use in industrial scale separations. The utility of the CD-MOFs is demonstrated for the most challenging separations of petrochemical feedstocks, including benzene, toluene, ethylbenzene, and the regioisomers of xylenes, with separation factors and resolutions superior to those reported for other extended-framework materials.

CD-MOF Compositions, Methods of Synthesis and Use as Separation Media

In one aspect, a separation medium is provided for purifying alkylaromatic and haloaromatic compounds from a mixture of hydrocarbons. The separation medium consists of cyclodextrin metal-organic frameworks (CD-MOFs) that are formed from reaction of cyclodextrin with alkali metal salt in the presence of water and alcohol. A preferred cyclodextrin includes γ-cyclodextrin for the CD-MOFs disclosed herein. Exemplary CD-MOFs include CD-MOF-1 (CD-MOF formed by reaction of γ-cyclodextrin with KOH), CD-MOF-2 (CD-MOF formed by reaction of γ-cyclodextrin with RbOH) and CD-MOF-3 (CD-MOF formed by reaction of γ-cyclodextrin with CsOH). Other CD-MOFs having similar performance attributes can be made from other alkali metal salts under similar conditions.

For adapting CD-MOFs as a separation medium, particle size of CD-MOF population can be preferably adjusted post-preparation or during preparation of the CD-MOF crystalline material. Two general methods, so-called "top-down" and "bottom-up" approaches, can be used for preparing CD-MOF material of the appropriate particle size. In the top-down approach, the CD-MOF crystalline material is grown during an initial synthesis, followed by reducing the particle size of the resultant material using any known particle size reduction technique (for example, grinding with pestle/mortar, sonication and ball milling, among others) and thereafter applying a particle size-specific sieving method to obtain a CD-MOF particle population having the desired particle size range. In the bottom-up approach, the CD-MOF crystalline material is grown to the desired size range during synthesis, where particle size control, using the mother liquor of the standard CD-MOF synthesis, is determined by short incubation times and the quantity of a suitable surfactant, such as cetyltrimethylammonium bromide (CTAB), Pluronic P-123 and Pluronic F-127, among others, added to the solution. In lieu of adding a suitable surfactant, the resultant mixture of mother liquor can be stirred slowly to achieve comparable results. Submicron-sized particles of CD-MOF can be obtained under conditions of treating mixtures including 50 mM γ-cyclodextrin with stirring at 250 rpm. Though CD-MOF particles in the submicron range may not be amenable for HPLC applications, other separation applications (for example, gas phase) can be used with these materials. Larger CD-MOF particles can be obtained with stirring solutions of γ-cyclodextrin having concentrations more dilute than 50 mM. The effect of the final CD-MOF-1 particle size as a function of the amount of CTAB as surfactant included in the synthesis solution is summarized in Table 1.

TABLE 1

CD-MOF-1 particle size ranges with varying CTAB concentrations[a]

| material | CTAB/mg | particle size/μm |
|---|---|---|
| CD-MOF-1-Micro1 | 20 | 25 |
| CD-MOF-1-Micro2 | 40 | 10-15 |
| CD-MOF-1-Micro3 | 60 | 5-15 |
| CD-MOF-1-Micro4 | 80 | 1-10 |

[a]See Examples for details. Particle sizes were confirmed by optical microscopy and scanning electron microscopy.

The bottom-up approach is generally preferred over the top-down approach for preparing CD-MOF material of the appropriate particle size. First, not all CD-MOF material can be prepared in suitable form with the top-down approach. For example, CD-MOF-2 remained crystalline during the column preparation stages, and it was shown to be suitable for separation experiments. By contrast, CD-MOF-1 did not retain its crystallinity during top-down processing and so could not be employed in top-down separation experiments. Because the particle size reduction methods of the top-down approach can adversely affect the quality of the final CD-MOF product as a separation medium, depending upon the CD-MOF composition used during initial synthesis, additional quality controls are performed to ensure the suitability as a separation medium of a CD-MOF composition prepared by the top-down approach. Similar quality control procedures may be avoided altogether for CD-MOF materials prepared with the bottom-up approach.

Second, the bottom-up approach can be more efficient than the top-down approach. For example, the majority, if not all, of the CD-MOF material prepared by the bottom-up approach can be used as a separation medium, because the CD-MOF material is crystallized to the desired particle size range during synthesis. By contrast, the top-down approach can result in lower yields as some of the original CD-MOF material is inevitably lost during particle size reduction and particle size selection with sieves.

Third, the top-down approach can yield CD-MOF compositions having lower performance attributes as a separation medium compared with CD-MOF compositions prepared with the bottom-up approach. One explanation for the difference pertains to the differences in particle size range used as separation medium obtained with the two approaches. The bottom-up approach can yield a particle size having a narrower distribution than attainable with the top-down approach, which can provide for a more uniform packing within separation columns. By contrast, the top-down approach typically yields CD-MOF material having a large particle size range and top-down CD-MOF columns result in inefficient stationary-phase packing as a consequence of the large particle size range.

The CD-MOF compositions as separation media prepared from the bottom-up approach as described herein have preferred particle sizes having a mean diameter in the range from about 1 micron to about 25 microns. More preferably, the particle sizes have a mean diameter in a sub-range from about 1 micron to about 20 microns; from about 1 micron to about 15 microns; from about 1 micron to about 10 microns; from about 5 microns to about 25 microns, from about 5 microns to about 20 microns; from about 5 microns to about 15 microns; from about 5 microns to about 10 microns; from about 10 microns to about 25 microns; from about 10 microns to about 20 microns; from about 10 microns to about 15 microns; from about 15 microns to about 25 microns; from about 15 microns to about 20 microns; and from about 20 microns to about 25 microns. Highly preferred particle sizes have a mean diameter from about 5 microns to about 10 microns; from about 10 microns to about 15 microns; and from about 5 microns to about 15 microns. Other ranges and sub-ranges within the broadest range from about 1 micron to about 25 microns also fall within the scope of the invention.

The CD-MOF compositions as separation media prepared with the top-down approach as described herein have preferred particle sizes having a mean diameter typically larger than that produced for CD-MOF compositions prepared with the bottom-up approach as described here, wherein preferred particle sizes having a mean diameter in the range from about 1 micron to about 50 microns, including sub-ranges from about 1 micron to about 40 microns; from about 1 micron to about 30 microns; from about 1 micron to about 20 microns; from about 1 microns to about 10 microns, from about 5 microns to about 50 microns; from about 5 microns to about 40 microns; from about 5 microns to about 30 microns; from about 5 microns to about 20 microns; from about 5 microns to about 10 microns; from about 10 microns to about 50 microns; from about 10 microns to about 40 microns; from about 10 microns to about 30 microns; from about 10 microns to about 20 microns; from about 15 microns to about 50 microns; from about 15 microns to about 40 microns; from about 15 microns to about 30 microns; from about 15 microns to about 20 microns; from about 20 microns to about 50 microns; from about 20 microns to about 40 microns; from about 20 microns to about 30 microns; and from about 20 microns to about 25 microns. Highly preferred particle sizes have a mean diameter from about 5 microns to about 10 microns; from about 10 microns to about 15 microns; and from about 5 microns to about 15 microns. Other ranges and sub-ranges within the broadest range from about 1 micron to about 50 microns also fall within the scope of the invention.

In one aspect, a method of preparing a separation medium consisting of a γ-cyclodextrin metal-organic framework (CD-MOF) is provided. The method includes several steps.

The first step includes preparing a first mixture comprising cyclodextrin and an alkali metal salt in water. The second step includes adding a first aliquot of alcohol to the first mixture to form a second mixture. The third step includes adding an amount of a surfactant to the second mixture to form a third mixture. The fourth step includes adding a second aliquot of alcohol to the third mixture to form a fourth mixture. The fifth step includes crystallizing the CD-MOF from the fourth mixture. A highly preferred cyclodextrin for this method includes γ-cyclodextrin.

In another aspect, a method of preparing a separation medium consisting of a cyclodextrin metal-organic framework (CD-MOF) is provided. The method includes several steps. The first step includes preparing a first mixture comprising a cyclodextrin, an alkali metal salt, water and an alcohol. The second step includes performing one of the following two steps: (a) stirring the first mixture or (b) adding an amount of a surfactant to the first mixture to form a second mixture. The third step includes crystallizing the CD-MOF from the first mixture or the second mixture. A highly preferred cyclodextrin for this method includes γ-cyclodextrin.

In another aspect, a method of preparing a separation medium consisting of a cyclodextrin metal-organic framework (CD-MOF) is provided. The method includes several steps. The step includes preparing a first mixture comprising the cyclodextrin, an alkali metal salt, water and an alcohol. The second step includes crystallizing the CD-MOF from the first mixture. A third step includes optionally performing particle size reduction of the crystallized CD-MOF. A highly preferred cyclodextrin for this method includes γ-cyclodextrin.

In another aspect, a method of separating aromatic compounds from a hydrocarbon mixture is provided. The method includes the step of contacting the hydrocarbon mixture with a separation medium comprising a cyclodextrin metal-organic framework (CD-MOF). Exemplary CD-MOF compositions include CD-MOF-1, CD-MOF-2 and CD-MOF-3, among others. Preferably, the CD-MOF compositions comprise CD-MOFs prepared using a bottom-up approach. In other respects, the CD-MOF compositions can comprise CD-MOFs prepared using a top-down approach. In all respects, a highly preferred cyclodextrin for the method includes γ-cyclodextrin. The CD-MOF compositions can be disposed as a stationary phase in a column for performing chromatographic separation of the hydrocarbon mixture or utilized as separation medium in gas phase separations. A preferred chromatographic separation for this purpose includes high performance liquid chromatography (HPLC). Since hydrocarbons are generally hydrophobic, a preferred chromatography medium includes hydrophobic solvents or solvents miscible with water, such as, for example, hexane, methylene chloride, methanol, 2-propanol, among others.

Preferred aromatic compounds for separation include alkylaromatic compounds and haloaromatic compounds. Exemplary alkylaromatic compounds include toluene, ethylbenzene, isomers of xylene, styrene, α-methylstyrene, cumene, ethyltoluene, 2-methylstyrene, 3-methylstyrene, and 4-methylstyrene, among others. Exemplary haloaromatic include mono- and di-substituted aromatic compounds, such as fluorobenzene, chlorobenzene, bromobenzene, iodobenzene, 1,2-dibromobenzene, 1,3-dibromobenzene, 1,4-dibromobenzene, 1-bromo-2-iodobenzene, 1-bromo-3-iodobenzene, 1-bromo-4-iodobenzene, 1,2-diiodobenzene, 1,2-dichlorobenzene, and halo-substituted toluene derivatives, such as α,α,α-trifluorotoluene. A listing of such alkylaromatic compounds and haloaromatic compounds is not exhaustively presented herein; suffice it to say, any known alkylaromatic compounds and haloaromatic compounds can be capable of separation from a mixture of hydrocarbons using the CD-MOF separation medium disclosed herein.

These principles are illustrated by the following experiments with CD-MOF-2 prepared by a top-down approach and CD-MOF-1 prepared by a bottom-up approach.

Figure 2A:
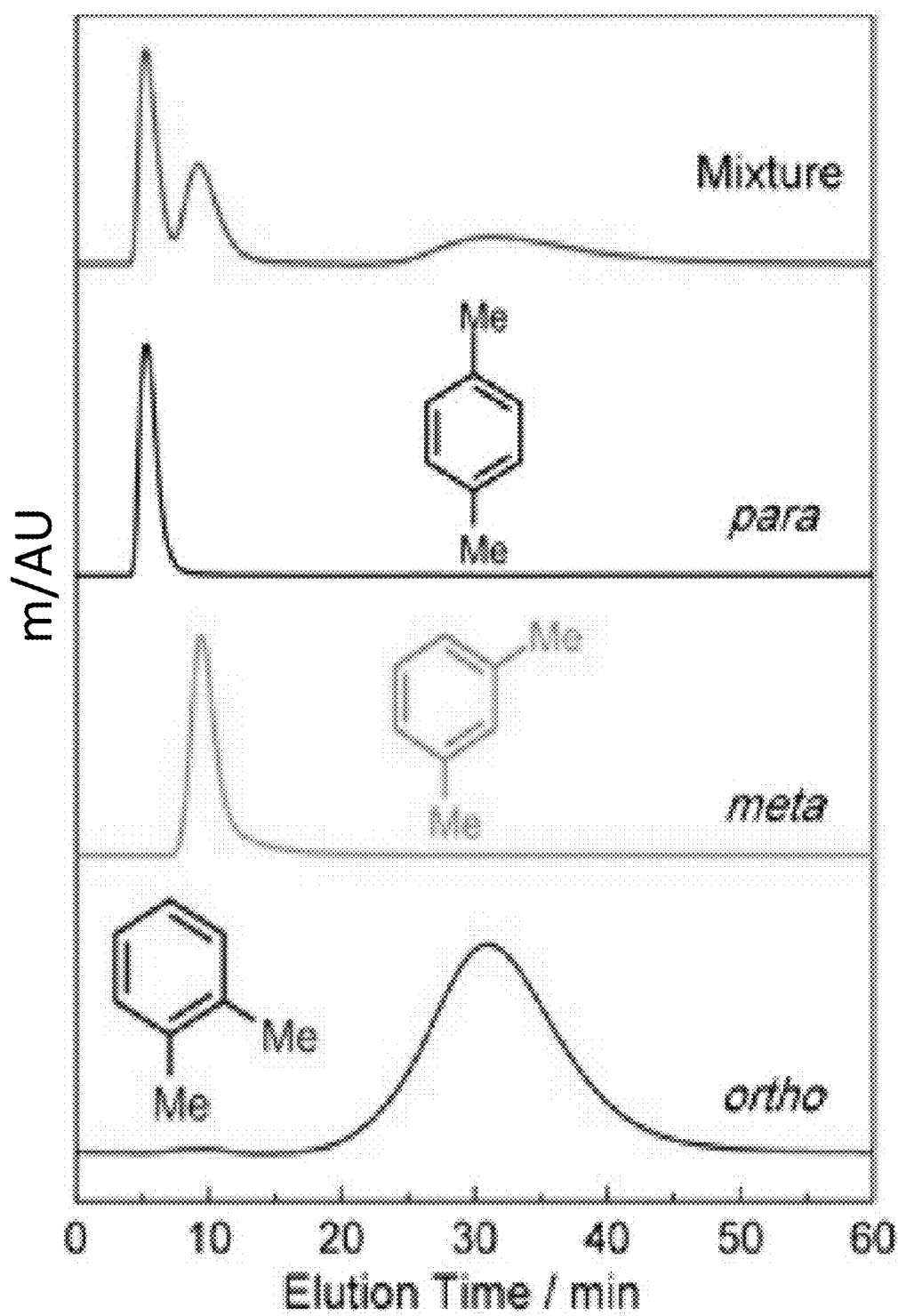
FIG. 2A depicts liquid-phase chromatographic separations of 50 mg $mL^{-1}$ xylene mixtures in HPLC-grade hexane at a flow rate of 1 mL $min^{-1}$ at 298 K using CD-MOFs as the stationary phase for an exemplary top-down CD-MOF-2 column (particle size 10-37 μm).

The top-down CD-MOF-2 HPLC column exhibited (FIG. 2A) partial separation of p- and m-xylene, followed by the complete separation of the o-xylene isomer. The high selectivity (separation factor $\alpha_{oxpx}$=16.4) of CD-MOF-2 for o- over p-xylene and the preference ($\alpha_{mxpx}$=3.44) for m- over p-xylene indicate (Table 2) the potential of CD-MOF-2 as a viable separation medium for the regioisomers of xylenes when compared (Table 3) to previously published[20,21,25] separations using MOFs. The resolution of the p- and m-xylene signals (resolution factor $R_{mxpx}$=0.58), however, exhibits (FIG. 2A) peak-merging near the baseline. The low resolution of the p- and m-xylene isomers can be attributed to inefficient stationary-phase packing that is a consequence of the large particle size range produced during the preparation of the top-down CD-MOF-2 HPLC column. In a bid to overcome these resolution limitations, a bottom-up protocol for size-controlled growth of CD-MOF was implemented by modification of a previously reported methodology.[32]

TABLE 2

CD-MOF column separation factors of xylene mixtures using n-hexane as the mobile phase at a flow rate of 1 mL min$^{-1}$

| | | | j | | |
|---|---|---|---|---|---|
| absorbent | mixture | i | ortho-xylene | meta-xylene | para-xylene |
| CD-MOF-2 | 50 mg/ml | ortho-xylene | — | 4.76 | 16.37 |
| top-down | xylenes | meta-xylene | 0.21 | — | 3.44 |
| column | in hexane | para-xylene | 0.06 | 0.29 | — |
| CD-MOF-1 | 50 mg/ml | ortho-xylene | — | 6.73 | 17.93 |
| bottom-up | xylenes | meta-xylene | 0.15 | — | 2.67 |
| column | in hexane | para-xylene | 0.06 | 0.38 | — |
| CD-MOF-1 | neat | ortho-xylene | — | 5.72 | 10.76 |
| bottom-up | xylenes | meta-xylene | 0.17 | — | 1.88 |
| column | | para-xylene | 0.09 | 0.53 | — |

TABLE 3

Separation factors of prior art frameworks for the three xylene isomers and ethylbenzene

| absorbent | solvent | i | o-xylene | m-xylene | p-xylene | Ethylbenzene | Ref |
|---|---|---|---|---|---|---|---|
| HKUST-1 | hexane | o-xylene | — | 0.4 | 0.7 | 0.7 | 20 |
| [$Cu_3(BTC)_2$] | | m-xylene | 2.4 | — | 1.1 | 1.4 | |
| | | p-xylene | 1.4 | 0.9 | — | 1.2 | |
| | | ethylbenzene | 1.4 | 0.7 | 0.8 | — | |
| MIL-47 | hexane | o-xylene | — | 2.0 | 1.4 | 10.9 | 21 |
| | | m-xylene | 0.5 | — | 0.4 | 4.2 | |
| | | p-xylene | 0.7 | 2.9 | — | 9.7 | |
| | | ethylbenzene | 0.1 | 0.2 | 0.1 | — | |
| MIL-53(Al) | hexane | o-xylene | — | 2.7 | 3.5 | 10.9 | 20, 21 |
| | | m-xylene | 0.4 | — | 1.2 | 3.8 | |
| | | p-xylene | 0.3 | 0.8 | — | 3.1 | |
| | | ethylbenzene | 0.1 | 0.3 | 0.3 | — | |
| MIL-53(Fe) | heptane | o-xylene | — | 1.3 | 3.5 | 12.3 | 25 |
| | | m-xylene | 0.7 | — | 2.5 | 9.2 | |
| | | p-xylene | 0.3 | 0.4 | — | 3.5 | |
| | | ethylbenzene | 0.1 | 0.1 | 0.3 | — | |

The bottom-up synthesis facilitates rapid gram-scale production of 10-15 μm CD-MOF-1 particles. Not only is it attractive on a large scale to use the CD-MOF containing potassium ions, but it also transpires that CD-MOF-1 lends itself to more precise control of the particle size. The control of CD-MOF particle size for the bottom-up production of HPLC columns was achieved through the modification of a previously reported method[31] where particle size control, using the mother liquor of the standard CD-MOF synthesis, is determined by short incubation times and the quantity of CTAB added to the solution.[30,32] Varying the quantity of CTAB during the crystallization of CD-MOF analogues to form micrometer-sized crystallites is particularly effective in the synthesis of CD-MOF-1 since increasing the amount of CTAB in each crystallization solution from 20 to 80 mg reduces the size of CD-MOF-1 crystals from ≥25 to ≤10 respectively (see Table 1). Particle size was evaluated using OM and SEM, while the crystallinity of CD-MOF-1 samples corresponding to varying CTAB additions were confirmed by powder X-ray diffraction. On the basis of these investigations, it was decided to proceed with the scale-up of CD-MOF-1, with each crystallization solution containing 40 mg CTAB, so as to produce particles with a size distribution of 10-15 μm for optimized packing of the CD-MOF within HPLC columns.

Figure 2B:
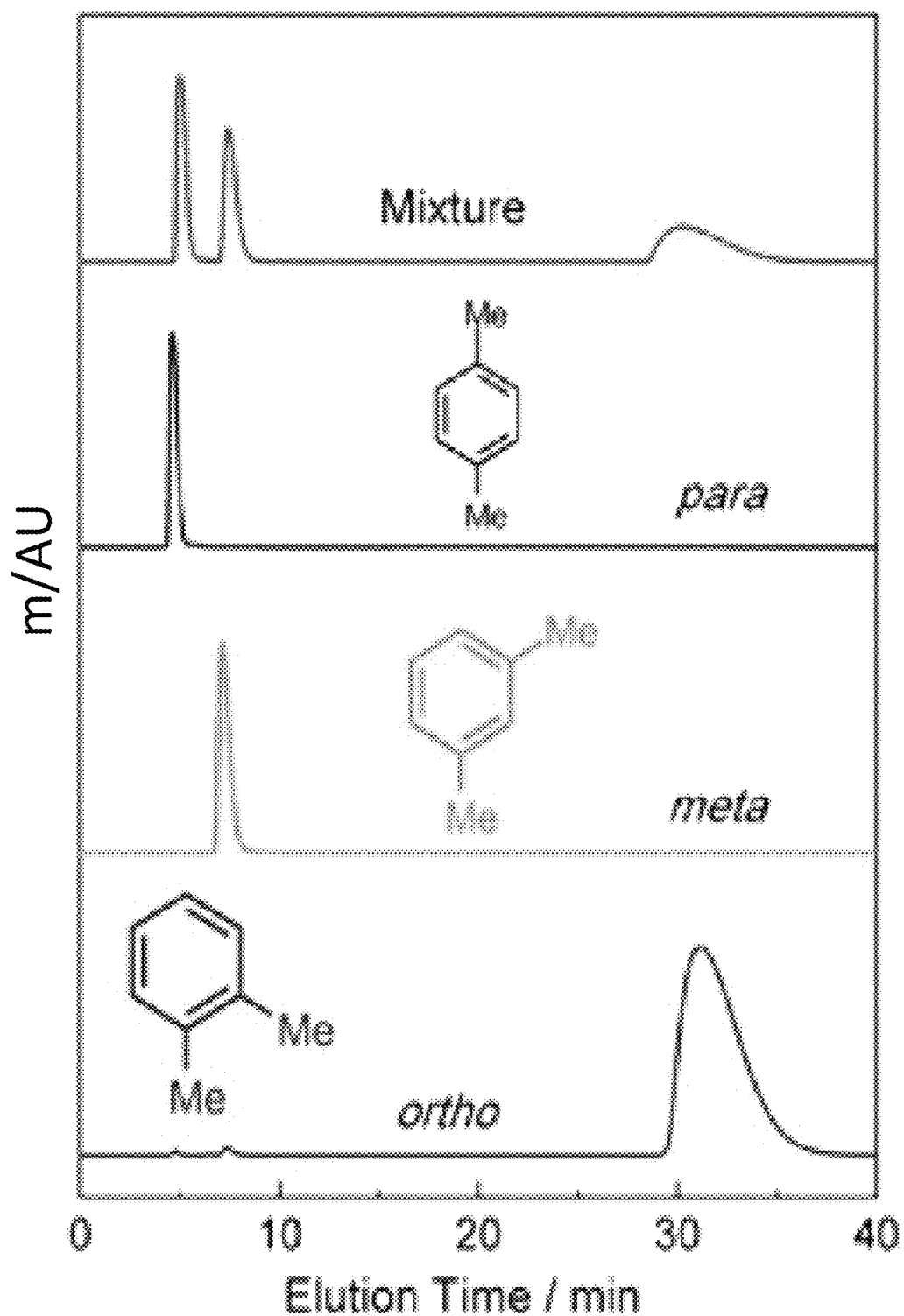
FIG. 2B depicts liquid-phase chromatographic separations of 50 mg $mL^{-1}$ xylene mixtures in HPLC-grade hexane at a flow rate of 1 mL $min^{-1}$ at 298 K using CD-MOFs as the stationary phase for an exemplary bottom-up CD-MOF-1 column (particle size 10-15 μm). The separation profiles display the assignment of the elution order from a mixture (red) of xylene isomers and pure components of p- (black), m- (green), and o-xylene (blue).

Baseline separation (FIG. 2B) of all three xylene regioisomers was observed using the bottom-up CD-MOF-1 stationary phase. The elution order remains unchanged, with p-, followed by m- and finally o-xylene and retention times similar to those observed for the top-down column. The bottom-up CD-MOF-1 column provides much improved signal resolutions ($R_{mxpx}$=2.17 and $R_{oxpx}$=6.43) and separation factors ($\alpha_{mxpx}$=2.67, $\alpha_{oxpx}$=17.9, and $\alpha_{oxmx}$=6.73) compared to the values obtained using the top-down approach (Table 2). Comparison of CD-MOF-1 with previously reported MOFs shows higher separation factors to separate the xylene regioisomers compared[20,25] to MIL-53(Fe) and MIL-47 (Table 3). In addition, the green nature of CD-MOF-1 provides a separation medium with a significantly reduced carbon foot-print compared to that of the terephthalate-based MIL materials.

Figure 3A:
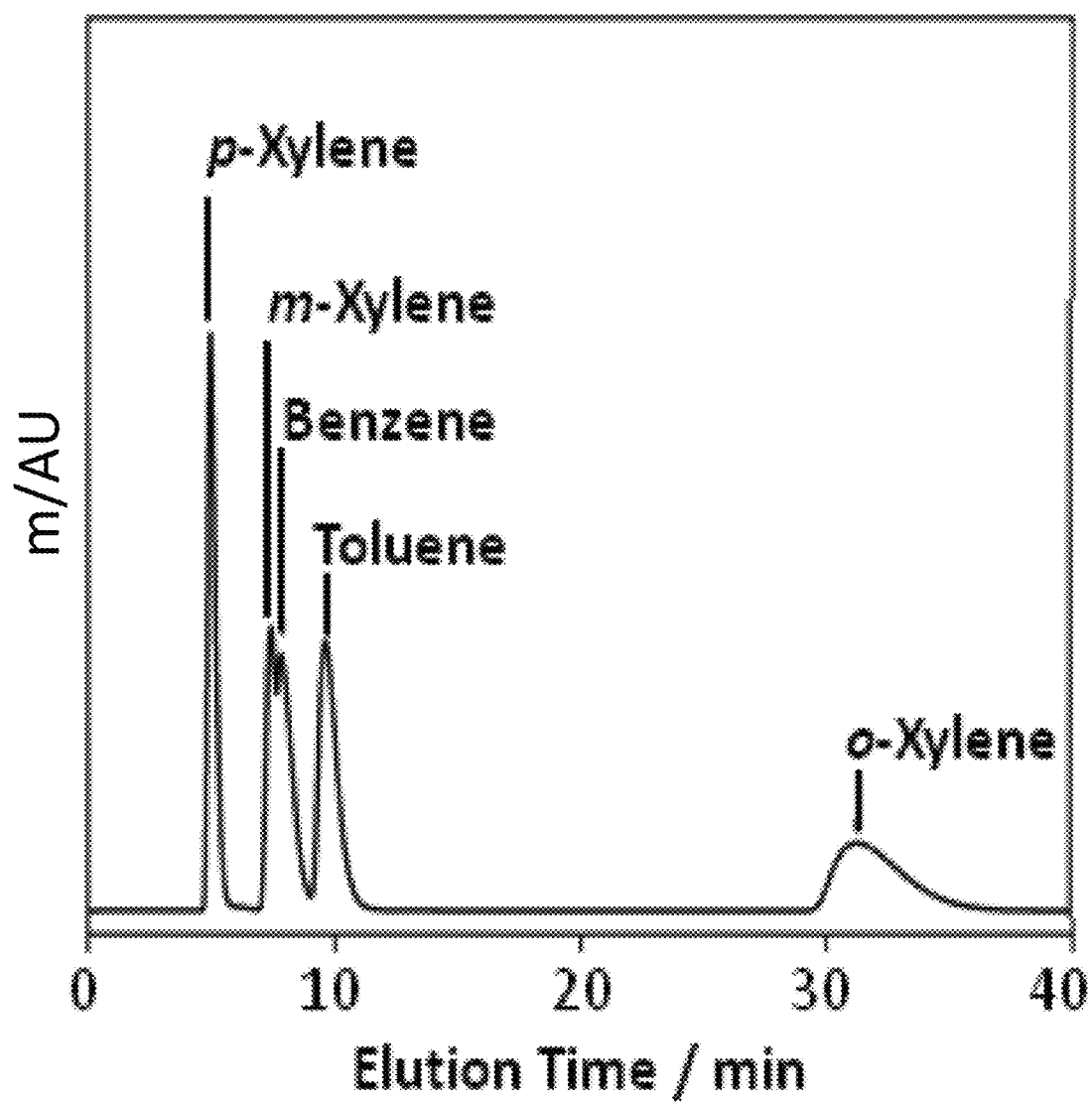
FIG. 3A depicts an exemplary bottom-up CD-MOF-1 column (particle size 10-15 μm) separations of a 50 mg $mL^{-1}$ BTX mixture in HPLC-grade hexane at a flow rate of 1 mL $min^{-1}$ at 298 K after activating the column for 4 h.
Figure 3B:
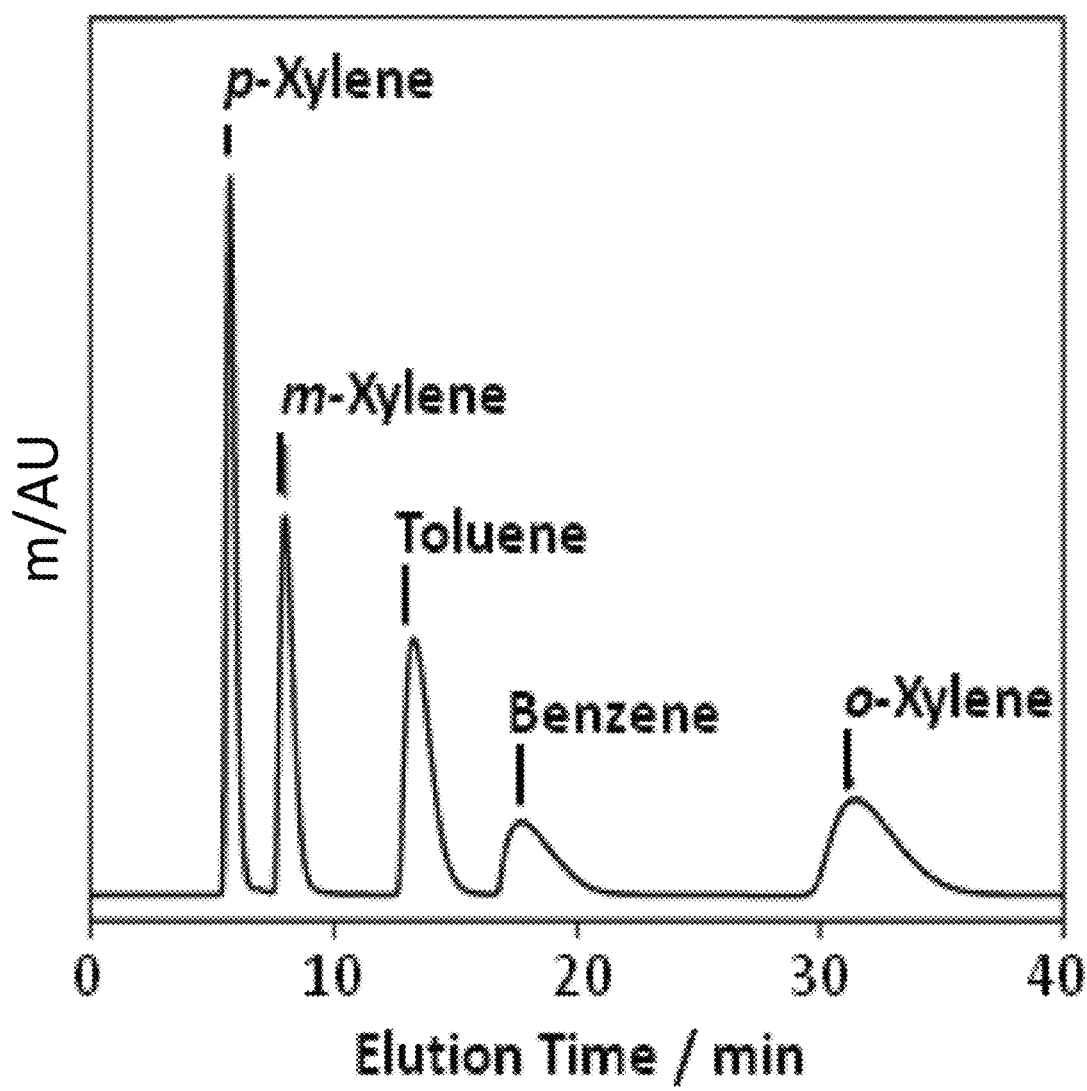
FIG. 3B depicts an exemplary bottom-up CD-MOF-1 column (particle size 10-15 μm) separations of a 50 mg $mL^{-1}$ BTX mixture in HPLC-grade hexane at a flow rate of 1 mL $min^{-1}$ at 298 K after activating the column for 30 h.
Figure 3C:
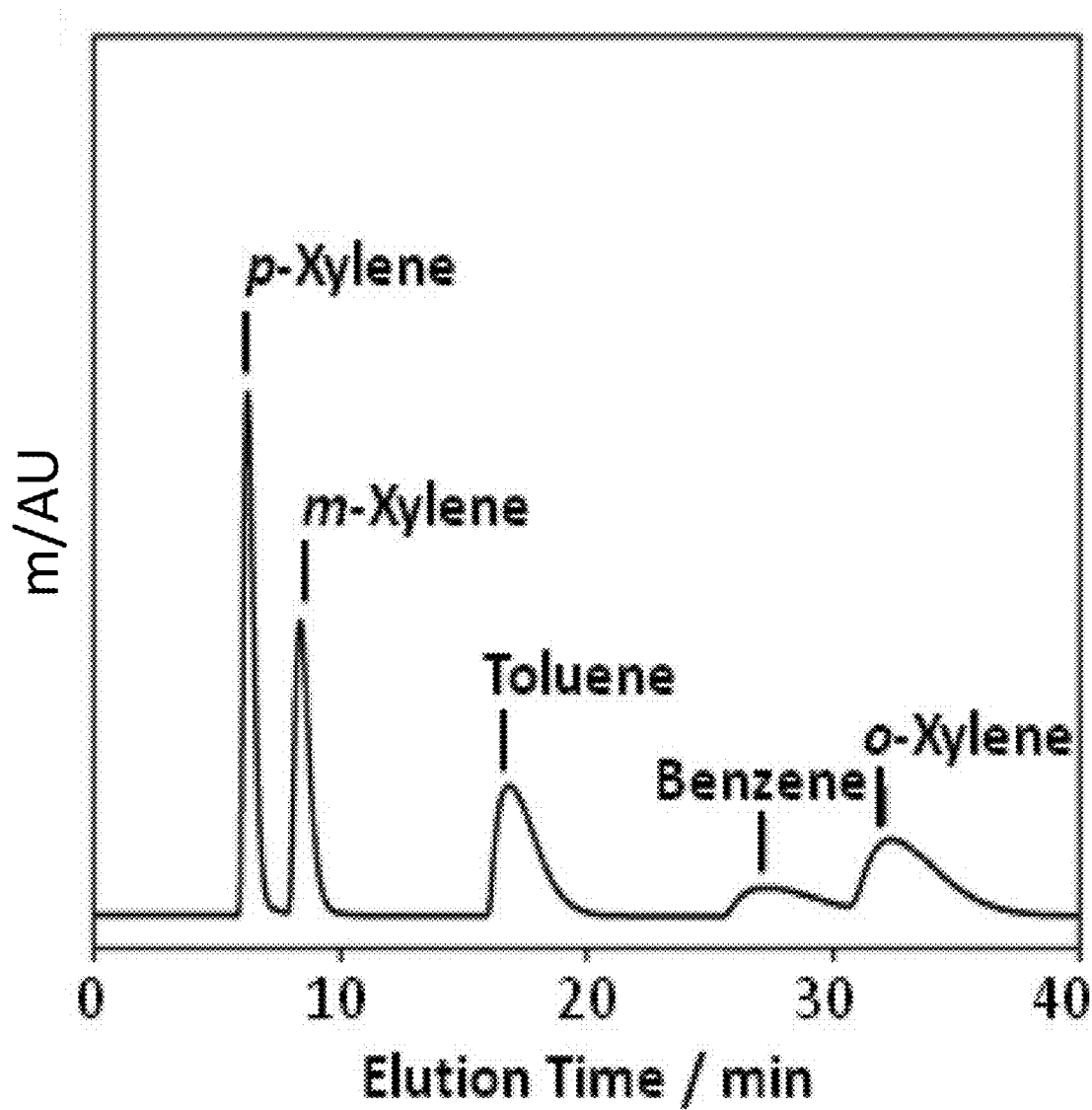
FIG. 3C depicts an exemplary bottom-up CD-MOF-1 column (particle size 10-15 μm) separations of a 50 mg $mL^{-1}$ BTX mixture in HPLC-grade hexane at a flow rate of 1 mL $min^{-1}$ at 298 K after activating the column for 60 h.
Figure 3D:
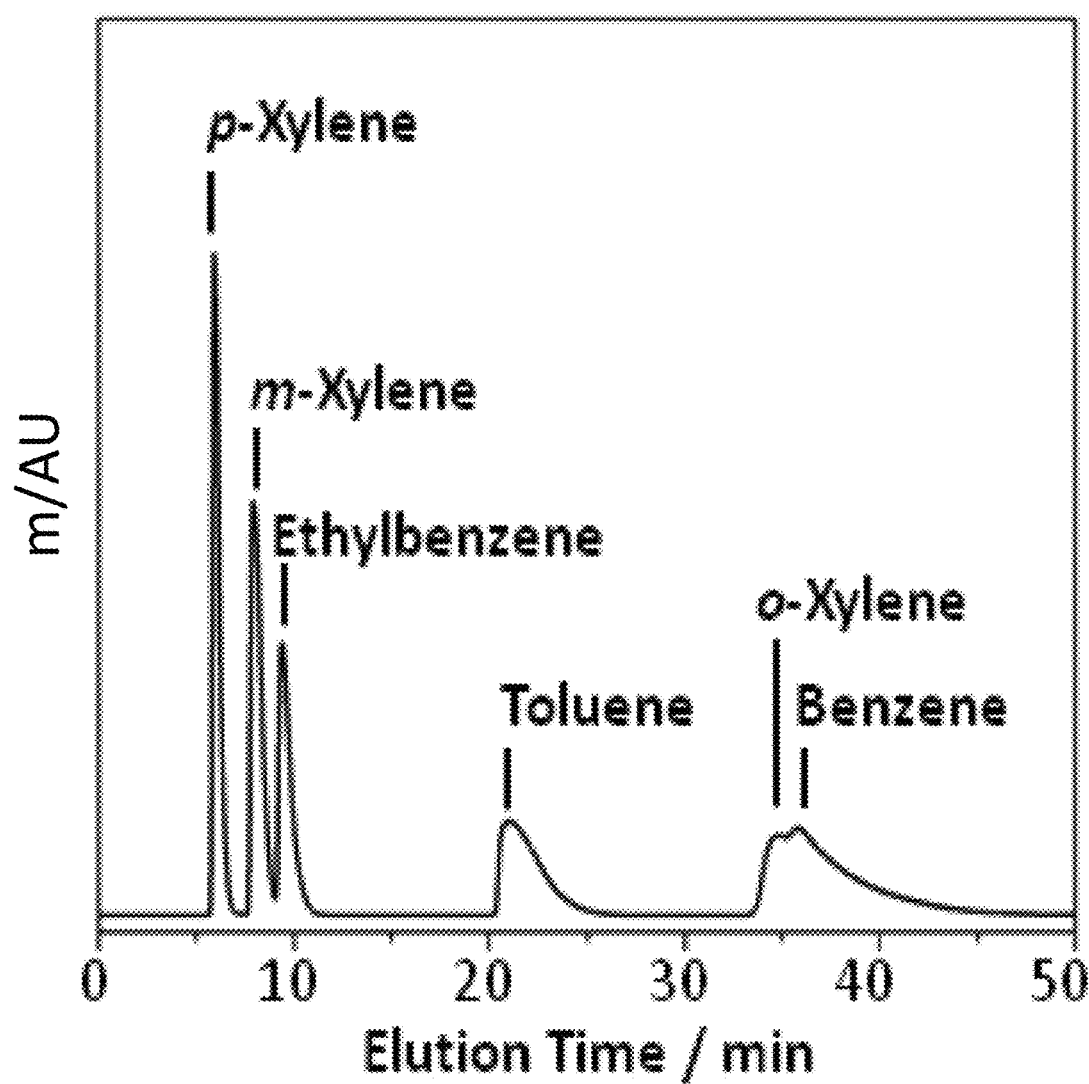
FIG. 3D depicts an exemplary bottom-up CD-MOF-1 column (particle size 10-15 μm) separations of a 50 mg $mL^{-1}$ BTEX mixture in HPLC-grade hexane at a flow rate of 1 mL $min^{-1}$ at 298 K after activating the column for 30 h.

As part of an effort to investigate the versatility of CD-MOF-1 as a separation medium, BTX and BTEX mixtures were tested on the bottom-up column. Initial separation runs of BTX after 4 h of column usage, with hexane as the mobile phase, demonstrated (FIG. 3A) that CD-MOF-1 can separate toluene from the xylene isomers at 298 K, but with no separation of benzene from m-xylene. With continued usage of the column in the presence of hexane, however, the separation of toluene and benzene from m-xylene can be achieved (FIG. 3B) after 30 h, resulting in an improvement of the separation factors (see Example 5, Table 8) from $\alpha_{bmx}$=1.12 and $\alpha_{tmx}$=1.58 to $\alpha_{bmx}$=3.10 and $\alpha_{tmx}$=2.17. We believe that MeOH retained in the MOF from the particle preparation, is displaced slowly by hexane. These vacated sites within the framework are selective for toluene and benzene—the retention of benzene on the column is similar (FIG. 3C) to that of o-xylene after 70 h—preventing the complete separation of the BTX mixture when MeOH occupies them.

Figure 3E:
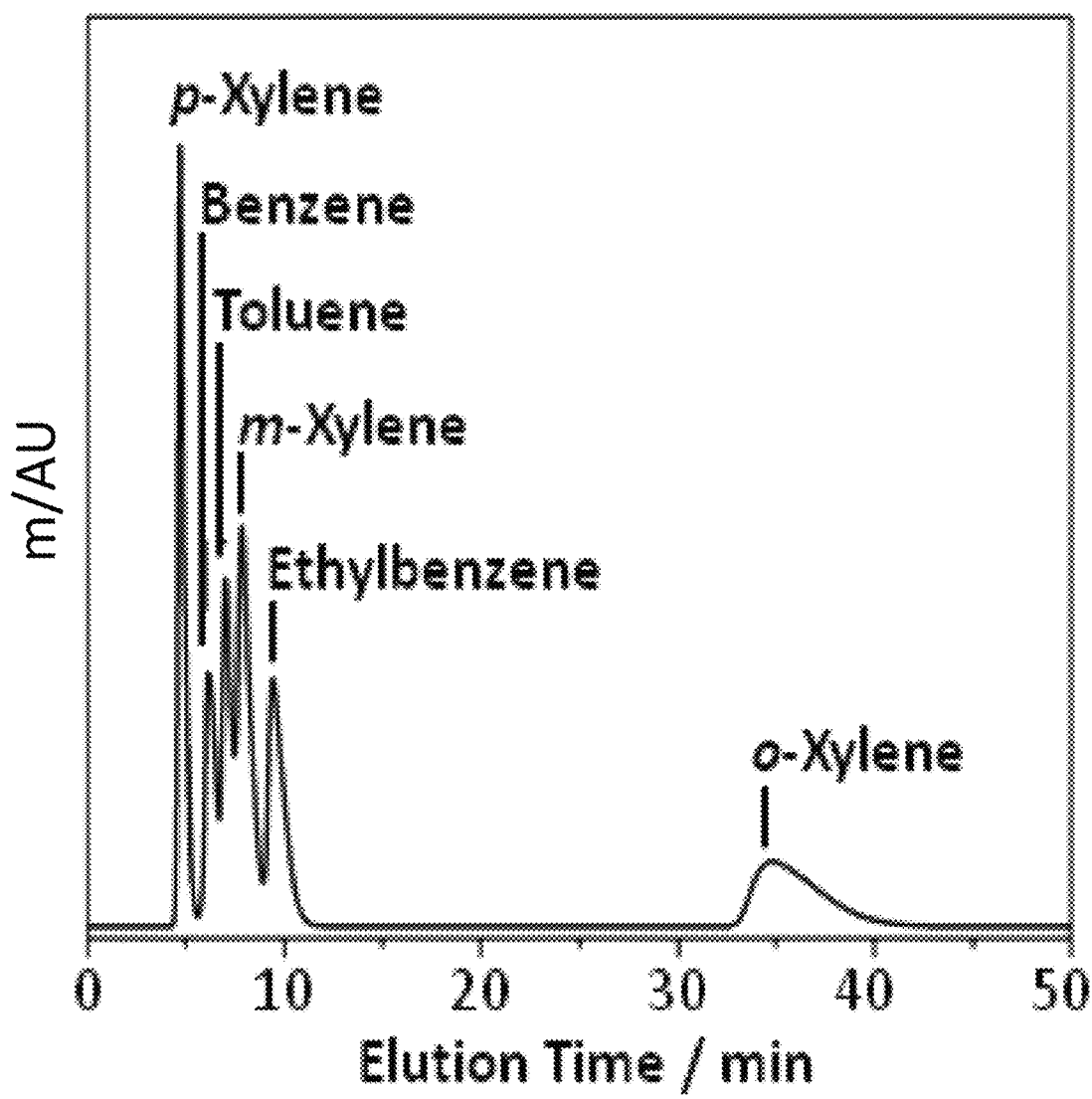
FIG. 3E depicts an exemplary bottom-up CD-MOF-1 column (particle size 10-15 μm) separations of a 50 mg $mL^{-1}$ BTEX mixture in HPLC-grade hexane at a flow rate of 1 mL $min^{-1}$ at 298 K after deactivating the column using hexane/$^i$PrOH (98/2, v/v).
Figure 3F:
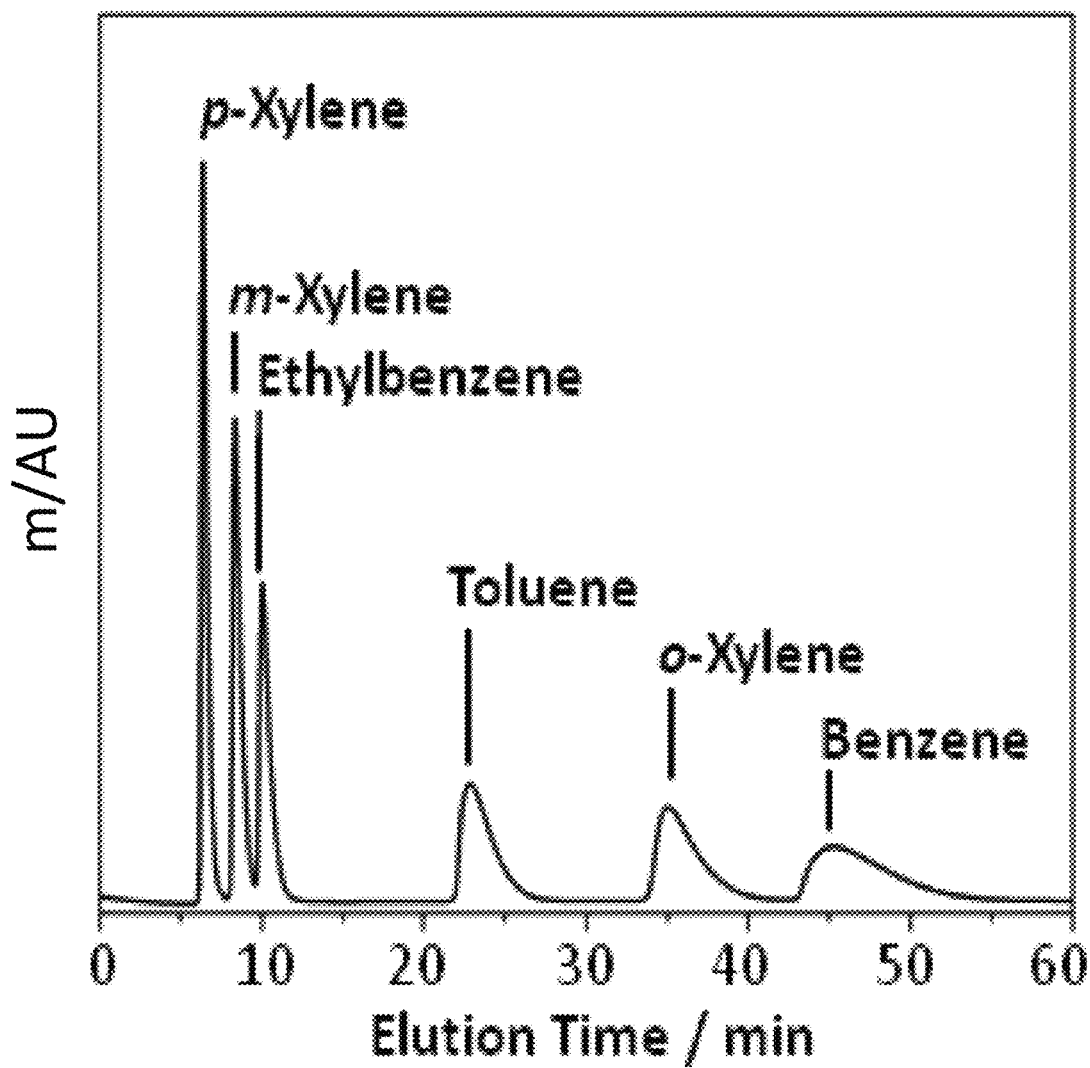
FIG. 3F depicts an exemplary bottom-up CD-MOF-1 column (particle size 10-15 μm) separations of a 50 mg $mL^{-1}$ BTEX mixture in HPLC-grade hexane at a flow rate of 1 mL $min^{-1}$ at 298 K after reactivation using $CH_2Cl_2$.
Figure 4A:
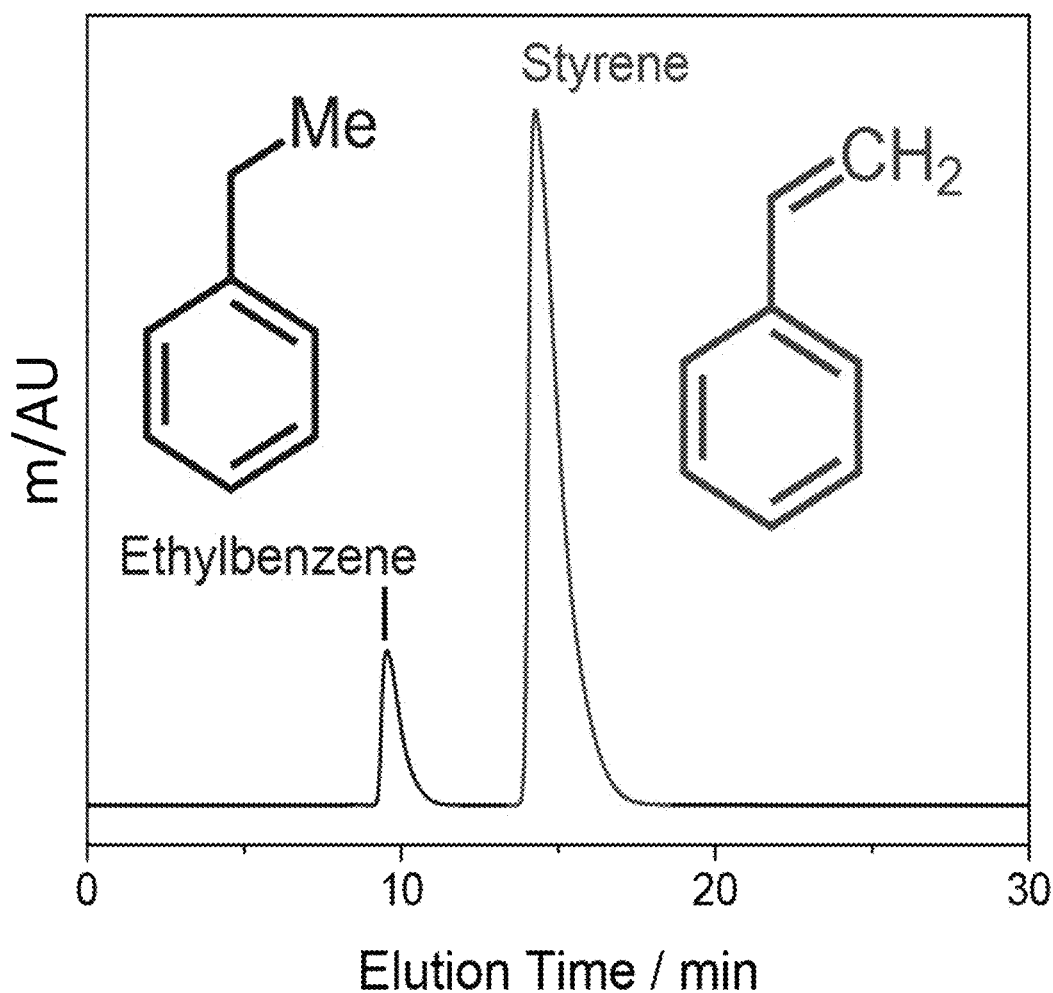
FIG. 4A depicts an exemplary bottom-up CD-MOF-1 column (particle size 10-15 μm) separations of a 10 μL sample of 50 mg $mL^{-1}$ ethylbenzene and styrene mixture in HPLC-grade hexane at a flow rate of 1 mL $min^{-1}$ at 298 K.
Figure 4B:
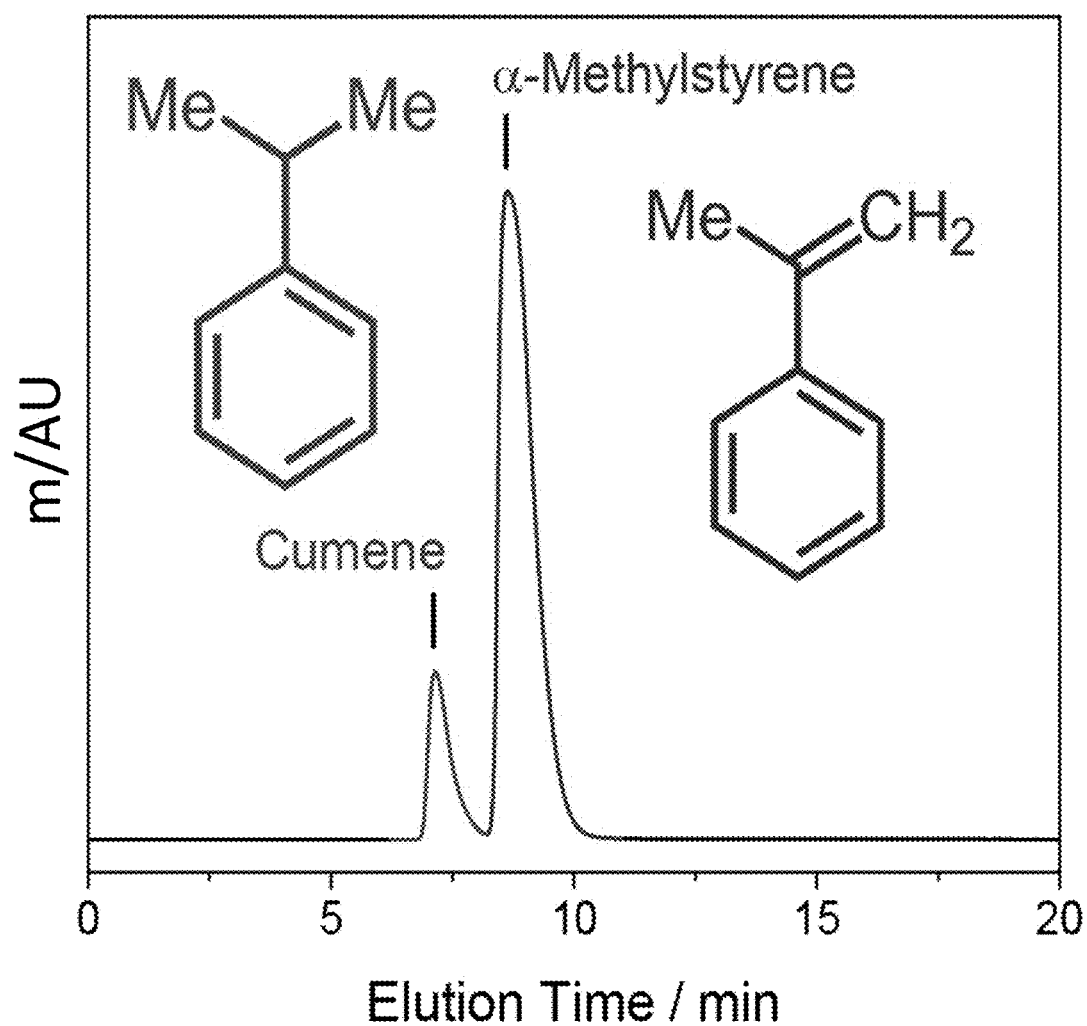
FIG. 4B depicts an exemplary bottom-up CD-MOF-1 column (particle size 10-15 μm) separations of a 10 μL sample of 50 mg $mL^{-1}$ cumene and a-methylstyrene mixture in HPLC-grade hexane at a flow rate of 1 mL $min^{-1}$ at 298 K.
Figure 4C:
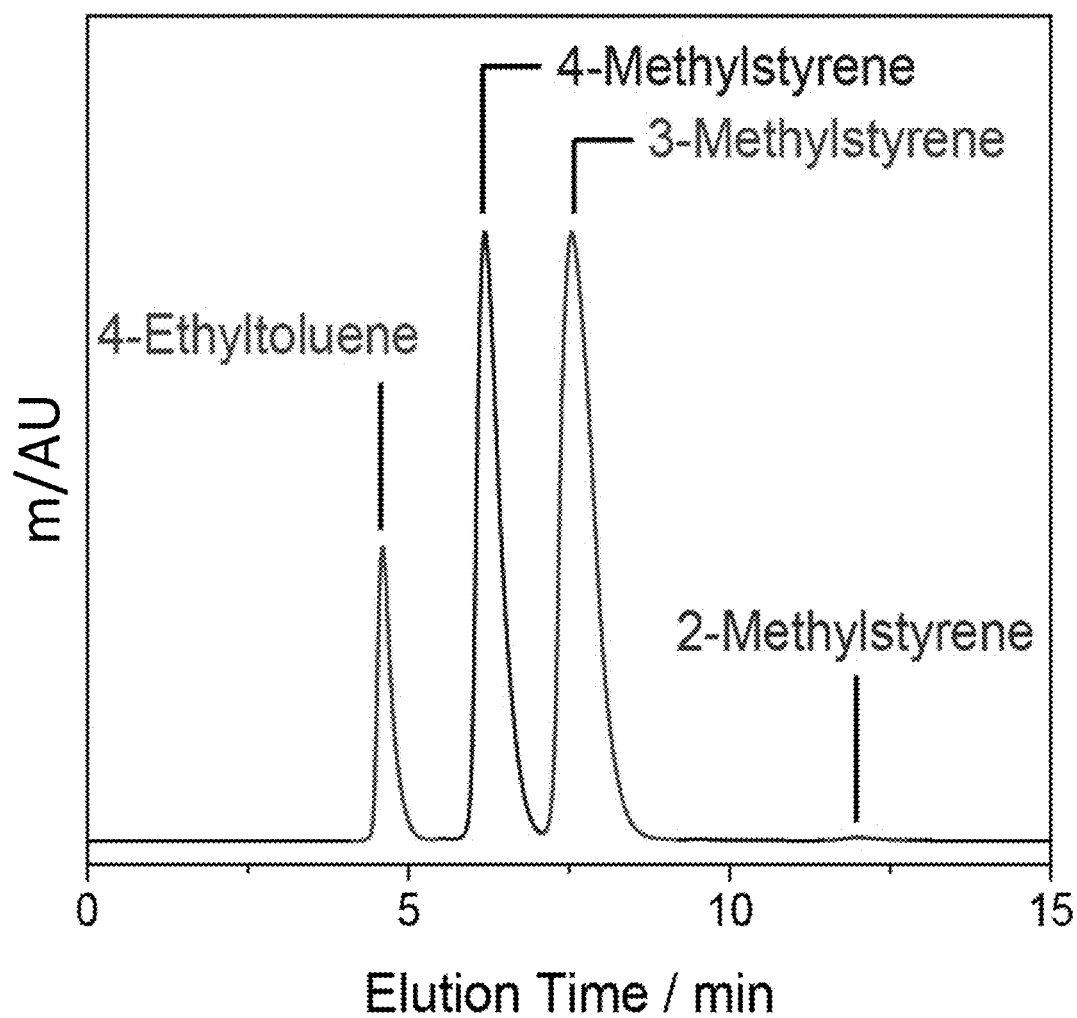
FIG. 4C depicts an exemplary bottom-up CD-MOF-1 column (particle size 10-15 μm) separations of a 10 μL sample of 50 mg $mL^{-1}$ mixture of 4-ethyltoluene, 2-methylstyrene (1%), 3-methylstyrene (60%) and 4-methylstyrene (40%) in HPLC-grade hexane at a flow rate of 1 mL $min^{-1}$ at 298 K.
Figure 4D:
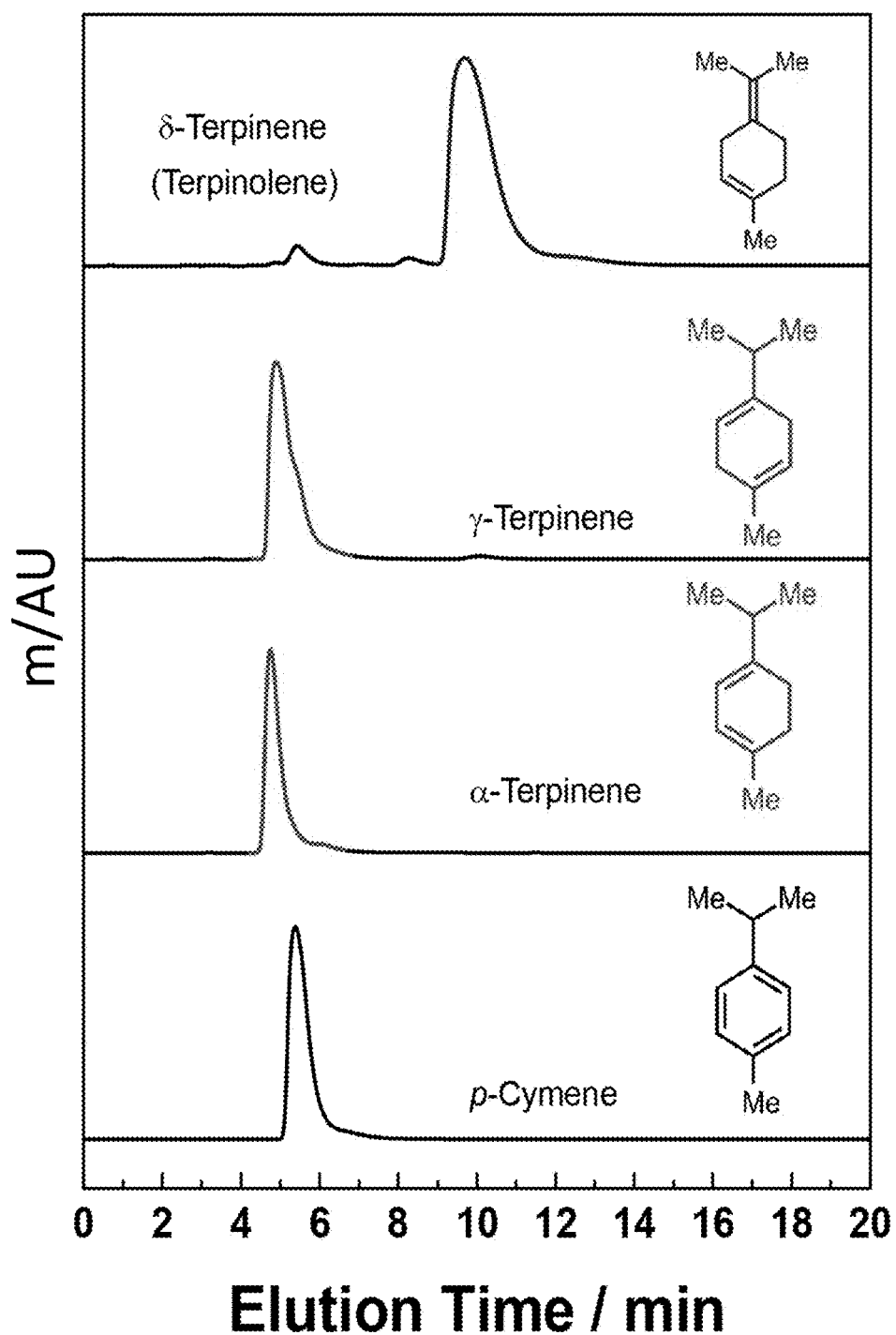
FIG. 4D depicts an exemplary bottom-up CD-MOF-1 column (particle size 10-15 μm) retention profiles of 10 μL samples of 50 mg $mL^{-1}$ of p-cymene and α-, β-, and δ-terpinenes in HPLC-grade hexane at a flow rate of 1 mL $min^{-1}$ at 298 K.
Figure 4E:
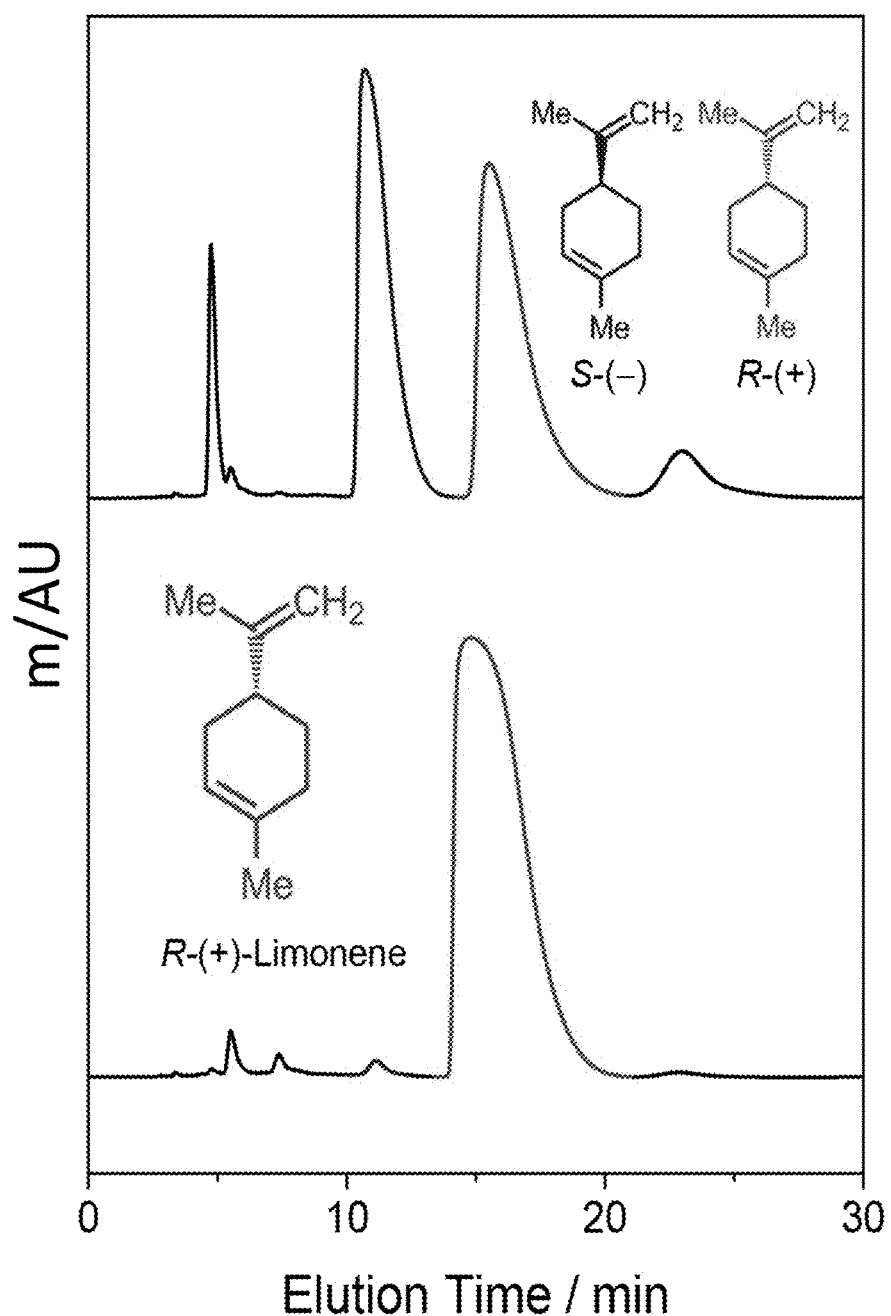
FIG. 4E depicts an exemplary bottom-up CD-MOF-1 column (particle size 10-15 μm) separation of 10 μL of 50 mg $mL^{-1}$ of a mixture of R- and S-enantiomer forms of limonene in HPLC-grade hexane at a flow rate of 1 mL $min^{-1}$ at 298 K.
Figure 4F:
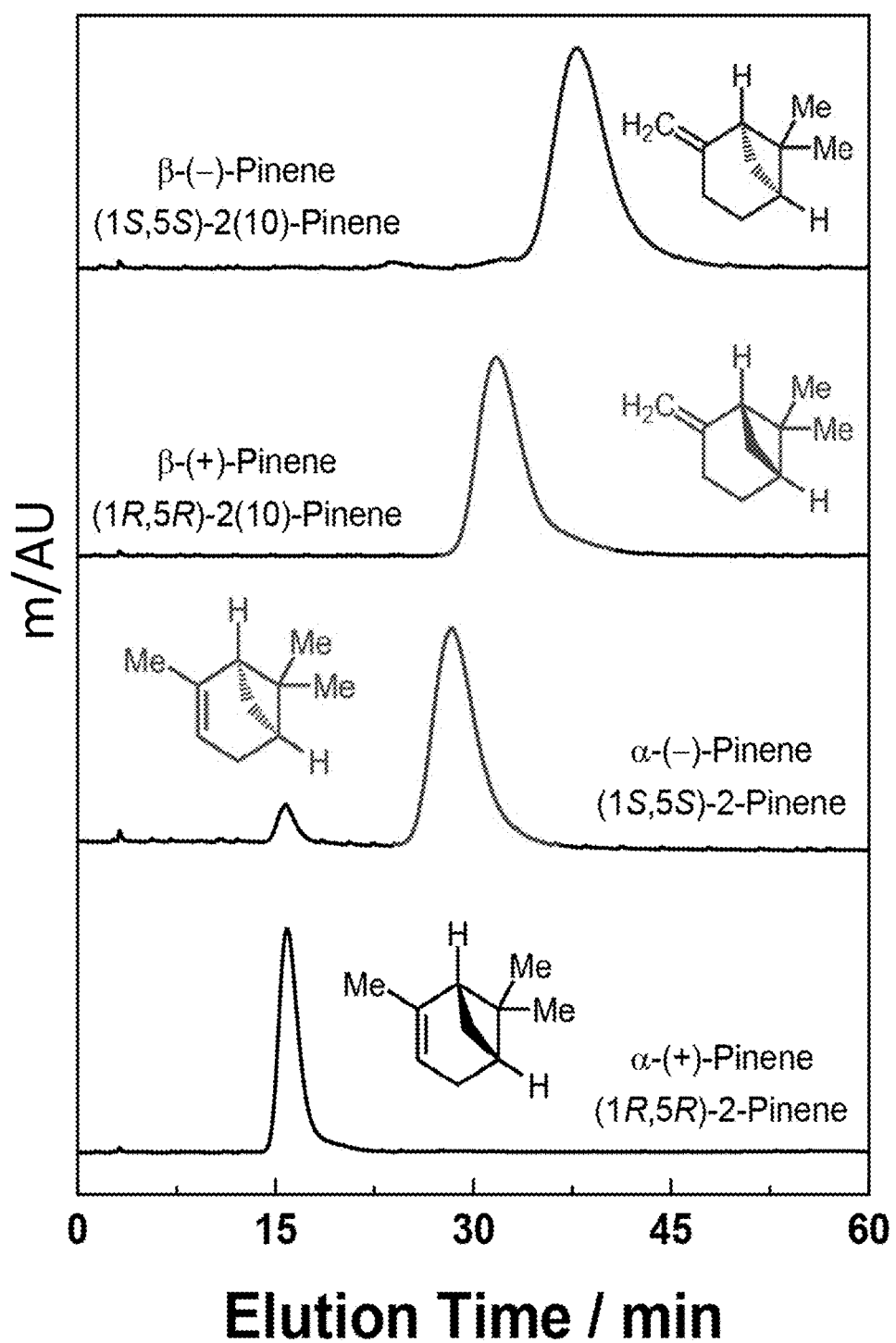
FIG. 4F depicts an exemplary bottom-up CD-MOF-1 column (particle size 10-15 μm) retention profiles of 5 μL samples of 50 mg $mL^{-1}$ of four configurational and enantiomer isomers of pinene ((1S,5S)-2(10)-Pinene; (1R, 5R)-2(10)-Pinene; (1S, 5S)-2-Pinene; (1R,5R)-2-Pinene) in HPLC-grade hexane at a flow rate of 1 mL $min^{-1}$ at 298 K.
Figure 5A:
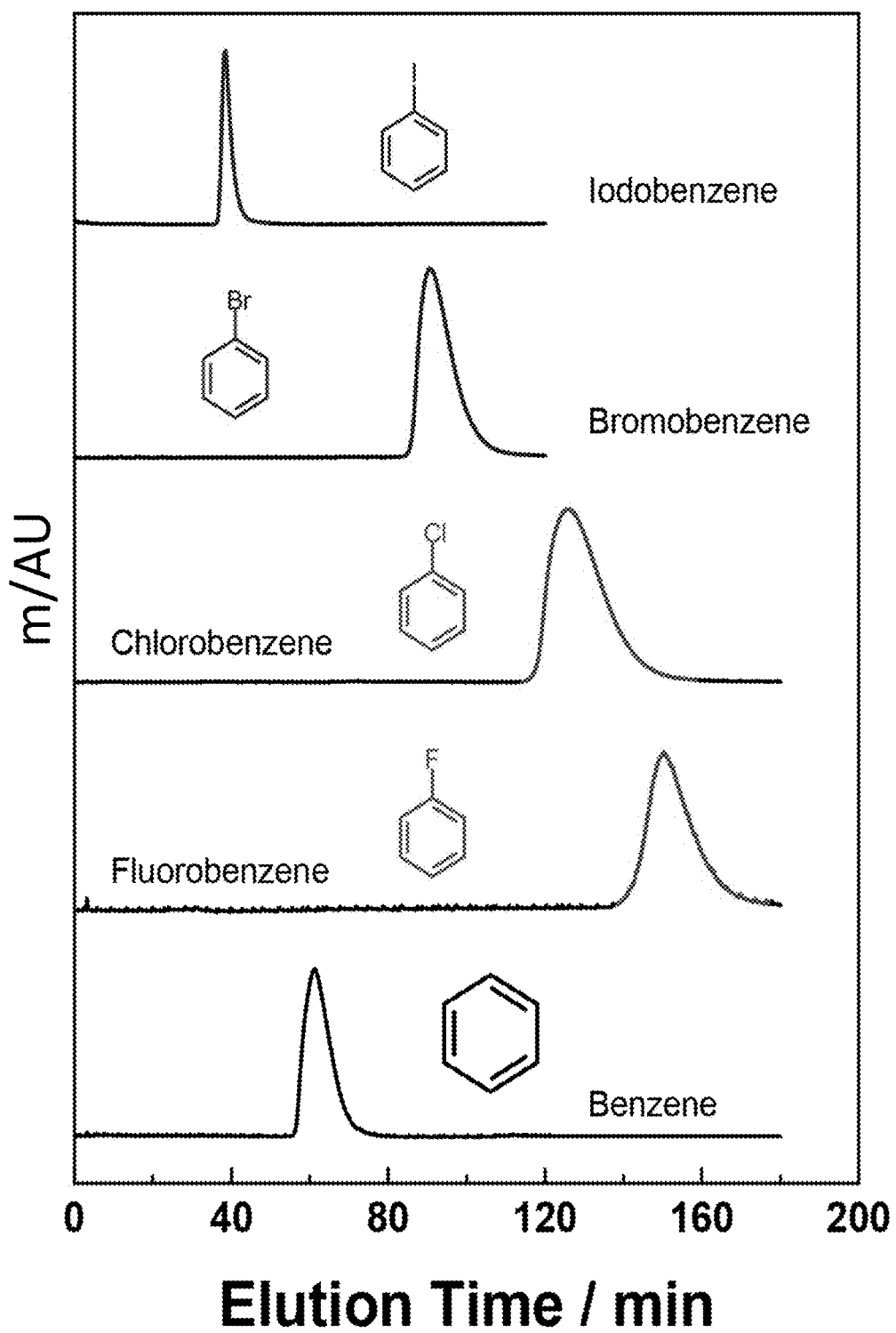
FIG. 5A depicts an exemplary bottom-up CD-MOF-1 column (particle size 10-15 μm) retention profiles of 5 μL samples of 50 mg $mL^{-1}$ of iodobenzene, bromobenzene, chlorobenzene, fluorobenzene and benzene in HPLC-grade hexane at a flow rate of 1 mL $min^{-1}$ at 298 K.
Figure 5B:
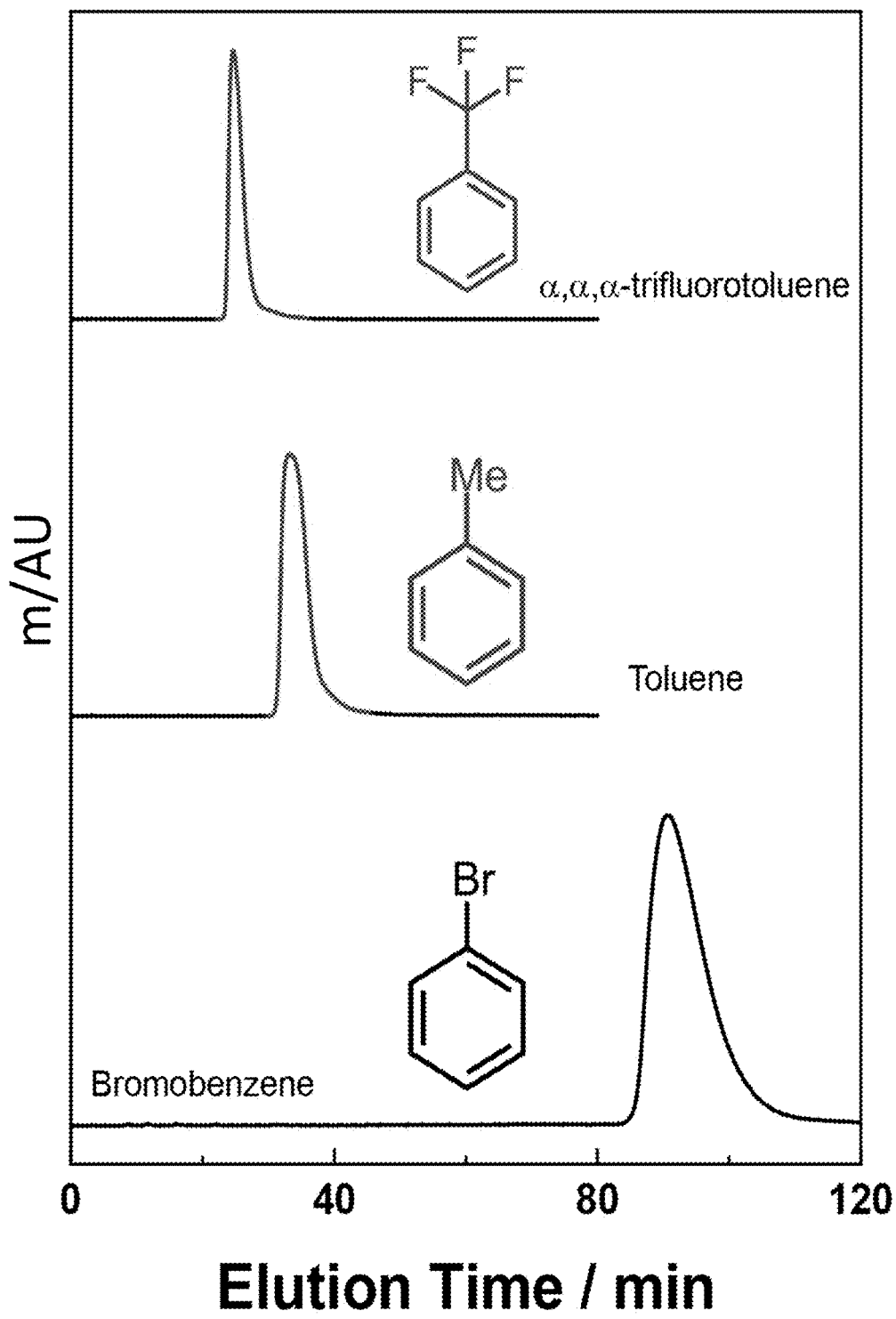
FIG. 5B depicts an exemplary bottom-up CD-MOF-1 column (particle size 10-15 μm) retention profiles of 5 μL samples of 50 mg $mL^{-1}$ of bromobenzene, toluene and α,α,α-trifluorotoluene in HPLC-grade hexane at a flow rate of 1 mL $min^{-1}$ at 298 K.
Figure 5C:
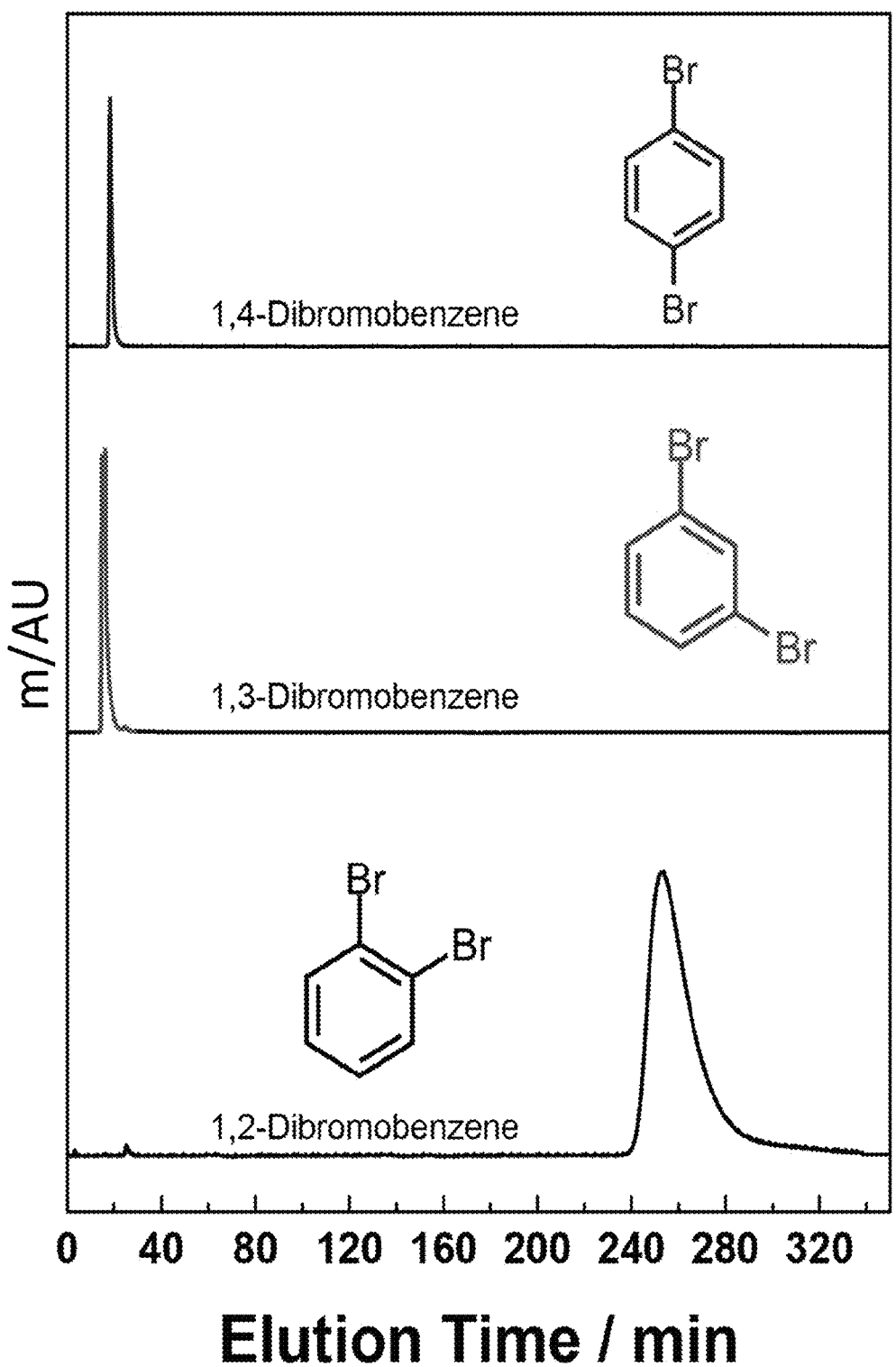
FIG. 5C depicts an exemplary bottom-up CD-MOF-1 column (particle size 10-15 μm) retention profiles of 5 μL samples of 50 mg $mL^{-1}$ of 1,3-dibromobenzene, 1,4-dibromobenzene and 1,2-dibromobenzene in HPLC-grade hexane at a flow rate of 1 mL min$^{-1}$ at 298 K.
Figure 5D:
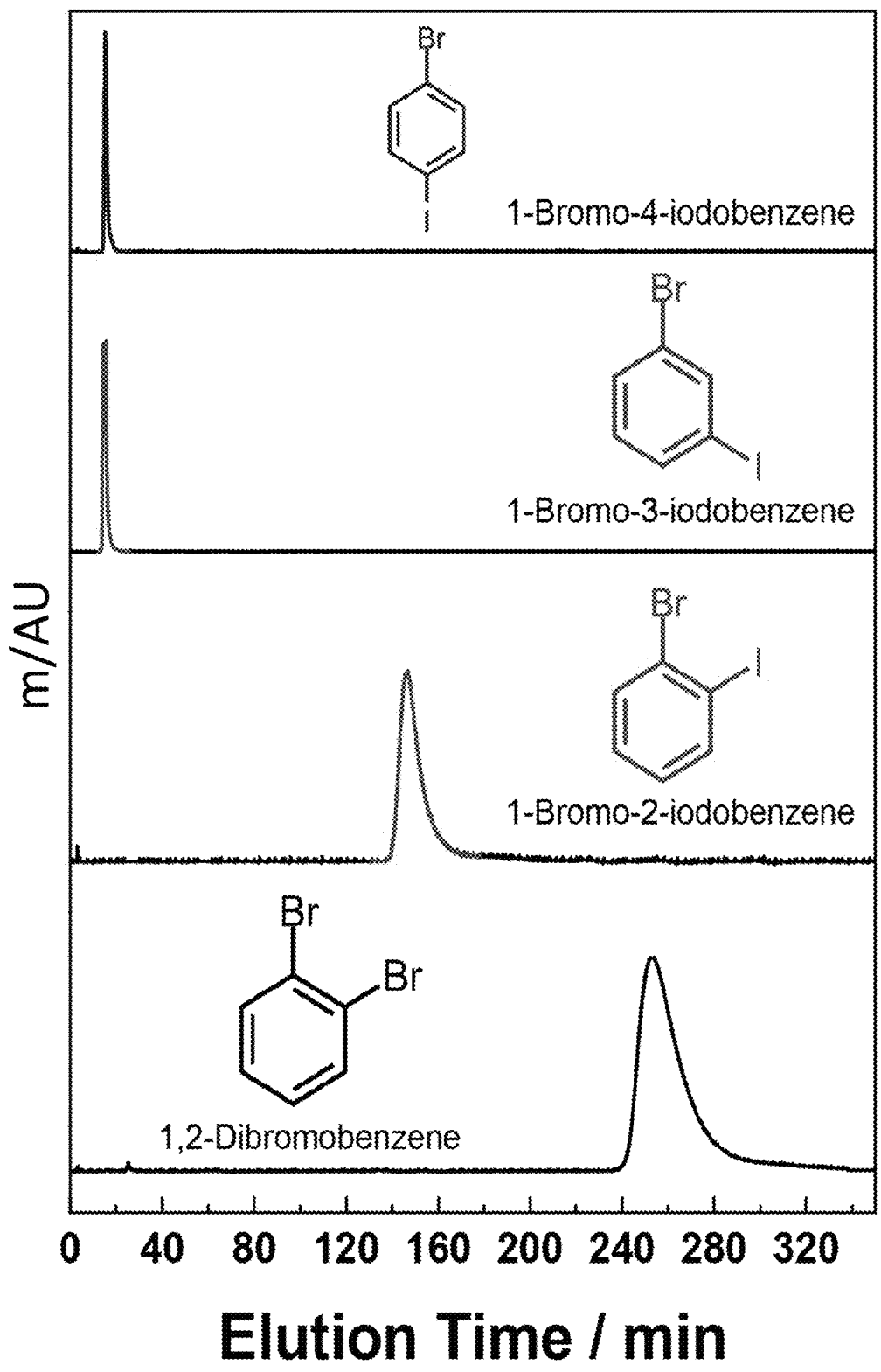
FIG. 5D depicts an exemplary bottom-up CD-MOF-1 column (particle size 10-15 µm) retention profiles of 5 µL samples of 50 mg mL$^{-1}$ of 1-bromo-4-iodobenzene, 1-bromo-3-iodobenzene, 1-bromo-2-iodobenzene and 1,2-dibromobenzene in HPLC-grade hexane at a flow rate of 1 mL min$^{-1}$ at 298 K.
Figure 5E:
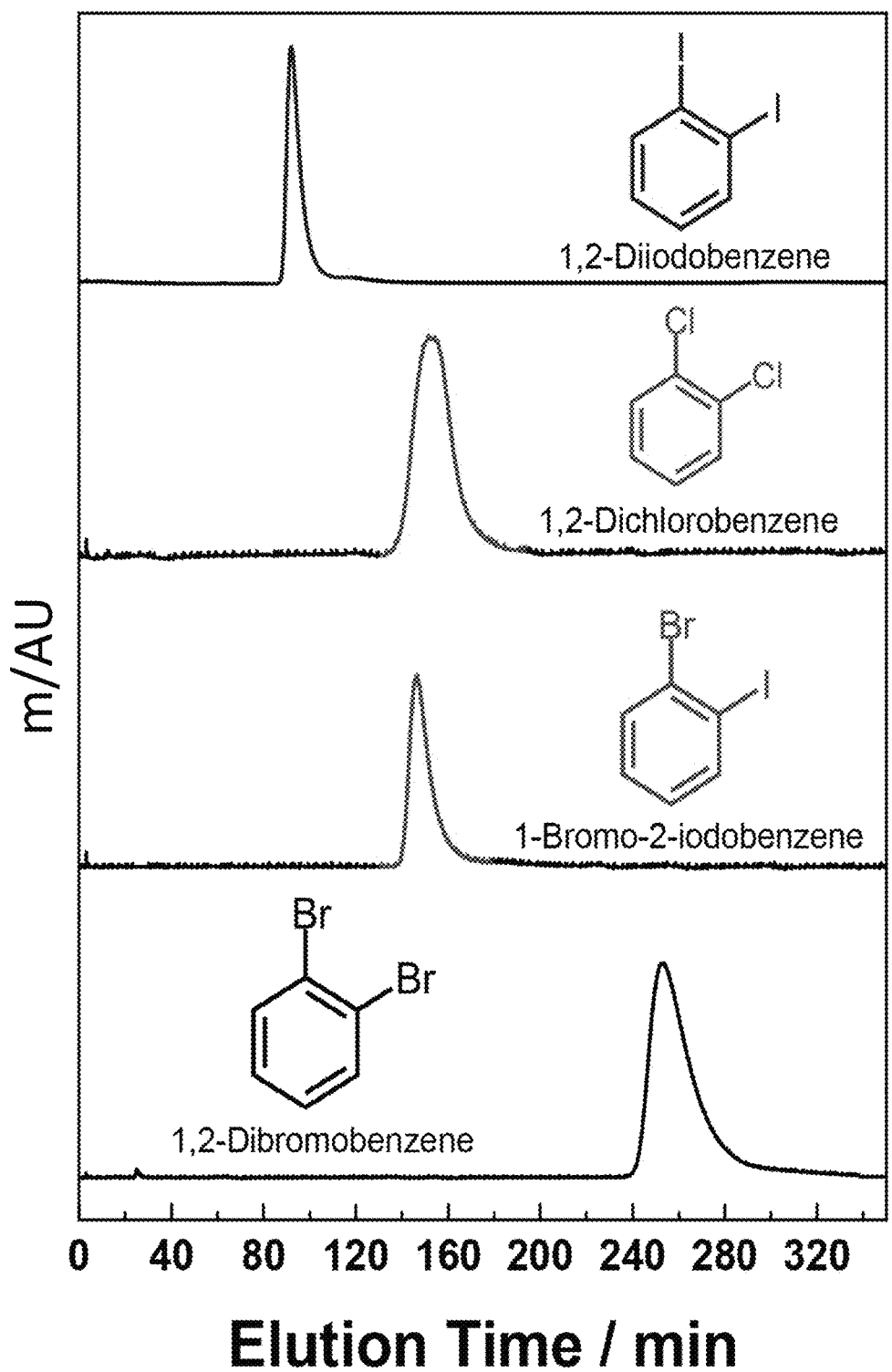
FIG. 5E depicts an exemplary bottom-up CD-MOF-1 column (particle size 10-15 µm) retention profiles of 5 µL samples of 50 mg mL$^{-1}$ of 1,2-diiodoobenzene, 1,2-dichorobenzene, 1-bromo-2-iodobenzene and 1,2-dibromobenzene in HPLC-grade hexane at a flow rate of 1 mL min$^{-1}$ at 298 K.

The foregoing experiment was repeated on a second bottom-up CD-MOF-1 column. Although similar results are observed for toluene and benzene, after flushing the column for 30 h with hexane, the retention time of ethylbenzene in the BTEX mixture is not influenced (FIG. 3C) by column activation. This observation suggests that MeOH originally occupy sites within the framework. After continued flushing with hexane, the MeOH is removed, and these sites become ideal for the retention of toluene and benzene. It would appear that these sites are too small to accommodate larger aromatic hydrocarbons, that is, those larger than and including ethyl-benzene. In order to test this theory of competitive binding of MeOH in sites within the CD-MOF-1 framework, the column was flushed with a mixture of hexane/isopropanol 98/2 v/v. The saturation of the framework with isopropanol results (FIG. 3E) in the deactivation of the column, with the retention times for benzene and toluene returning to those observed (FIG. 3A) for a freshly prepared column. The retention times of the xylene isomers and ethylbenzene, however, remain the same, indicating that the change in retention times for toluene and benzene is not a consequence of increasing the mobile phase polarity. The CD-MOF-1 column was flushed for 1 h with $CH_2Cl_2$ to remove $^i$PrOH from the framework, followed by priming the column with HPLC-grade hexane for 1 h. This procedure results in the full activation of the column and complete separation of BTEX mixtures (Table 4).

TABLE 4

Activated Bottom-Up CD-MOF Column Separation Factors of 50 mg mL$^{-1}$ BTEX Mixtures in HPLC-Grade Hexane at a Flow Rate of 1 mL min$^{-1}$.

| adsorbent | i | o-xylene | m-xylene | p-xylene | benzene | toluene | ethyl-benzene |
|---|---|---|---|---|---|---|---|
| CD-MOF-1 | o-xylene | — | 6.68 | 11.26 | 0.76 | 1.61 | 4.75 |
| Bottom-up | m-xylene | 0.15 | — | 1.69 | 0.11 | 0.24 | 0.71 |
| column | p-xylene | 0.09 | 0.59 | — | 0.07 | 0.14 | 0.42 |
|  | benzene | 1.32 | 8.82 | 14.88 | — | 2.13 | 6.27 |
|  | toluene | 0.62 | 4.14 | 6.98 | 0.47 | — | 2.94 |
|  | ethylbenzene | 0.21 | 1.41 | 2.37 | 0.21 | 0.34 | — |

Figure 2C:
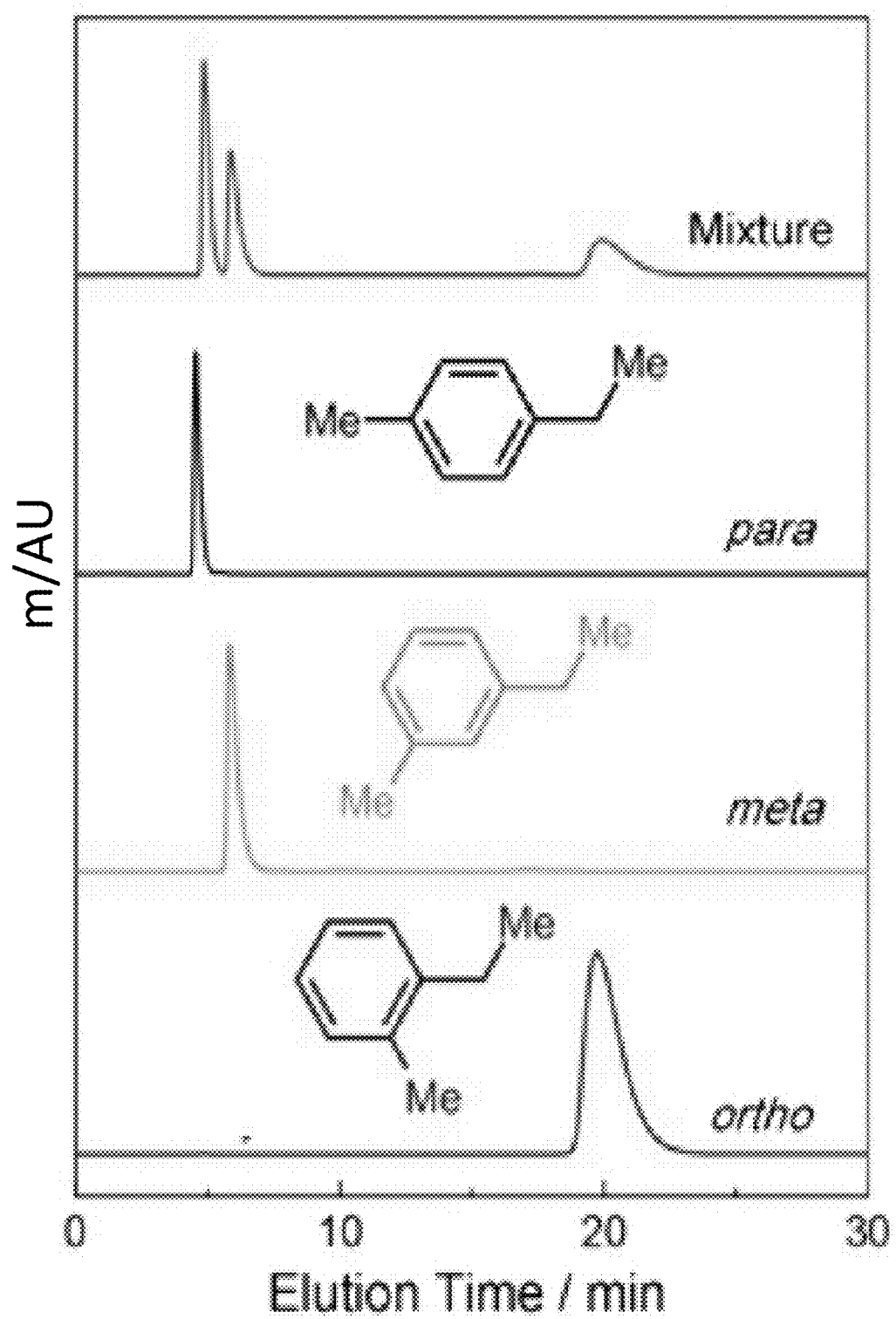
FIG. 2C depicts liquid-phase chromatographic separations of 50 mg $mL^{-1}$ ethyltoluene mixtures in HPLC-grade hexane at a flow rate of 1 mL $min^{-1}$ at 298 K using CD-MOFs as the stationary phase for an exemplary bottom-up CD-MOF-1 column (particle size 10-15 μm) where the separation profiles display the assignment of the elution order from the mixture (red) of ethyltoluene isomers, and pure-components of p- (black), m- (green), and o-ethyltoluene (blue).
Figure 2D:
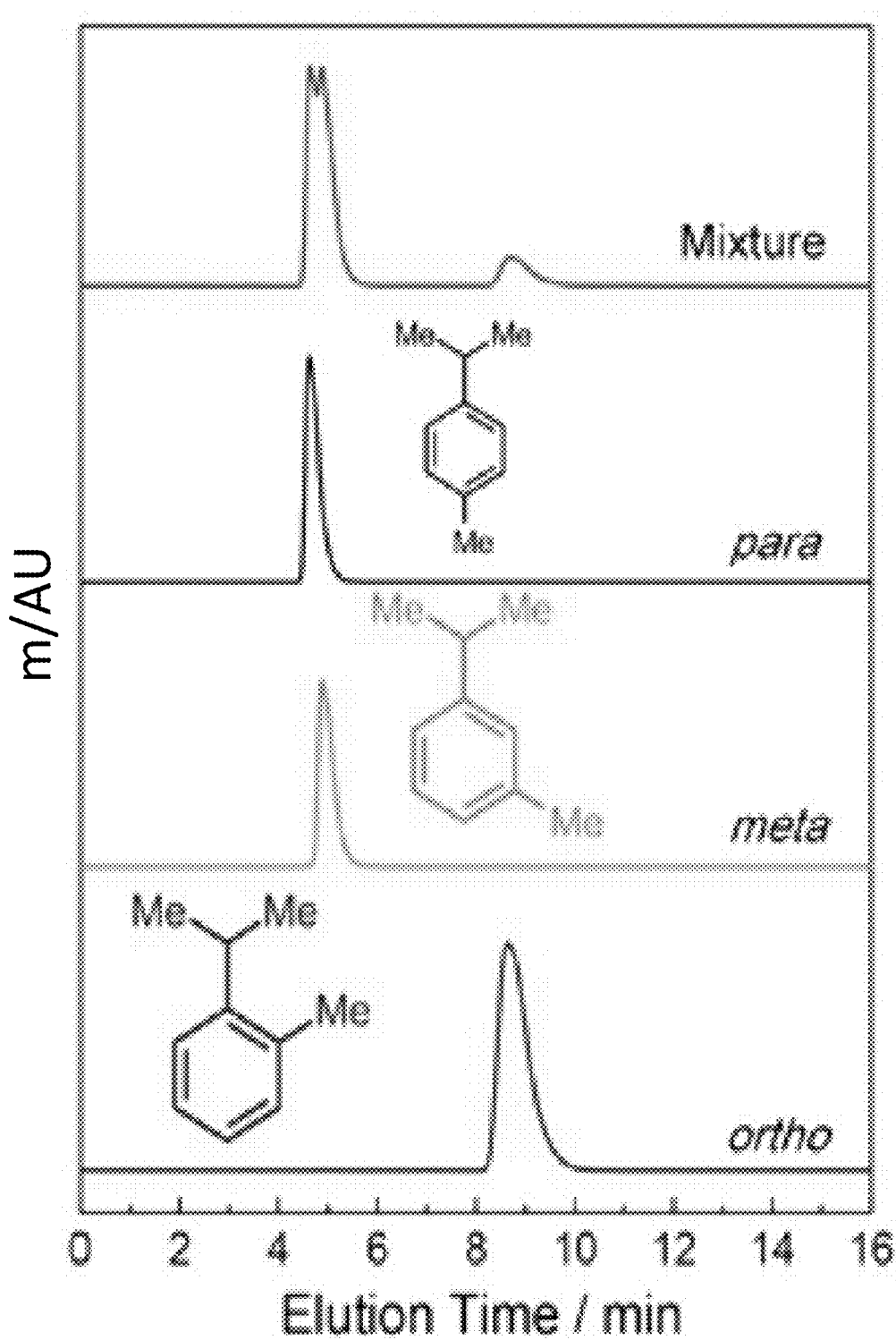
FIG. 2D depicts liquid-phase chromatographic separations of 50 mg $mL^{-1}$ cymene mixtures in HPLC-grade hexane at a flow rate of 1 mL $min^{-1}$ at 298 K using CD-MOFs as the stationary phase for an exemplary bottom-up CD-MOF-1 column (particle size 10-15 μm) where the separation profiles display the assignment of the elution order from the mixture (red) of cymene isomers, and pure-components of p- (black), m- (green), and o-cymene (blue).

The significant increase in retention times of small functionalized aromatics upon prolonged column usage is indicative of the removal of highly retained solvent (MeOH) within the CD-MOF-1 framework, allowing further adsorbate-adsorbent interactions. The emergence of this improved separation behavior, and the persistent ability of CD-MOF-1 to separate para-, meta-, and ortho-substituted compounds with consistent elution orders, is exemplified by the separation (FIG. 2C,D) of the regioisomers of both ethyltoluene and cymene. Here, we observe p-ethyltoluene to be the least retained isomer, followed by m-ethyltoluene, while o-ethyltoluene is highly retained with a comparable elution time to that of o-xylene. The bottom-up CD-MOF-1 column separates the ethyltoluene isomers with separation factors (Table 5), $\alpha_{3et4et}=2.10$, $\alpha_{2et4et}=13.8$, and $\alpha_{2et3et}=6.56$, similar to those observed for the xylene isomers. The separation (FIG. 2D) of the regioisomers of cymene highlights the extent of the ortho>>meta>para selectivity within the CD-MOF-1 framework. The selectivity order is consistent with that observed for the regioisomers of both xylene and ethyltoluene. CD-MOF-1 is capable of separating p- and m-cymene from o-cymene as a consequence of the high ortho selectivity observed within CD-MOFs. Baseline merging of the p- and m-cymene signals, however, suggests that the limit of the shape recognition of CD-MOF-1 has been reached as a consequence of the additional steric bulk in the cymene isomers.

TABLE 5

Bottom-up CD-MOF-1 column separation factors of 50 mg mL$^{-1}$ mixtures of p-, m-, and o-ethyltoluene in HPLC-grade hexane at 1 mL min$^{-1}$

| absorbent | solvent | i | p-ethyl-toluene | m-ethyl-toluene | o-ethyl-toluene |
|---|---|---|---|---|---|
| CD-MOF-1 | hexane | p-ethyltoluene | — | 0.47 | 0.07 |
| bottom-up |  | m-ethyltoluene | 2.10 | — | 0.15 |
| column |  | o-ethyltoluene | 13.77 | 6.56 | — |

The versatility of CD-MOF-1 as a stationary phase is highlighted (see Examples 4 and 5) by the purification of cumene from its impurities, n-propylbenzene and diisopropylbenzene, with separation factors $\alpha_{npropdiiso}=8.09$ and $\alpha_{cumenediiso}=7.12$ (Example 5).

Other exemplary separations of alkylaromatic compounds are presented in FIG. 4. The bottom-up CD-MOF HPLC procedure was capable of resolving ethylbenzene from styrene (FIG. 4A); cumene from α-methylstyrene (FIG. 4B), achieving complete resolution of a mixture of 4-ethyltoluene, 2-methylstyrene, 3-methylstyrene and 4-methyl styrene (FIG. 4C); the capability of separating δ-terpinene from a mixture comprising p-cymene and α-, β-, and δ-terpinenes (FIG. 4D); resolving a mixture of R- and S-enantiomer forms of limonene (FIG. 4E); and the capability of resolving the four configurational and enantiomer isomers of pinene ((1S,5S)-2(10)-Pinene; (1R,5R)-2(10)-Pinene; (1S,5S)-2-Pinene; (1R,5R)-2-Pinene) (FIG. 4F).

Exemplary separations of haloaromatic compounds are presented in FIG. 5. Referring to FIG. 5A, the bottom-up CD-MOF HPLC procedure is capable of resolving iodobenzene, bromobenzene, chlorobenzene, fluorobenzene and benzene with a retention order of benzene substituents being F>Cl>Br>H>I on the CD-MOF stationary phase. Despite H and F having similar effective Van der Waals radius, fluorobenzene elutes at 150 min compared with benzene elution profile at 60 min. The data suggests that strong halogen bonding exists between the framework and haloaromatic compound. Referring to FIG. 5B, the bottom-up CD-MOF HPLC procedure is capable of resolving bromobenzene, toluene and α,α,α-trifluorotoluene with a retention order of Br>CH$_3$>CF$_3$. Though halogen bonding exists between the framework and the haloaromatic compound, the influence of size matters among haloaromatic compounds in terms of their retention on the CD-MOF stationary medium. Referring to FIG. 5C, the bottom-up CD-MOF HPLC procedure is capable of resolving 1,3-dibromobenzene, 1,4-dibromobenzene and 1,2-dibromobenzene, where the retention time of elution being 16 min, 18 min and 240 min, respectively. Though 1,2-dibromobenzene and o-xylene have similar sizes, 1,2-dibromobenzene elutes 212 min after o-xylene. This result suggests that a combination of shape selectivity and strong halogen bonding interactions exist between 1,2-dibromobenzene and the CD-MOF contributes to the extended retention of 1,2-dibromobenzene to the CD-MOF stationary phase. Though certain mixed, dihaloaromatics can be resolved with the bottom-up CD-MOF HPLC procedure (see FIGS. 5D and 5E), no clear predictive rules emerged from the separation analysis.

Without the claimed subject matter of the invention being bound to, or otherwise limited in any manner by, any particular theory, the mechanism of retention of aromatic compounds with the CD-MOFs is based in part on a combination of electronic effects, shape selectivity, size and halogen bonding (if present) within the pores of γ-cyclodextrin molecules organized within the framework of the CD-MOF. The versatility of CD-MOFs as separation media was demonstrated by exploring the purification of other aromatic hydrocarbons, with the preference of the stationary phase for ortho>>meta>para retained in the separation of the regioisomers of both ethyltoluene and cymene. CD-MOFs are capable of separating p- and m- from o-cymene, with baseline merging of the p- and m-cymene signals, suggesting that the limit of the shape recognition of CD-MOFs has been reached. Breakthrough experiments contain a dynamic front at which component vapor pressures vary, resulting in nonequilibrium competitive adsorption; i.e., adsorption kinetics play a role in the separation of regioisomers. Diffusion along the pores is the rate determining mechanism for p-xylene vapor at low relative pressure, while m- and o-xylene adsorption is controlled by diffusion through a surface barrier. The variance in mechanisms of adsorption can be attributed to the smaller cross-sectional dimensions for p-xylene that enters the transverse pores parallel to the cyclodextrin ring more favorably. At high relative pressure, the mechanism changes to a linear driving force for all regioisomers, and diffusion through a surface barrier is the rate-determining process. The diffusion coefficients measured under static conditions, which follow the order p- >m- >o-xylene on the isotherm plateau, are consistent with breakthrough measurements. Molecular simulations suggest that the γ-cyclodextrin rings enable ortho selectivity primarily through favorable adsorbent-adsorbate interactions, and a highly efficient packing of the ortho isomer within the framework, which is confirmed by the adsorbate-adsorbate interactions from virial equation analysis of vapor adsorption isotherms. The larger size, and steric bulk of the cymene isomers most likely decrease their ability to adopt more favorable relative orientations, resulting in (i) weaker interactions within the framework, (ii) shorter retention times, and (iii) prevention of discrimination between p-, and m-cymene.

EXAMPLES

The invention will be more fully understood upon consideration of the following non-limiting examples, which are offered for purposes of illustration, not limitation.

Example 1

Materials and Methods

Potassium hydroxide, rubidium hydroxide hydrate, cetyltrimethylammonium bromide (CTAB) and MeOH were all purchased from Sigma Aldrich, while γ-cyclodextrin (γ-CD) was obtained from WACKER (CAVAMAX W8 PHARMA). All chemicals were used as received without further purification. CD-MOF-1 and CD-MOF-2 were prepared according to the literature procedures (Smaldone, R. A.; Forgan, R. S.; Furukawa, H.; Gassensmith, J. J.; Slawin, A. M. Z.; Yaghi, O. M.; Stoddart, J. F. *Angew. Chem. Int. Ed.* 2010, 49, 8630; Furukawa, Y.; Ishiwata, T.; Sugikawa, K.; Kokado, K.; Sada, K. *Angew. Chem. Int. Ed.* 2012, 51, 10566). Particle size control experiments on CD-MOF-1 were undertaken using a modified protocol from the literature (Furukawa, Y.; Ishiwata, T.; Sugikawa, K.; Kokado, K.; Sada, K. *Angew. Chem. Int. Ed.* 2012, 51, 10566). Large CD-MOF-2 crystals were harvested and ground using a KRUPS type F203 blender prior to grinding with a pestle and mortar. The ground particles were sieved under an atmosphere of nitrogen through Gilson Company Inc. membrane sieves, #170, #230 and #400, to obtain final particle sizes between 10-37 μm that were unable to pass through a 10 μm sieve. Optical microscope (OM) images for CD-MOF-1 size-controlled particles and CD-MOF-2 particles after grinding were obtained using an Olympus BX53 microscope with an Olympus DP25-mounted camera. Scanning electron microscopy (SEM) images were collected on a Hitachi S-3400N-II variable pressure SEM, with a tungsten filament and ESED II detector.

Samples used for SEM images were suspended in MeOH and diluted to 1 mg mL$^{-1}$ using serial dilutions before deposition onto a carbon tape. The samples were then dried under vacuum for 30 min before imaging them at 30 kV under high vacuum. Powder X-ray diffraction patterns of CD-MOF-1 and CD-MOF-2 were collected on a Bruker AXS APEX2 diffractometer, equipped with a CCD detector and a CuKα IμS microfocus source with MX optics. Data were collected with an area detector as rotation frames over 180° in φ at 2θ values of 12 and 24° and exposed for 10 min for each frame. At a distance of 150 mm, the detector area covers 24° in 2θ. Overlapping sections of data were matched and the resulting pattern integrated using the Bruker APEX2 Phase ID program. Powder pattern data were treated for amorphous background scatter. HPLC was carried out using a Shimadzu analytical normal-phase HPLC, equipped with a Shimadzu SIL-20A HT prominence auto-sampler, SPD-M20A prominence diode array detector, LC-20AB prominence LC and a DGU-20A3 degasser. The normal phase HPLC was fitted with CD-MOF packed columns with dimensions 250 mm length, 4.6 mm internal diameter x¼" outer diameter. Unless otherwise stated, chromatography was carried out using HPLC grade hexane as the mobile phase at a flow rate of 1 mL min$^{-1}$, with 10 μL injection volumes of 50 mg mL$^{-1}$ solutions. Breakthrough experiments were carried out in a 4-mm glass U-tube with CD-MOF-2 crystals. CD-MOF-2 (1.46 g) was used in order to fill the tube at a length of 16 cm. The sample was purged with dry $N_2$ at 60° C. overnight to ensure the complete activation of the sample prior to breakthrough measurements. Dry $N_2$ at a rate of 20 mL/min was bubbled through a mixture of the xylene isomers (15 mL each) at atmospheric pressure. The effluent was passed through a VICI Valco 6-way sampling valve. An aliquot (0.25 mL) of gas was sampled every 5 min and delivered to a Perkin Elmer Clarus 500 Gas Chromatograph fitted with a Supelco SCOT capillary GC column (Sigma-Aldrich 23813-U, 50 ft long, 0.02 in. outside diameter) maintained at 90° C. The analyses were performed using an injector and detector (FID) temperature of 220° C. and $N_2$ was used as the carrier gas that was maintained at an inlet pressure of 1.5 psi with a split ratio of 10:1. Baseline separation of the xylene isomers was achieved and all peaks were easily integrated in the resulting GC trace. Single component gas adsorption isotherms were conducted on an IGA gravimetric analyser (Hiden Isochema, IGA-001, Warrington, UK). The analyzer is an ultra-high vacuum (UHV) one comprising of a computer controlled microbalance with both pressure and temperature regulation systems. The microbalance had a long-term stability of ±1 μg with a weighing resolution of 0.2 μg. The CD-MOF-2 sample was outgassed for 12 h until a constant weight was achieved, at <10$^{-6}$ Pa, at 333 K prior to adsorption measurements. The pressure transducers had ranges of 0-2, 2-100 and 100-1000 mbar. Vapor sorption isotherms were obtained using a circulating water-ethylene glycol bath controlled by a computer using IGA software. The xylene regioisomers used to generate the vapor for the isotherm measurements were degassed fully by repeated evacuation and equilibration cycles of the vapor reservoir. The vapor pressure was gradually increased to the desired value during ~30 s in order to prevent disruption of the microbalance. It follows that the period during which the pressure change occurs is small when compared with the adsorption kinetics, allowing isotherm adsorption kinetics to be obtained for each pressure step. The sample temperature was obtained using a thermocouple located 5 mm from the sample. The pressure set point was maintained by computer control throughout the duration of the experiment.

Example 2

Synthetic Protocols

The extended metal-organic frameworks, CD-MOF-1 and CD-MOF-2, were prepared according to literature procedures (Smaldone, R. A.; Forgan, R. S.; Furukawa, H.; Gassensmith, J. J.; Slawin, A. M. Z.; Yaghi, O. M.; Stoddart, J. F. *Angew. Chem. Int. Ed.* 2010, 49, 8630; Furukawa, Y.; Ishiwata, T.; Sugikawa, K.; Kokado, K.; Sada, K. *Angew. Chem. Int. Ed.* 2012, 51, 10566).

2.1. Synthesis of CD-MOF Analogs

CD-MOF-1: γ-CD (1.30 g, 1 mmol) and KOH (0.45 g, 8 mmol) were dissolved in $H_2O$ (20 mL). The solution was filtered through a 45-μm syringe filter and decanted into separate vials. MeOH was allowed to diffuse slowly into the solution over a period of a week.

CD-MOF-2: γ-CD (1.30 g, 1 mmol) and RbOH (0.82 g, 8 mmol) were dissolved in $H_2O$ (20 mL). The solution was filtered through a 45-μm syringe filter and decanted into separate vials. MeOH was allowed to diffuse slowly into the solution over a period of a week.

2.2. Particle Preparation and Activation

The crystals were harvested and crushed to sizes of approximately 100-500 μm. The crystals were filtered and washed with MeOH (4×50 mL) under vacuum. Additional washing with $CH_2Cl_2$ (3×50 mL) was carried out to remove the excess of MeOH. The crystals were then left to vacuum dry for 12 h. The crystals were transferred to a $N_2$ glove box where they were finely ground using a KRUPS type F203 blender, prior to being ground further using a pestle and mortar. The resulting particles were sieved through Gilson Company Inc. membrane sieves, #170, #230 and #400 with repeated grinding between sieving through each membrane to ensure particles smaller than 37 μm were attained. The milled CD-MOF-2 particles were checked for crystallinity and structural integrity using powder X-ray crystallography before being dry loaded or slurry loaded using any non-aqueous solvent into the column (SI B4).

2.3. Particle Size Control Synthesis of CD-MOF-1

CD-MOF-1 was synthesized using a modified literature procedure (Furukawa, Y.; Ishiwata, T.; Sugikawa, K.; Kokado, K.; Sada, K. *Angew. Chem. Int. Ed.* 2012, 51, 10566).

CD-MOF-1-Micro: γ-CD (8.15 g, 6.2 mmol) and KOH (2.8 g, 49.7 mmol) were dissolved in $H_2O$ (250 mL). The solution was filtered through a 45-μm syringe filter and decanted into separate vials (5 mL in each vial). MeOH was allowed to diffuse slowly into the solutions for 24 h. Each solution was decanted into a fresh vial before cetyltrimethylammonium bromide (CTAB) was added, and after the complete dissolution of CTAB, MeOH was diffused into the solution for an additional 24 h. The solutions were combined together, and centrifuged at 5000 rpm for 10 min before the supernatant was removed and replaced with MeOH. This process was repeated five times in order to ensure CTAB was completely removed from the sample.

Varying the amount of CTAB during the synthesis of CD-MOF-1 can be used to control the size of the CD-MOF-1 particles as confirmed (Table 1) by optical microscopy and SEM. The size of the CD-MOF-1 particles is utilized in this system to control the elution times of the aliphatic and aromatic compounds by optimizing packing conditions to prevent the bypassing of the solid phase.

The particle size modified column was prepared using CD-MOF-1-Micro-2, where CTAB (40 mg) was added to the reaction mixture after the first incubation period. This protocol facilitated the formation of CD-MOF-1 crystallites of 10-15 μm.

2.4. HPLC Column Loading

HPLC was carried out using a Shimadzu analytical normal-phase HPLC, fitted with a CD-MOF packed column with dimensions 250 mm in length and 4.6 mm internal diameter and ¼" outer diameter. Chromatography was carried out using HPLC-grade hexane as the mobile phase at a flow rate of 1 mL min$^{-1}$, with 10 μL injection volumes of 50 mg mL$^{-1}$ solutions, unless otherwise stated. The CD-MOF particles were checked for their crystallinity and structural integrity using powder X-ray crystallography before being packed into the column. The blended CD-MOF-2 particles can be dry loaded or slurry loaded—using any non-aqueous solvent—into the column, whilst the 10-15 μm particles of CD-MOF-1 were slurry loaded using a non-aqueous solvent.

Example 3

Spectroscopic Characterization of CD-MOF Samples 3.1. Optical Microscopy (OM)

Optical Microscope (OM) images were obtained using an Olympus BX53 microscope with an Olympus DP25-mounted camera.

3.1.1. CD-MOF-2 Particles

Figure 6:
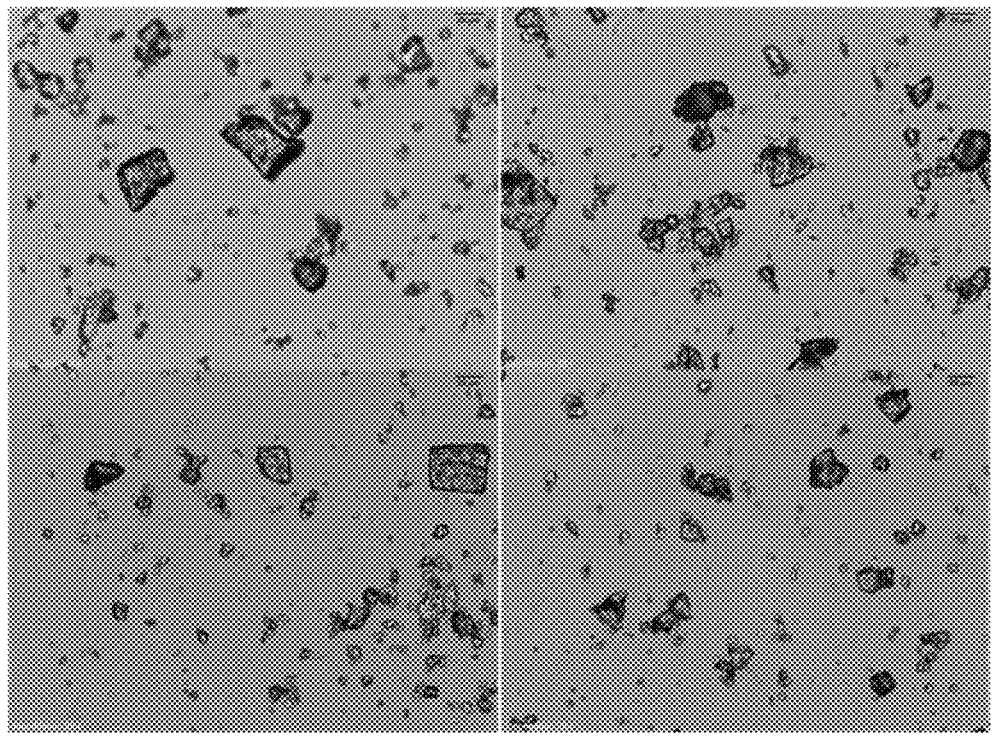
FIG. 6 depicts CD-MOF-2 particles viewed under an optical microscope at ×25 magnification after fine grinding, prior to packing the top-down HPLC column.
Figure 7A:
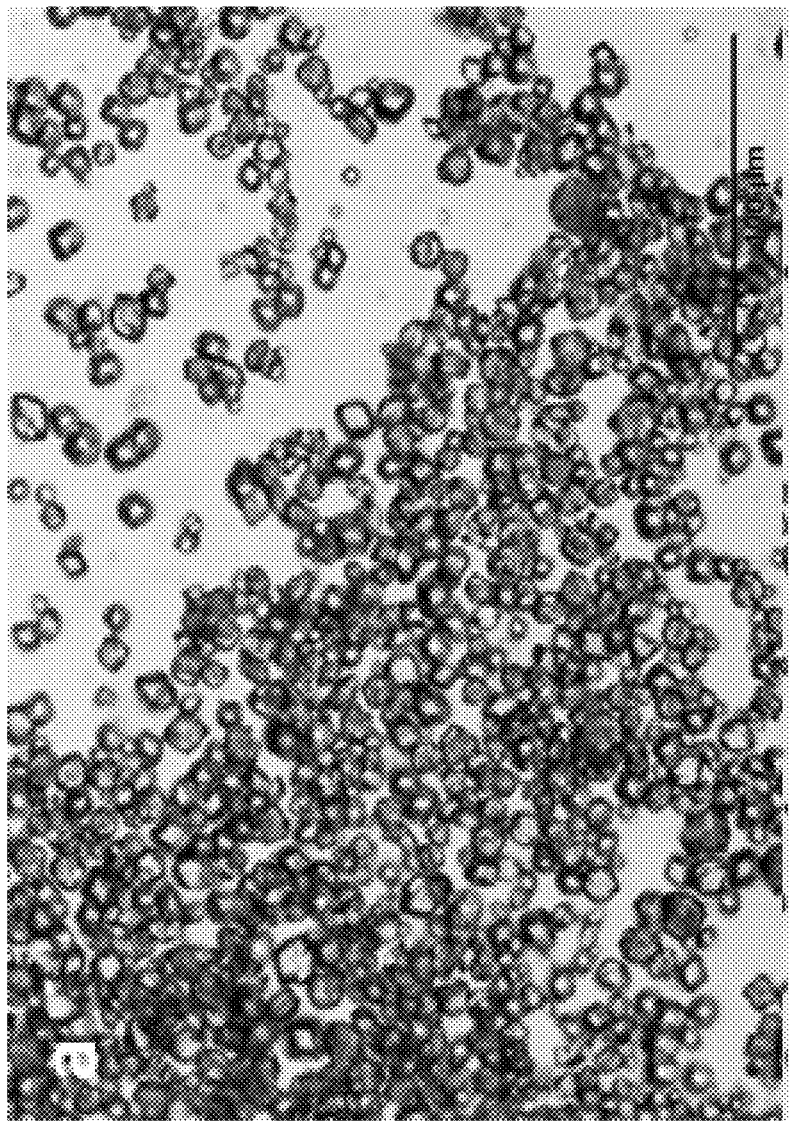
FIG. 7A depicts optical micrographs of CD-MOF-1 particles crystallized in the presence of 20 mg of CTAB.
Figure 7B:
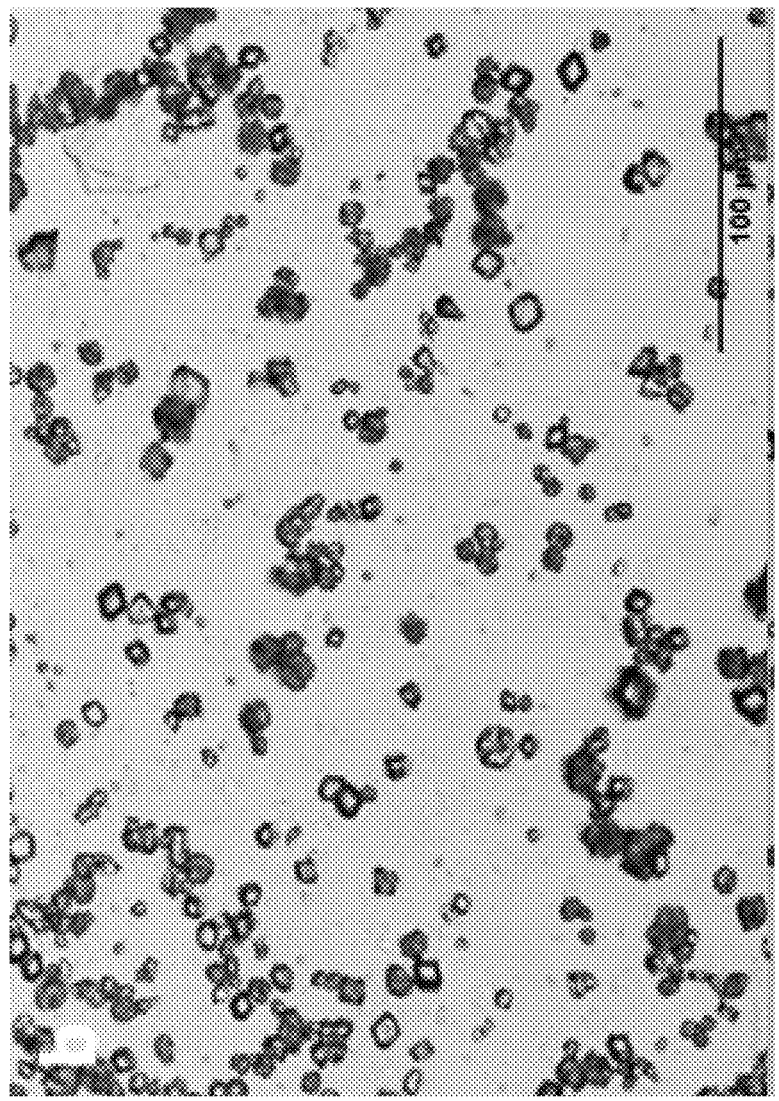
FIG. 7B depicts optical micrographs of CD-MOF-1 particles crystallized in the presence of 40 mg of CTAB.
Figure 7C:
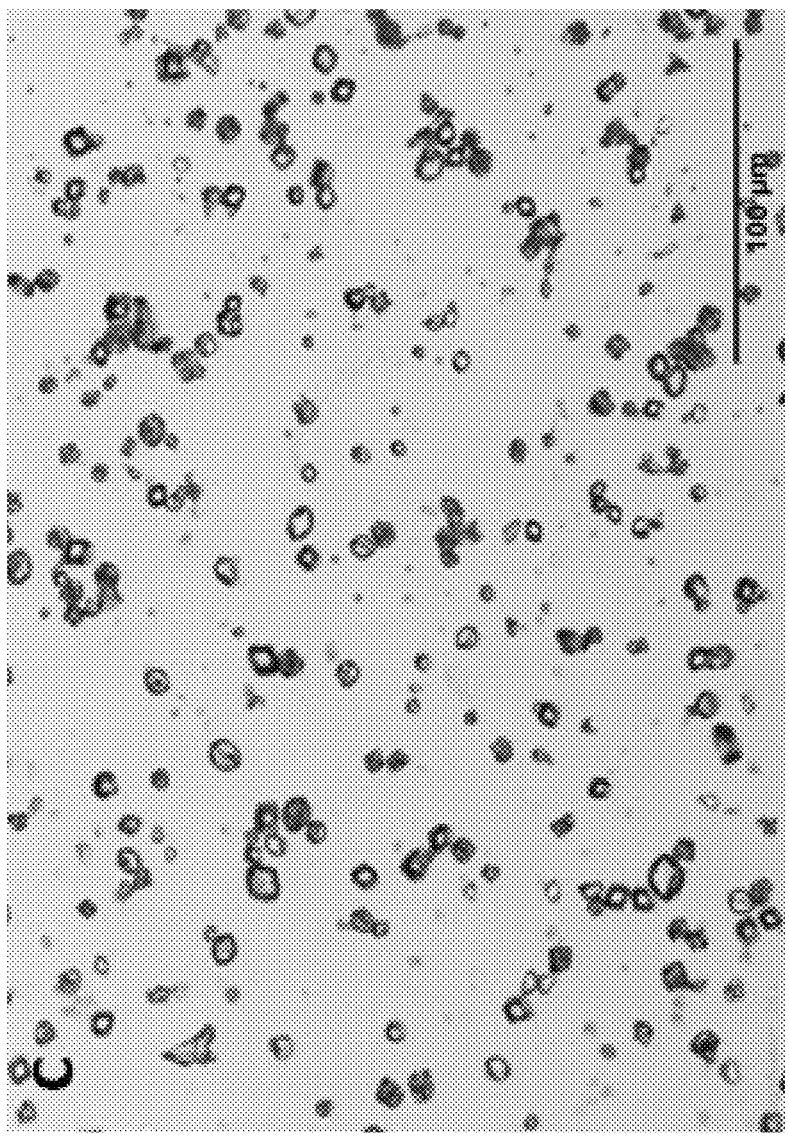
FIG. 7C depicts optical micrographs of CD-MOF-1 particles crystallized in the presence of 60 mg of CTAB.
Figure 7D:
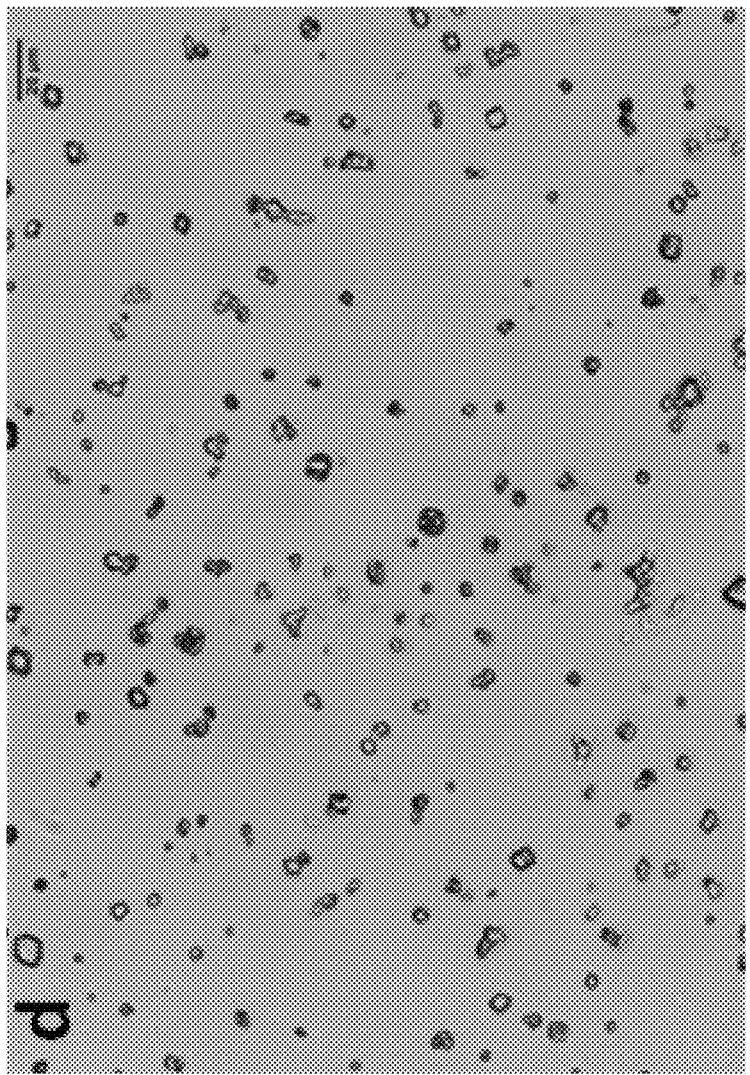
FIG. 7D depicts optical micrographs of CD-MOF-1 particles crystallized in the presence of 80 mg of CTAB.
Figure 8A:
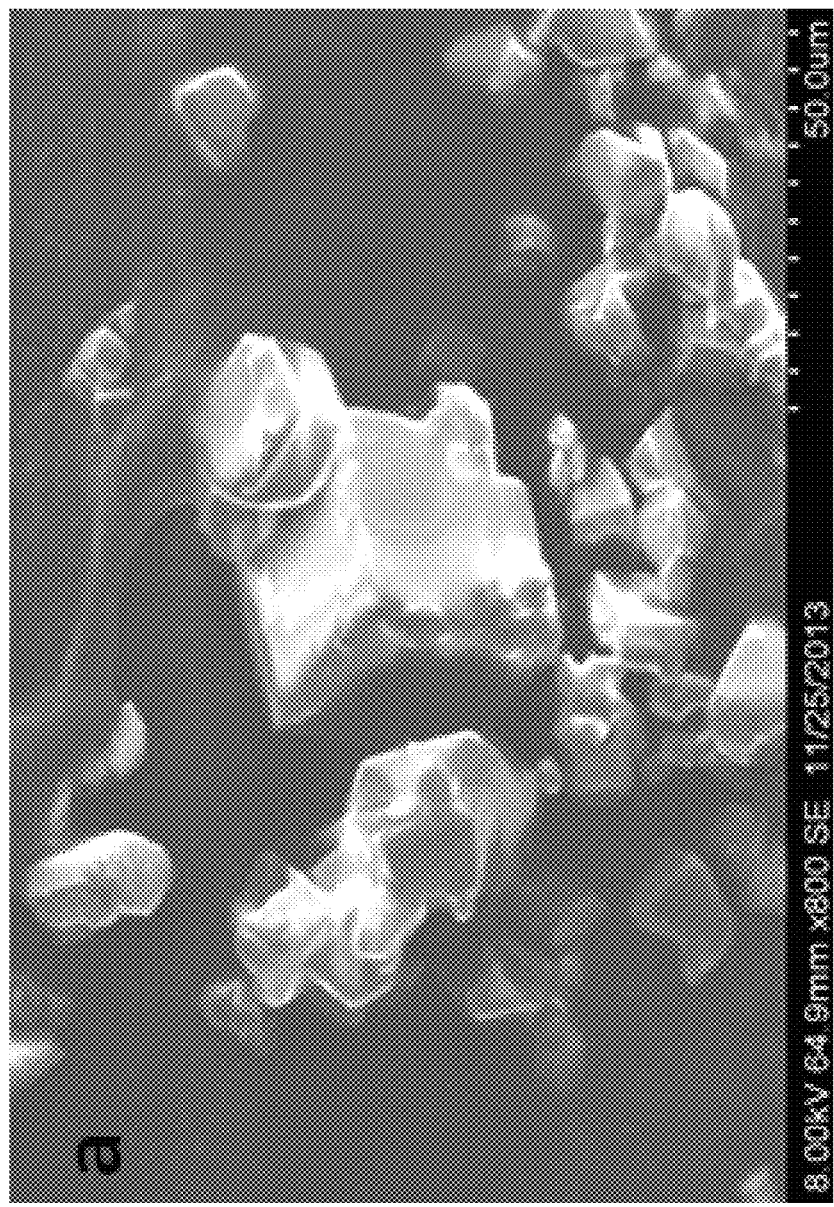
FIG. 8A depicts SEM images of CD-MOF-1 particles crystallized in the presence of 20 mg of CTAB.
Figure 8B:
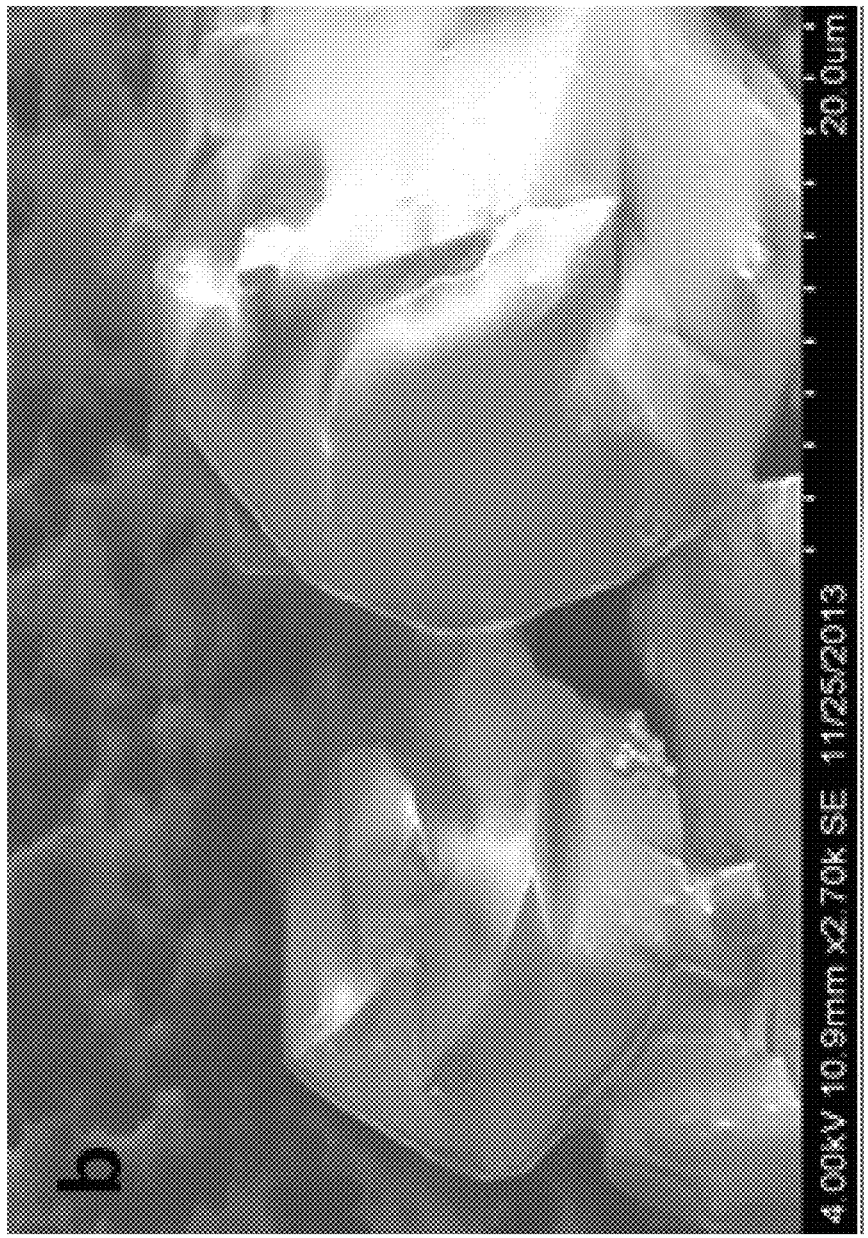
FIG. 8B depicts SEM images of CD-MOF-1 particles crystallized in the presence of 40 mg of CTAB.
Figure 8C:
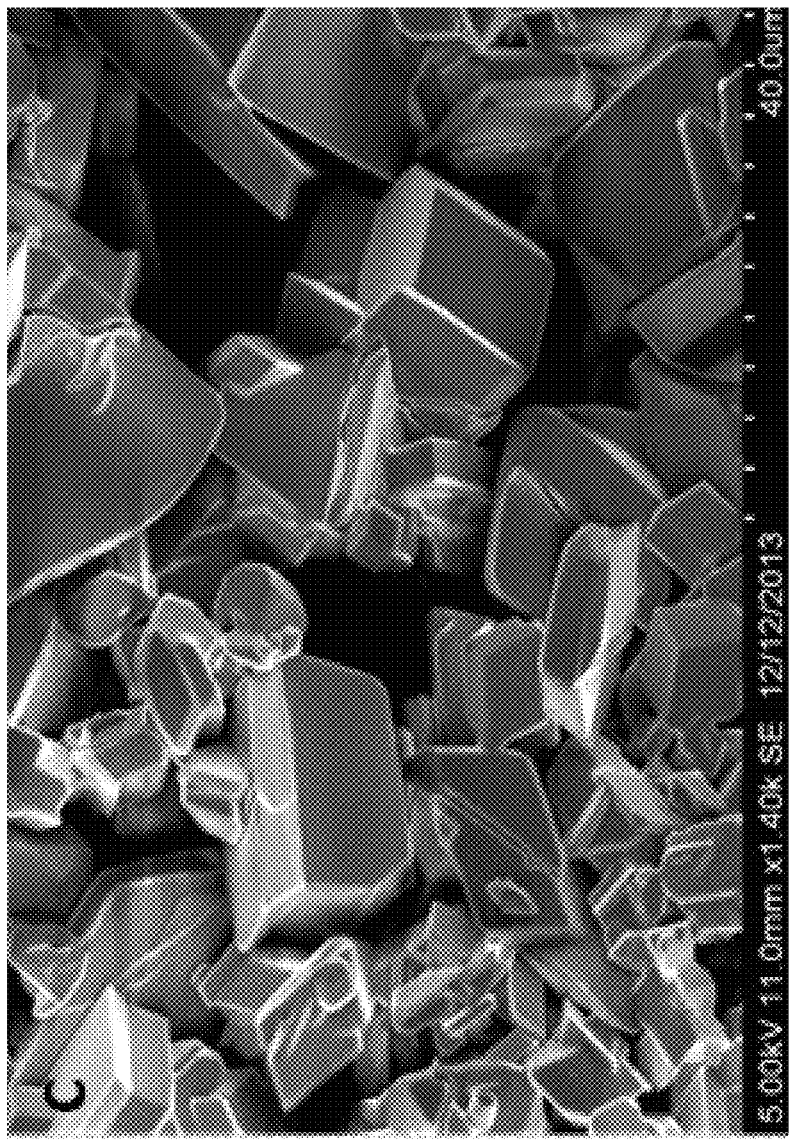
FIG. 8C depicts SEM images of CD-MOF-1 particles crystallized in the presence of 60 mg of CTAB.
Figure 8D:
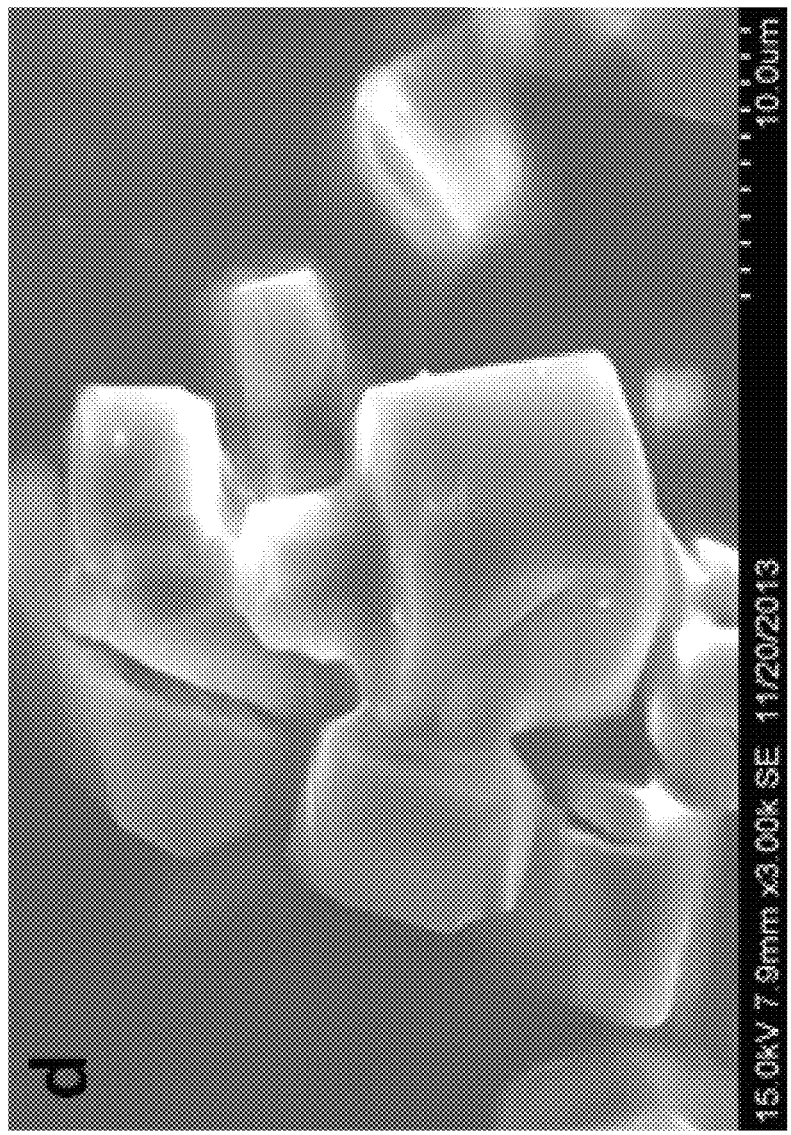
FIG. 8D depicts SEM images of CD-MOF-1 particles crystallized in the presence of 80 mg of CTAB.

Particle images were analyzed using optical microscopy in order to determine particle size and shape distributions. In an effort to prevent degradation of the particles by solvent loss, they were mounted onto glass slides using paratone oil. The images of CD-MOF-2 particles employed in the top-down column investigations are illustrated under an optical microscope in FIG. 6. We believe the variation in particle shape and size arising from the grinding phases is the primary reason for inefficient particle packing, resulting in poor separations.

The particles of CD-MOF-2 observed under an optical microscope have irregular shapes and sizes, ranging from 0.5-37 μm in cross section. Although the observed CD-MOF-2 particles were fragmented, they remained crystalline as confirmed visually using plane polarized light under an optical microscope while their bulk crystallinity was established using powder X-ray diffraction techniques.

3.1.2. CD-MOF-1 Particles

Optical microscopy (FIG. 7) and SEM (FIG. 8) were used to monitor the size distributions of CD-MOF-1 crystallizations with CTAB.

CD-MOF-1 Crystallizations with CTAB, monitored by optical microscopy, highlight the consistent formation of regular cubic-shaped CD-MOF-1 particles with size distributions at varying concentrations of CTAB recorded in Table 1. Confirmation of the size variation ranges was gained using SEM imaging techniques to measure the cross sections of the CD-MOF-1 particles.

3.2. Scanning Electron Microscopy (SEM)

SEM Images were collected on a Hitachi S-3400N-II variable pressure SEM, with a tungsten filament and ESED II detector. The SEM images portrayed in FIG. 8 confirm the size variation associated with CD-MOF-1 growth in the presence of CTAB.

CD-MOF-1 Crystallizations with CTAB monitored by SEM show the subtle differences in the size and shape of the CD-MOF-1 particles. The particles exhibit cubic morphology consistently with small defects at the crystal surfaces. The non-conductive nature of CD-MOF-1 crystals results in the presence of surface charging, giving rise to the 'white glowing' of particles. Surface charging is reduced partially (FIG. 8C) using sputtering techniques.

3.3. Powder X-Ray Diffraction

Figure 9:
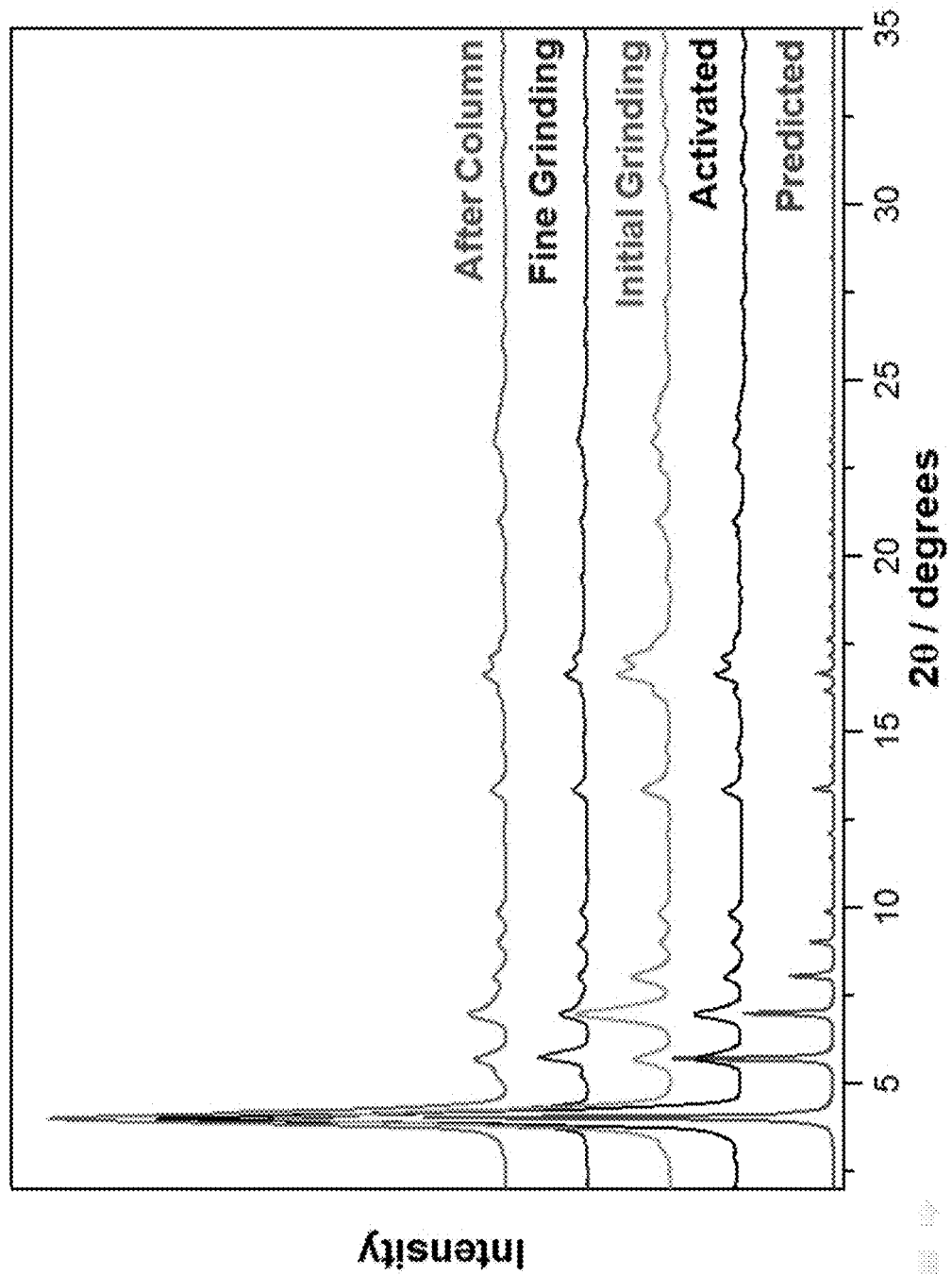
FIG. 9 depicts powder X-ray diffraction patterns of CD-MOF-2 at different intervals of processing when preparing to pack the CD-MOF-2 column, Red—calculated powder diffraction pattern from single crystal X-ray diffraction, Black—after harvesting and activation under vacuum, Green—CD-MOF-2 after initial grinding using automated grinder, Blue—CD-MOF-2 after intensive fine grinding under a nitrogen atmosphere, Pink—CD-MOF-2 after usage in the HPLC column for 72 h.

Powder patterns for CD-MOF-1 and CD-MOF-2 (FIG. 9) were collected on a Bruker AXS APEX2 diffractometer equipped with a CCD detector and a CuKα IμS microfocus source with MX optics. Overlapping sections of data were matched and the resulting pattern integrated using the Bruker APEX2 Phase ID program, before the powder pattern data was treated for amorphous background scattering.

Figure 10:
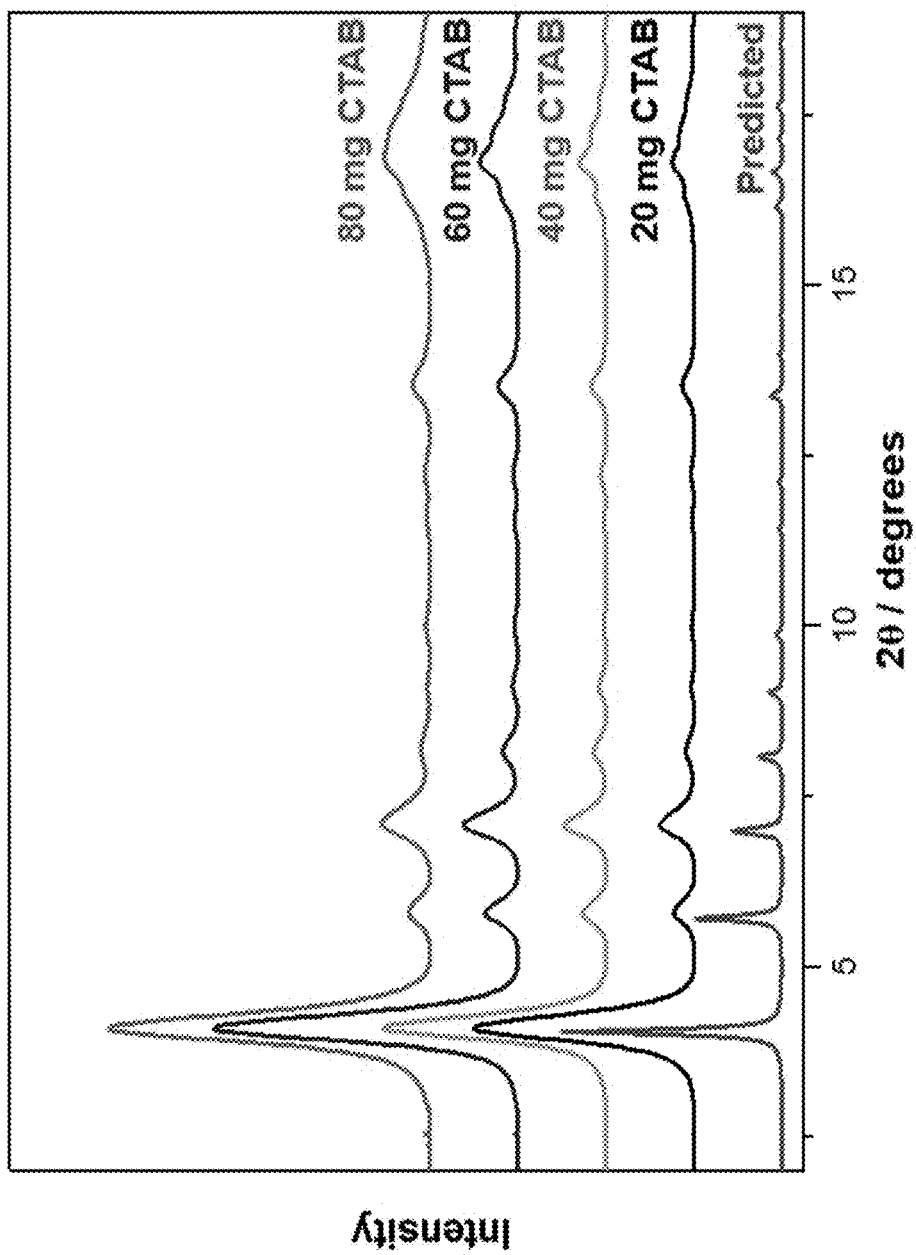
FIG. 10 depicts powder X-ray diffraction patterns of CD-MOF-1 employed in the packing of the CD-MOF-1 Bottom-up column. The different samples were crystallized in the presence of varying amounts of CTAB, Red—calculated powder diffraction pattern from the single crystal X-ray diffraction pattern, Black—CD-MOF-1 crystallized with 20 mg CTAB, Green—CD-MOF-1 crystallized with 40 mg CTAB, Blue—CD-MOF-1 crystallized with 60 mg CTAB, Pink—CD-MOF-1 crystallized with 80 mg CTAB.

Although the powder X-ray diffraction patterns (FIG. 10) for CD-MOF-1 exhibit line broadening as the particle sizes decrease, crystallinity remains consistent with that observed for the predicted powder diffraction pattern calculated from the CD-MOF-1 single crystal diffraction data. This observation confirms the formation of CD-MOF-1 regardless of the CTAB concentration.

Example 4

HPLC Analysis Using CD-MOF-1 and CD-MOF-2 Columns 4.1. Xylene Separations
4.1.1. Xylene Isomers The similar physical properties (Table 6) of the BTEX molecules (Benzene, Toluene, Ethylbenzene and the Xylene isomers) gives rise to considerable challenges when conducting separations using conventional techniques such as distillation (Minceva, M.; Rodrigues, A. E. *AIChE Journal* 2007, 53, 138), crystallization (Lima, R. M.; Grossmann, I. E. *AIChE Journal* 2009, 55, 354; Eccli, W. D. & Fremuth, A. D. S. Single temperature stage crystallisation of para-xylene U.S. Pat. No. 5,498,822 (1996)) and simulated moving bed technologies (Minceva, M.; Rodrigues, A. E. *Chem. Eng. Res. Des.* 2004, 82, 667).

TABLE 6

Physical properties of BTEX (benzene, toluene, ethylbenzene and the xylene isomers) components

| Adsorbant | Boiling Point/° C. | Melting Point/° C. | Kinetic Diameter/nm |
|---|---|---|---|
| Benzene | 80.1 | 5.5 | 0.58 |
| Toluene | 110.6 | −95 | 0.61 |
| Ethylbenzene | 136.2 | −95 | 0.62 |
| ortho-Xylene | 144.4 | −27.2 | 0.68 |
| meta-Xylene | 139.1 | −47.9 | 0.68 |
| para-Xylene | 138.3 | 13.4 | 0.58 |

Figure 11A:
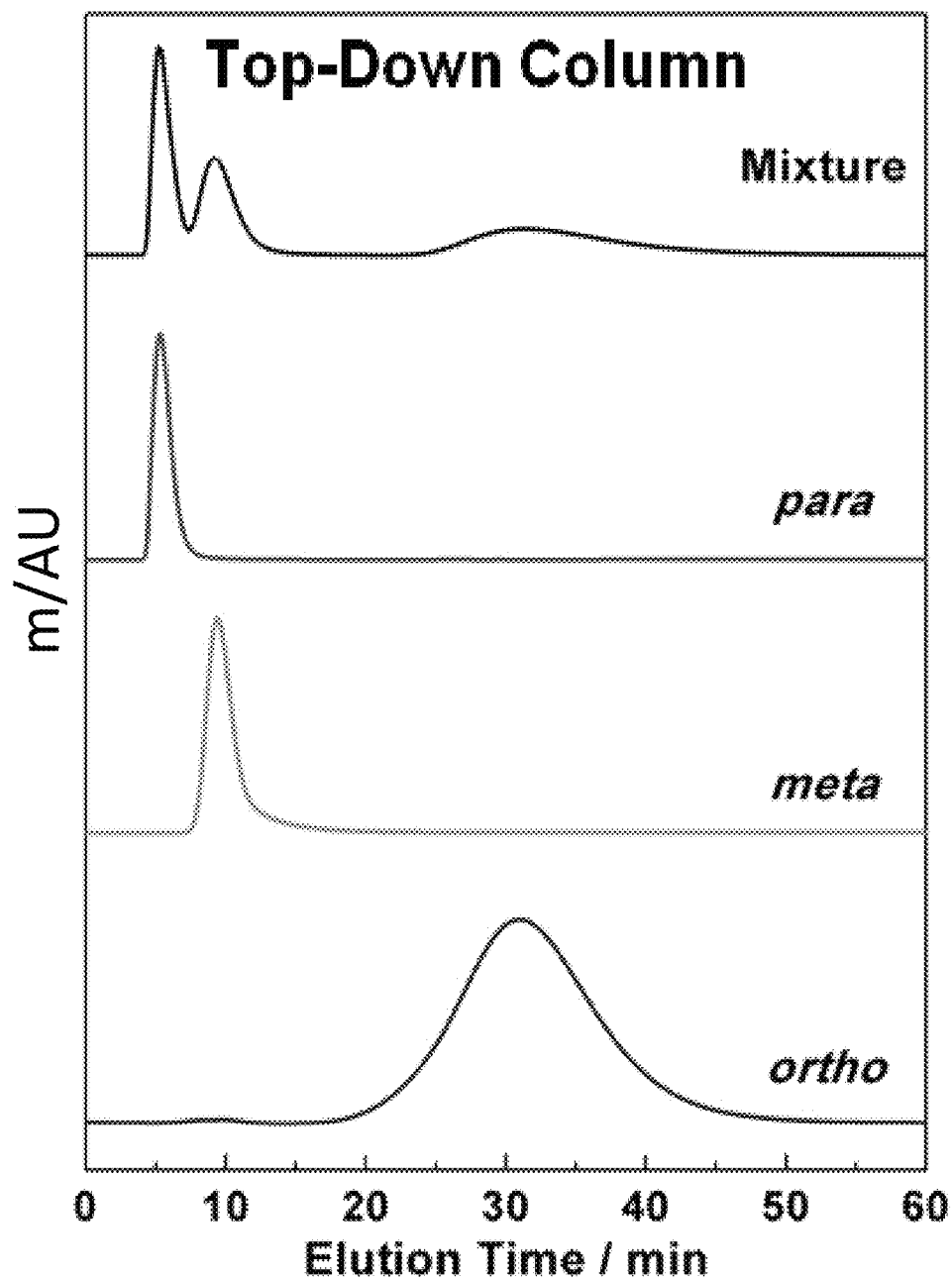
FIG. 11A depicts CD-MOF Column separations of 50 mg mL$^{-1}$ xylene mixtures in HPLC-grade hexane at a flow rate of 1 mL min$^{-1}$ with a top-down CD-MOF-2 column—particle sizes 10-37 µm The stacking of separation profiles shows the assignment of the elution order from the mixture of xylene isomers (black) as para-xylene (red), meta-xylene (green) and ortho-xylene (blue) at 255 nm.
Figure 11B:
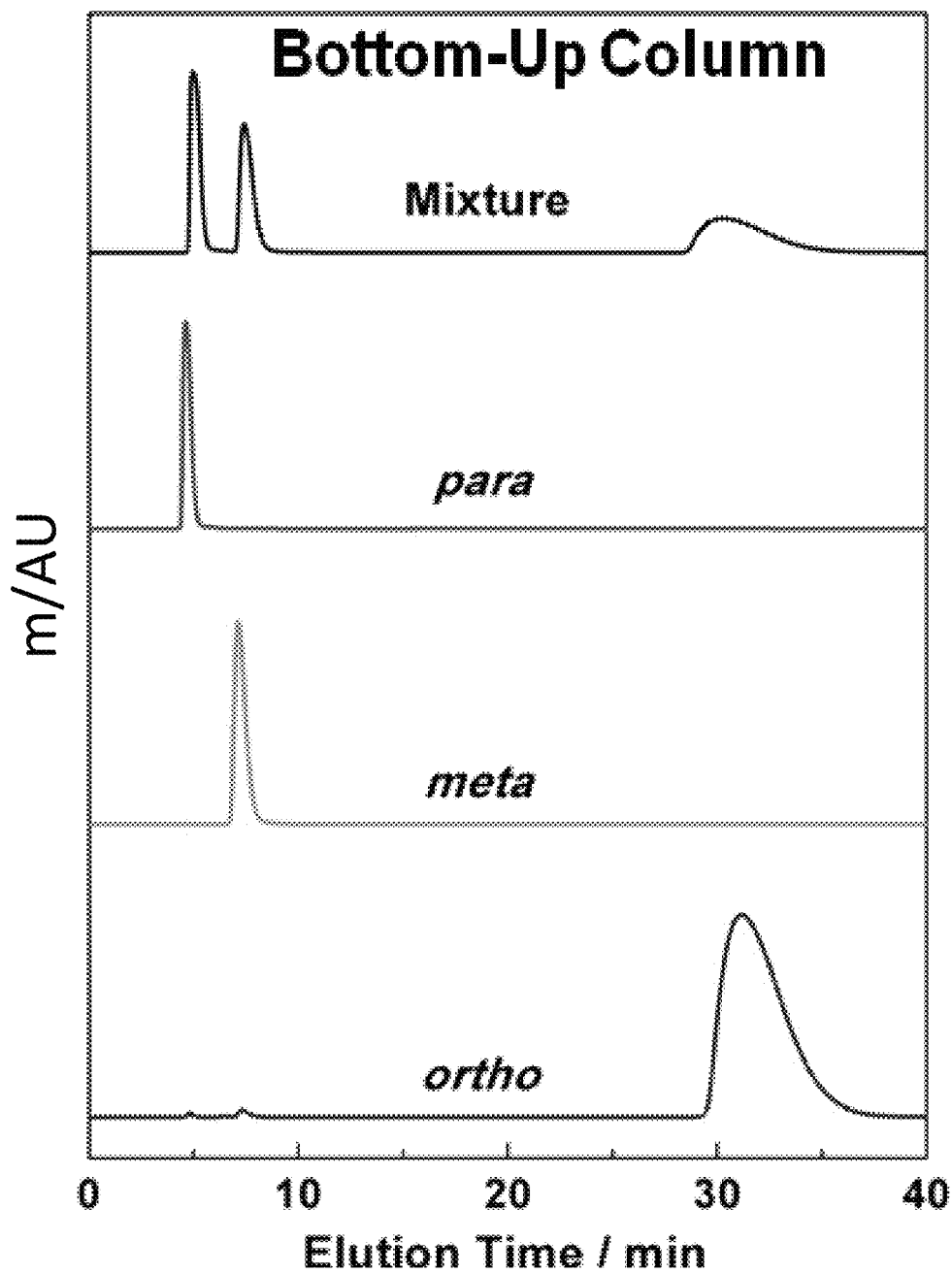
FIG. 11B depicts CD-MOF Column separations of 50 mg mL$^{-1}$ xylene mixtures in HPLC-grade hexane at a flow rate of 1 mL min$^{-1}$ with a bottom-up CD-MOF-1 column—particle sizes 10-15 The stacking of separation profiles are as presented in FIG. 11A.
Figure 12:
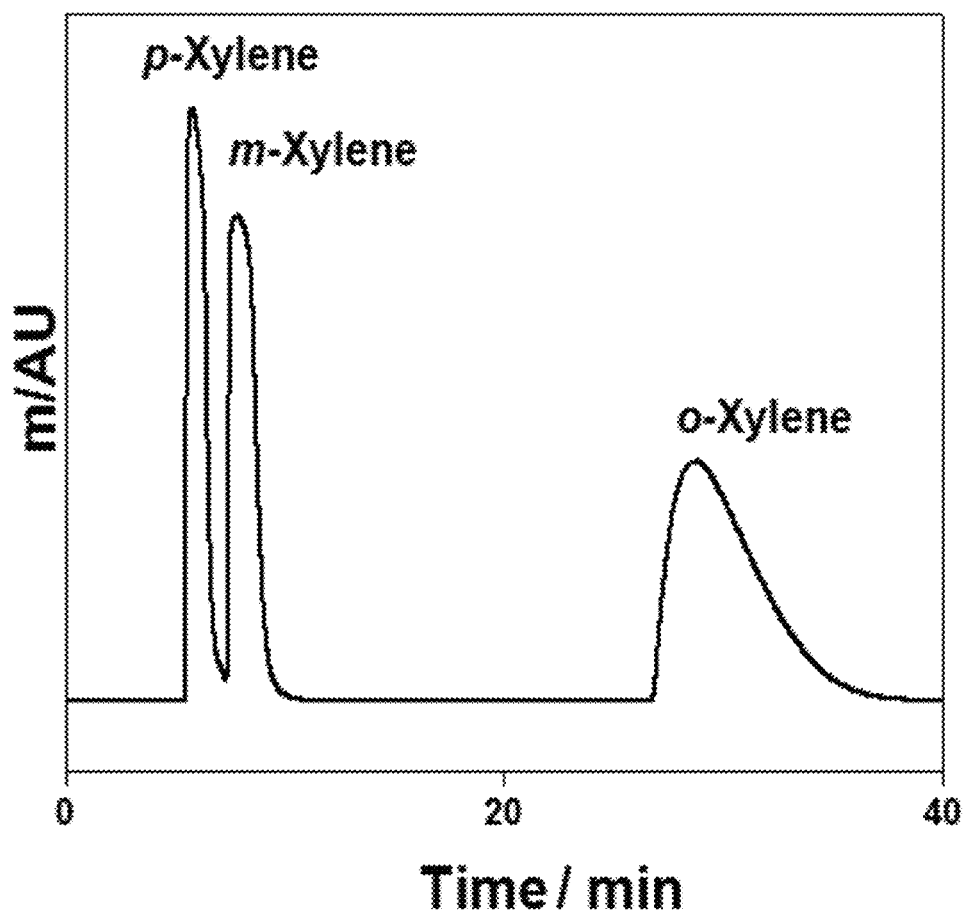
FIG. 12 depicts a bottom-up CD-MOF-1 column—particle sizes 10-15 µm—separation of 10 µL of neat xylene mixture at a flow rate of 1 mL min$^{-1}$, shows the elution order of para-xylene, meta-xylene and ortho-xylene.

Separations (FIG. 11) of the three xylene isomers using both a top-down HPLC column and a bottom-up HPLC column revealed (Table 7) significant differences in their corresponding resolutions and separation factors. The improved resolution and separation factors between the top-down and bottom-up columns coincide with the control over small regular particle formation, resulting in more efficient packing inside the column. Liquid-phase separations in hexane of 10 μL injections of 50 mg mL$^{-1}$ xylene mixtures exhibited base-line separation with the retention order ortho>meta>para. Separation of the xylene isomers is maintained upon injection of 10 μL of a neat solution of xylenes FIG. 12. The separation of the xylene isomers is accompanied by the separation of BTEX with the elution order, para>meta>ethylbenzene>toluene>ortho>benzene.

4.1.2. BTX Mixture

Figure 13A:
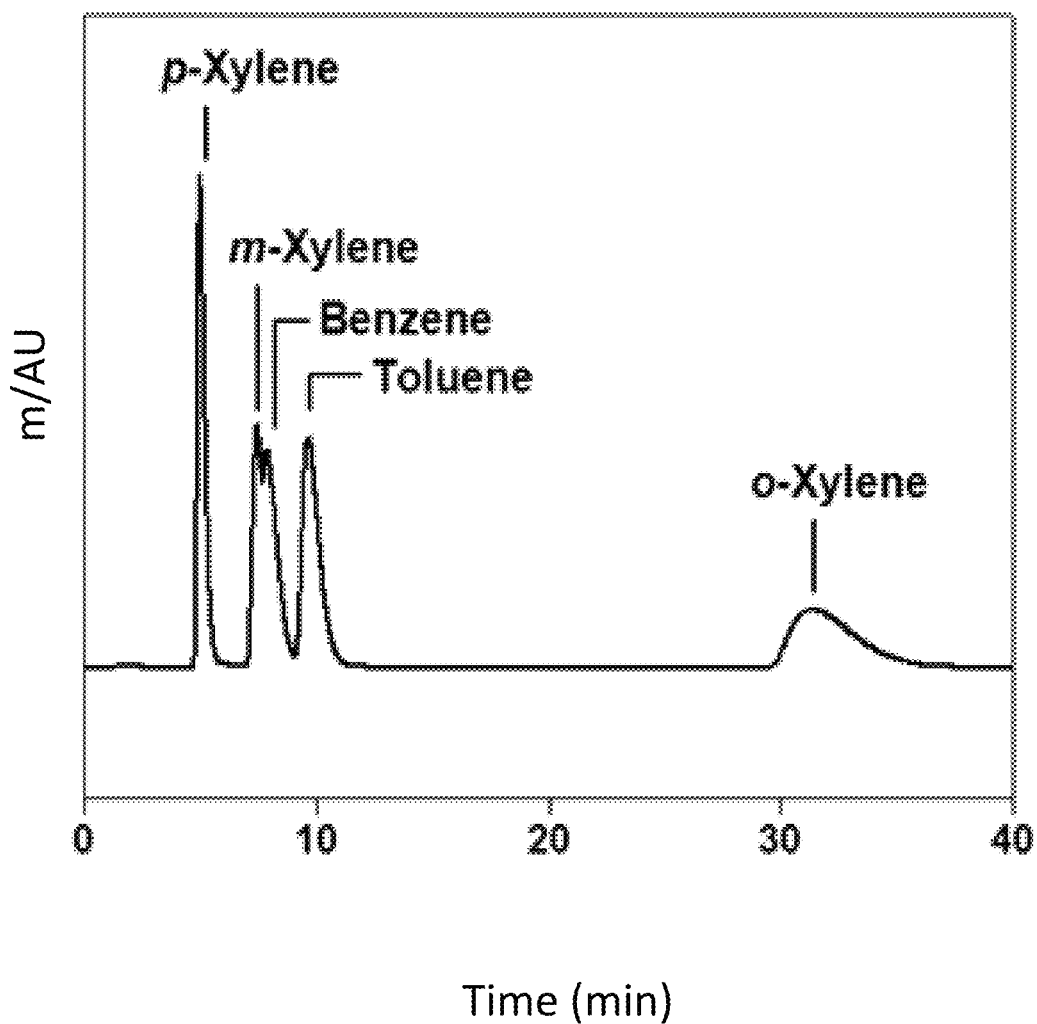
FIG. 13A depicts a bottom-up CD-MOF-1 column—particle sizes 10-15 µm—separations of 50 mg mL$^{-1}$ BTX mixtures in HPLC-grade hexane at a flow rate of 1 mL min$^{-1}$ after running the column for 4 h.
Figure 13B:
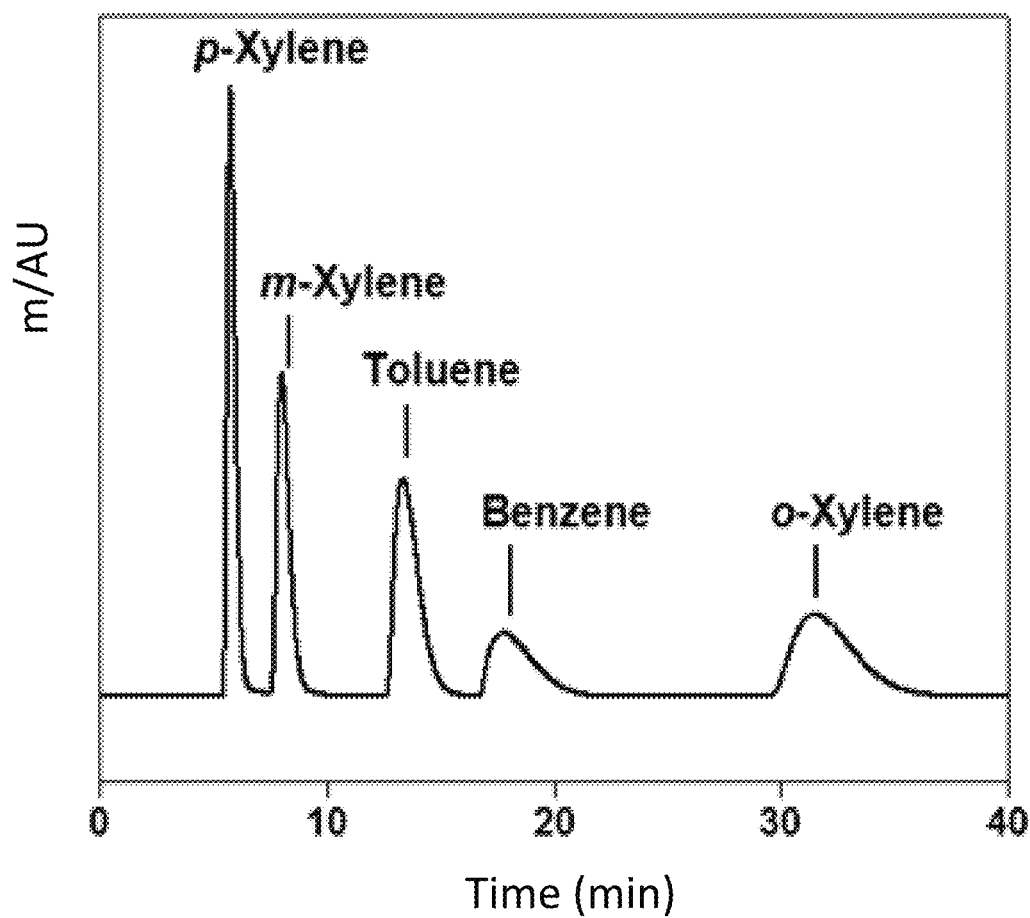
FIG. 13B depicts a bottom-up CD-MOF-1 column—particle sizes 10-15 µm—separations of 50 mg mL$^{-1}$ BTX mixtures in HPLC-grade hexane at a flow rate of 1 mL min$^{-1}$ after running the column for 30 h.
Figure 14:
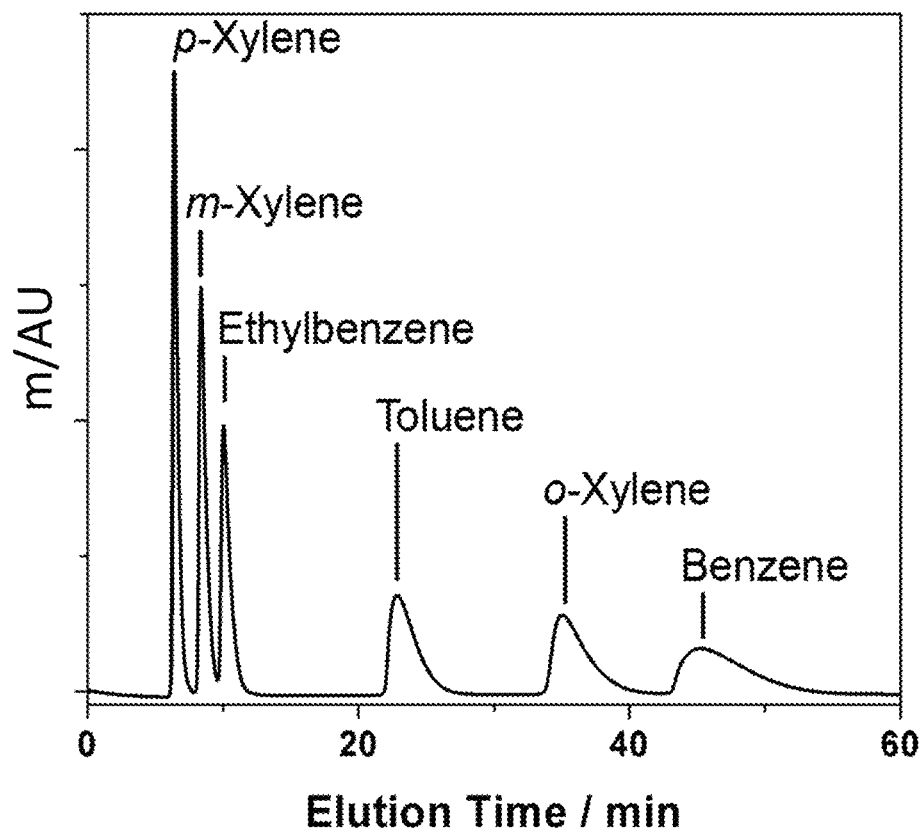
FIG. 14 depicts a bottom-up CD-MOF-1 column—particle sizes 10-15 µm—separations of 50 mg mL$^{-1}$ BTEX mixtures using HPLC-grade hexane as the mobile phase at a flow rate of 1 mL min$^{-1}$ after activation of the column by a $CH_2Cl_2$, detected at 255 nm.

Separation (FIG. 13) of BTX (benzene, toluene, and the three xylene isomers) was achieved after 6 h. Separation (FIG. 14) of BTEX was achieved after removing MeOH from the framework using $^i$PrOH, the bottom-up CD-MOF-1 column is then reactivated by removing the $^i$PrOH using CH2C12 before running the BTEX mixtures in HPLC-grade hexane.

4.1.3. BTEX Mixture
4.2. Ethyltoluene Separations

Figure 15:
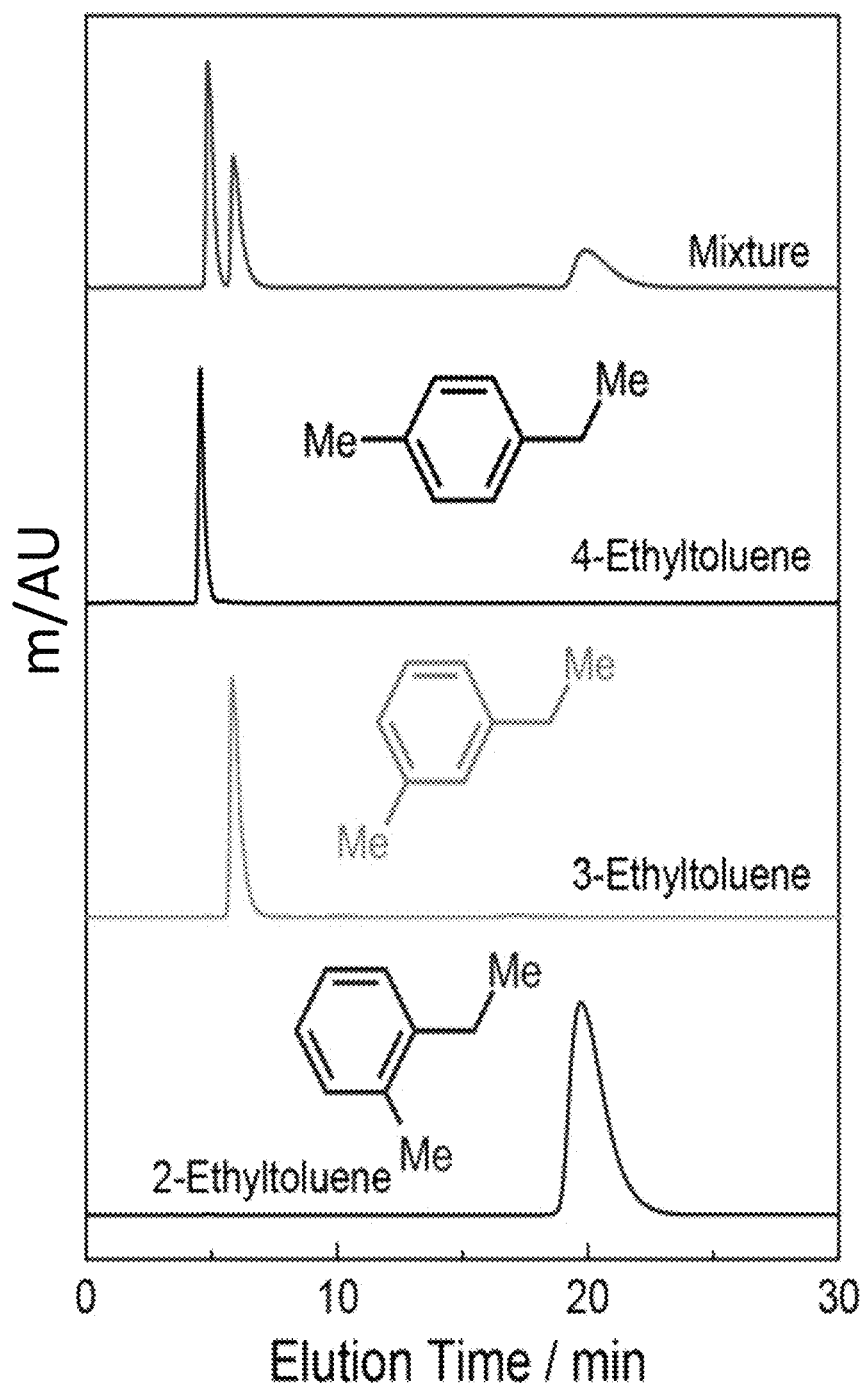
FIG. 15 depicts a bottom-up CD-MOF-1 column separation of 50 mg mL$^{-1}$ 4-ethyltoluene, 3-ethyltoluene and 2-ethyltoluene in HPLC-grade hexane at a flow rate of 1 mL min$^{-1}$ using particle sizes 10-15 µm detected at 266 nm.

Separation (FIG. 15) of the regioisomers of ethyltoluene highlight the columns selectivity of ortho>meta>para, with isomers eluting at similar times to those observed for their respective xylene isomers. This separation is indicative of the guest's ability to pack within the transverse pores of the γ-CD rings, revealing CD-MOFs ability to shape-select the regioisomers of extended substituted aromatic hydrocarbons.

Figure 16:
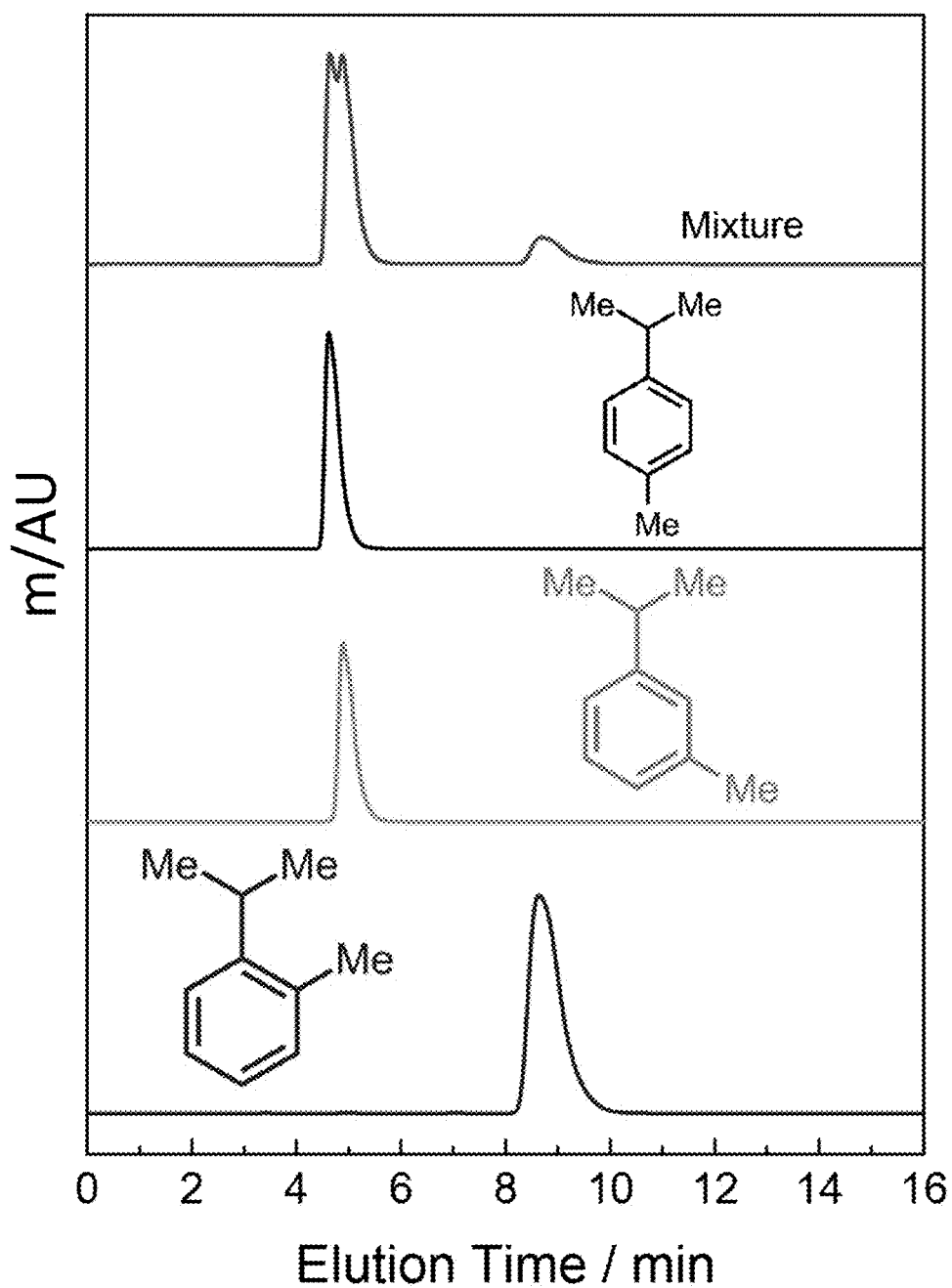
FIG. 16 depicts a bottom-up CD-MOF-1 column separation of 50 mg mL$^{-1}$ 4-cymene, 3-cymene and 2-cymene in HPLC-grade hexane at a flow rate of 1 mL min$^{-1}$ using particle sizes 10-15 µm detected at 266 nm.

4.3. Cymene Separations Separation (FIG. 16) of the regioisomers of cymene were used to investigate the extent of the ortho>meta>para selectivity within CD-MOF. Although the selectivity order is consistent with that observed for the other regioisomers of compounds separated using CD-MOF, the ability to separate the regioisomers is reduced, with baseline merging for the para- and meta-cymene signals. This suggests the limit of CD-MOFs shape recognition has been reached, with the additional branching preventing efficient packing of both the para- and meta-cymene isomers.

Figure 17:
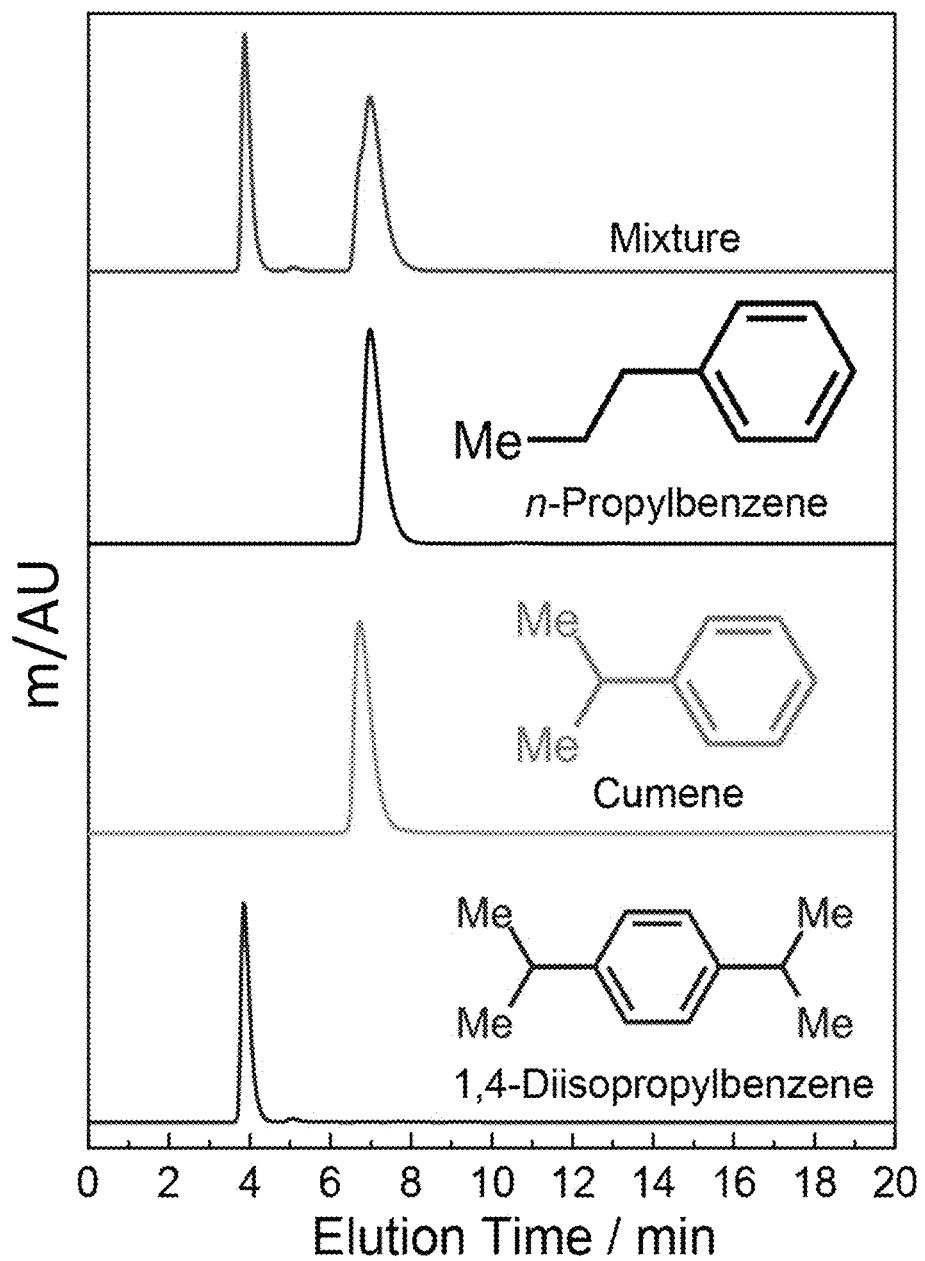
FIG. 17 depicts a bottom-up CD-MOF-1 column separation of 50 mg mL$^{-1}$ cumene, n-propylbenzene and 1,4-diisopropylbenzene mixture in HPLC-grade hexane at a flow rate of 1 mL min$^{-1}$ using particle sizes 10-15 µm detected at 255 nm.

4.4. Cumene Separations Separation (FIG. 17) of the valuable petrochemical feedstock cumene from impurities n-propylbenzene and 1,4-diisopropylbenzene was achieved using an activated bottom-up CD-MOF-1 column.

Example 5

Selectivity Calculations and Separation Factors 5.1. Calculations for Capacity and Separation Factors Capacity factors (k) for liquid phase analytical chromatographic data recorded for the separations of compounds in Section D were calculated (El Osta, R.; Carlin-Sinclair, A.; Guillou, N.; Walton, R. I.; Vermoortele, F.; Maes, M.; de Vos, D.; Millange, F. *Chem. Mater.* 2012, 24, 2781; Snyder, L. R.; Kirkland, J. J.; Glajch, J. L. Practical HPLC method development Second Edition, John Wiley & Sons, Inc. (1997)) using Equation 1. The capacity factor (k) defines the amount of time a compound spends in the stationary phase versus the mobile phase.

$$k_i = \frac{tr_i - t_{res}}{t_{res}}, \quad (1)$$

where $k_i$ represents Capacity factor, $tr_i$ represents Retention time and $t_{res}$ represents Bed void time.

The separation ability of a material is determined by the separation factor (El Osta, R.; Carlin-Sinclair, A.; Guillou, N.; Walton, R. I.; Vermoortele, F.; Maes, M.; de Vos, D.; Millange, F. *Chem. Mater.* 2012, 24, 2781) ($\alpha_{ij}$), which measures the difference in interactions between the two compounds in question and the stationary phase. The separation factor ($\alpha_{ij}$) is calculated (El Osta, R.; Carlin-Sinclair, A.; Guillou, N.; Walton, R. I.; Vermoortele, F.; Maes, M.; de Vos, D.; Millange, F. *Chem. Mater.* 2012, 24, 2781) as a ratio between capacity factors of the two compounds using Equation 2.

$$\alpha_{ij} = \frac{k_i}{k_j}, \quad (2)$$

where $\alpha_{ij}$ represents Separation factor, $k_i$ represents Capacity factor i and $k_j$ represents Capacity factor j.

The resolution factor (R) of the peaks is calculated using Equation 3. It determines (Walton, R. I.; Vermoortele, F.; Maes, M.; de Vos, D.; Millange, F. *Chem. Mater.* 2012, 24, 2781) the difference in retention times, whilst taking account of the peak width.

$$R = \frac{2[tr_i - tr_j]}{W_i + W_j}, \quad (3)$$

where R represents Resolution factor, $tr_i$ and $tr_j$ represent Retention times i and j, respectively, $W_i$ and $W_j$ represents Peak widths i and j, respectively.

5.2. Separation Factor Tables

The separation factors for xylene isomers for both the CD-MOF-2 top-down column and CD-MOF-1 bottom-up column are recorded in Table 7. BTX separation factors are recorded in Table 8. The full activation of the bottom-up CD-MOF-1 column resulted in the separation of BTEX mixtures with separation factors recorded in Table 9, these can be compared to the separation factors of currently available MOFs, some of which are recorded in Table 10.

TABLE 7

CD-MOF column separation factors of 50 mg mL$^{-1}$ xylene mixtures in HPLC-grade hexane at a flow rate of 1 mL min$^{-1}$

| | | | j | | |
|---|---|---|---|---|---|
| Adsorbent | Solvent | i | ortho-Xylene | meta-Xylene | para-Xylene |
| CD-MOF-2 | Hexane | ortho-Xylene | — | 4.76 | 16.37 |
| Top-down | | meta-Xylene | 0.21 | — | 3.44 |
| Column | | para-Xylene | 0.06 | 0.29 | — |
| CD-MOF-1 | Hexane | ortho-Xylene | — | 6.73 | 17.93 |
| Bottom-up | | meta-Xylene | 0.15 | — | 2.67 |
| Column | | para-Xylene | 0.06 | 0.38 | — |
| CD-MOF-1 | Pure | ortho-Xylene | — | 5.72 | 10.76 |
| Bottom-up | Xylene | meta-Xylene | 0.17 | — | 1.88 |
| Column | Mixture | para-Xylene | 0.09 | 0.53 | — |

TABLE 8

CD-MOF column separation factors of 50 mg mL$^{-1}$ BTX mixtures in HPLC-grade hexane at a flow rate of 1 mL min$^{-1}$

| | | j | | | | |
|---|---|---|---|---|---|---|
| Adsorbent | i | ortho-Xylene | meta-Xylene | para-Xylene | Benzene | Toluene |
| CD-MOF-1 | ortho-Xylene | — | 7.08 | 17.89 | 6.29 | 4.49 |
| Bottom-up | meta-Xylene | 0.14 | — | 2.53 | 0.89 | 0.63 |
| Column | para-Xylene | 0.06 | 0.39 | — | 0.35 | 0.25 |
| 4 Hours | Benzene | 0.16 | 1.12 | 2.85 | — | 0.71 |
| | Toluene | 0.22 | 1.58 | 3.99 | 1.40 | — |
| CD-MOF-1 | ortho-Xylene | — | 6.11 | 12.19 | 1.96 | 2.82 |
| Bottom-up | meta-Xylene | 0.16 | — | 1.99 | 0.32 | 0.46 |
| Column | para-Xylene | 0.08 | 0.50 | — | 0.16 | 0.23 |
| 30 Hours | Benzene | 0.50 | 3.10 | 6.19 | — | 1.43 |
| | Toluene | 0.35 | 2.17 | 4.33 | 0.69 | — |

TABLE 9 activated bottom-up CD-MOF column separation factors of 50 mg mL$^{-1}$ BTEX mixtures in HPLC-grade hexane at a flow rate of 1 mL min$^{-1}$

| | | j | | | | | |
|---|---|---|---|---|---|---|---|
| Adsorbent | i | ortho-Xylene | meta-Xylene | para-Xylene | Benzene | Toluene | Ethylbenzene |
| CD-MOF-1 | ortho-Xylene | — | 6.68 | 11.26 | 0.76 | 1.61 | 4.75 |
| Bottom-up | meta-Xylene | 0.15 | — | 1.69 | 0.11 | 0.24 | 0.71 |
| Column | para-Xylene | 0.09 | 0.59 | — | 0.07 | 0.14 | 0.42 |
| | Benzene | 1.32 | 8.82 | 14.88 | — | 2.13 | 6.27 |
| | Toluene | 0.62 | 4.14 | 6.98 | 0.47 | — | 2.94 |
| | Ethylbenzene | 0.21 | 1.41 | 2.37 | 0.21 | 0.34 | — |

TABLE 10

Separation factors of known frameworks taken from the literature for the three xylene isomers and ethylbenzene

| Adsorbent | Solvent | i | ortho-Xylene | meta-Xylene | para-Xylene | Ethyl-benzene | Ref. |
|---|---|---|---|---|---|---|---|
| HKUST-1 | Hexane | ortho-Xylene | — | 0.4 | 0.7 | 0.7 | S7 |
| [Cu$_3$(BTC)$_2$] | | meta-Xylene | 2.4 | — | 1.1 | 1.4 | |
| | | para-Xylene | 1.4 | 0.9 | — | 1.2 | |
| | | Ethyl-benzene | 1.4 | 0.7 | 0.8 | — | |
| MIL-47 | Hexane | ortho-Xylene | — | 2.0 | 1.4 | 10.9 | S8 |
| | | meta-Xylene | 0.5 | — | 0.4 | 4.2 | |
| | | para-Xylene | 0.7 | 2.9 | — | 9.7 | |
| | | Ethyl-benzene | 0.1 | 0.2 | 0.1 | — | |
| MIL-53(Al) | Hexane | ortho-Xylene | — | 2.7 | 3.5 | 10.9 | S7, S8 |
| | | meta-Xylene | 0.4 | — | 1.2 | 3.8 | |
| | | para-Xylene | 0.3 | 0.8 | — | 3.1 | |
| | | Ethyl-benzene | 0.1 | 0.3 | 0.3 | — | |
| MIL-53(Fe) | Heptane | ortho-Xylene | — | 1.3 | 3.5 | 12.3 | S9 |
| | | meta-Xylene | 0.7 | — | 2.5 | 9.2 | |
| | | para-Xylene | 0.3 | 0.4 | — | 3.5 | |
| | | Ethyl-benzene | 0.1 | 0.1 | 0.3 | — | |
| UiO-66 | Heptane | ortho-Xylene | — | 1.8 | 2.4 | — | S10 |
| | | meta-Xylene | 0.6 | — | — | — | |
| | | para-Xylene | 0.4 | — | — | — | |
| | | Ethyl-benzene | — | — | — | — | |

The separation factors for the bottom-up CD-MOF-1 column of cumene from impurity mixtures are recorded in Table 11. Separation factors are recorded for the regioisomers of ethyltoluene (Table 12) for comparison to those recorded for the regioisomers of xylene.

TABLE 11

Bottom-up CD-MOF-1 column separation factors of 50 mg mL$^{-1}$ cumene from impurity mixtures of n-propylbenzene and 1,4-diisopropylbenzene in HPLC-grade hexane at a flow rate of 1 mL min$^{-1}$

| Adsorbent | Solvent | i | Diisopropylbenzene | Cumene | propylbenzene |
|---|---|---|---|---|---|
| CD-MOF-1 | Hexane | Diisopropylbenzene | — | 0.14 | 0.12 |
| Bottom-up | | Cumene | 7.12 | — | 0.88 |
| Column | | n-propylbenzene | 8.09 | 1.13 | — |

TABLE 12

Bottom-up CD-MOF-1 column separation factors of 50 mg mL$^{-1}$ mixtures of 4-, 3- and 2-ethyltoluene in HPLC-grade hexane at 1 mL min$^{-1}$

| Adsorbent | Solvent | i | 4-Ethyltoluene | 3-Ethyltoluene | 2-Ethyltoluene |
|---|---|---|---|---|---|
| CD-MOF-1 | Hexane | 4-Ethyltoluene | — | 0.47 | 0.07 |
| Bottom-up | | 3-Ethyltoluene | 2.10 | — | 0.15 |
| Column | | 2-Ethyltoluene | 13.77 | 6.56 | — |

Example 6

Computational Modeling and Analysis

Vapor phase pure component and mixture adsorption isotherms in CDMOF-2 were calculated from grand canonical Monte Carlo (GCMC) simulations using the Multipurpose Simulation Code (Gupta, A.; Chempath, S.; Sanborn, M. J.; Clark, L. A.; Snurr, R. Q. *Mol. Simul.* 2003, 29, 29) MuSiC. GCMC moves used were insertion, deletion, translation and rotation and, in the case of binary mixtures, we also employed identity swap moves. For each pressure point we used 150×10$^6$ GCMC steps for equilibration, after which another 150×10$^6$ steps were employed to calculate the average properties. We used one unit cell of CDMOF-2 with dimensions of 31.07×31.07×31.07 Å. Framework atoms were kept fixed at their crystallographic coordinates during the simulations. The Universal Force Field (Rappe, A. K.; Casewit, C. J.; Colwell, K. S.; Goddard, W. A.; Skiff, W. M. *J. Am. Chem. Soc.*, 1992, 114, 10024) (UFF) was employed for the Lennard-Jones parameters of the framework atoms. The OPLS (Jorgensen, W. L.; Nguyen, T. B. *J. Comput. Chem.*, 1993, 14, 195) force field was used to model xylene isomers.

Figure 18A:
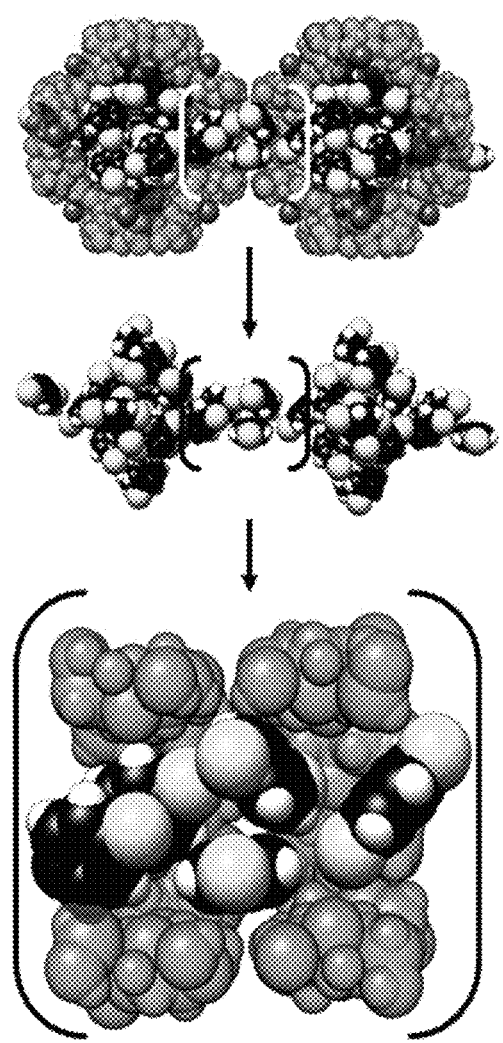
FIG. 18A depicts molecular simulation snapshots of the xylene isomers within the CD-MOF-2 framework viewed down the <1 0 0> axis for pure component para-xylene (black) and the corresponding methyl-groups colored (yellow) for the sake of clarity.
Figure 18B:
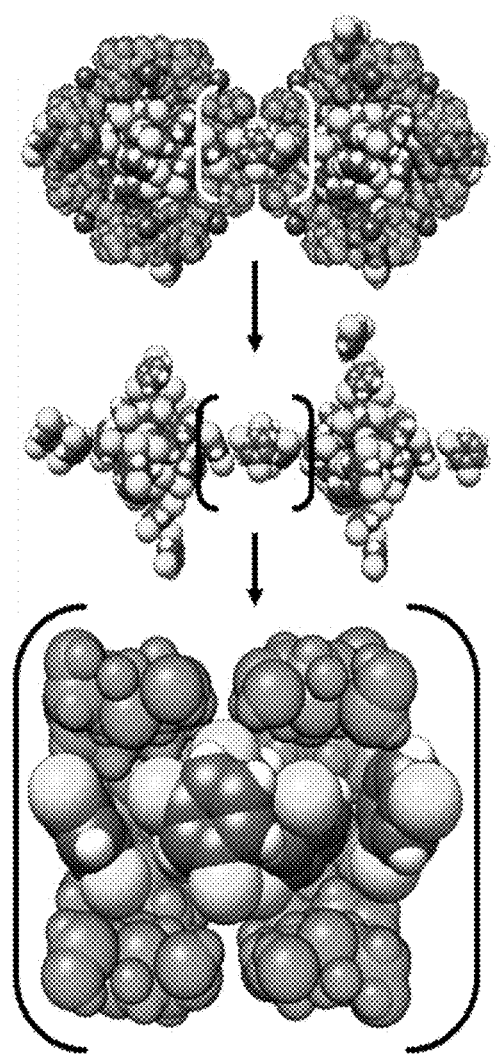
FIG. 18B depicts molecular simulation snapshots of the xylene isomers within the CD-MOF-2 framework viewed down the <1 0 0> axis for pure component meta-xylene (green) and corresponding methyl-groups colored (yellow) for the sake of clarity.
Figure 18C:
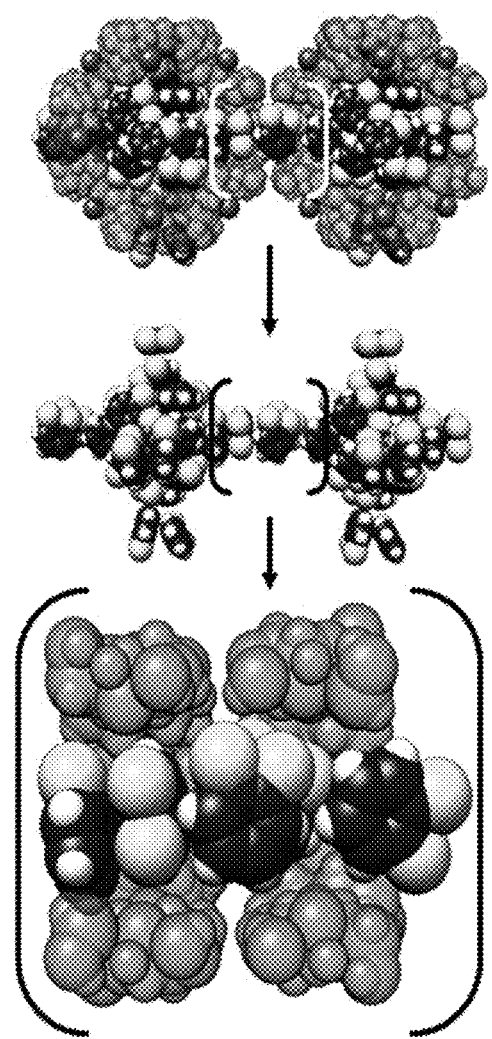
FIG. 18C depicts molecular simulation snapshots of the xylene isomers within the CD-MOF-2 framework viewed down the <1 0 0> axis for the pure component ortho-xylene (blue) and the corresponding methyl-groups colored (yellow) for the sake of clarity.
Figure 19A:
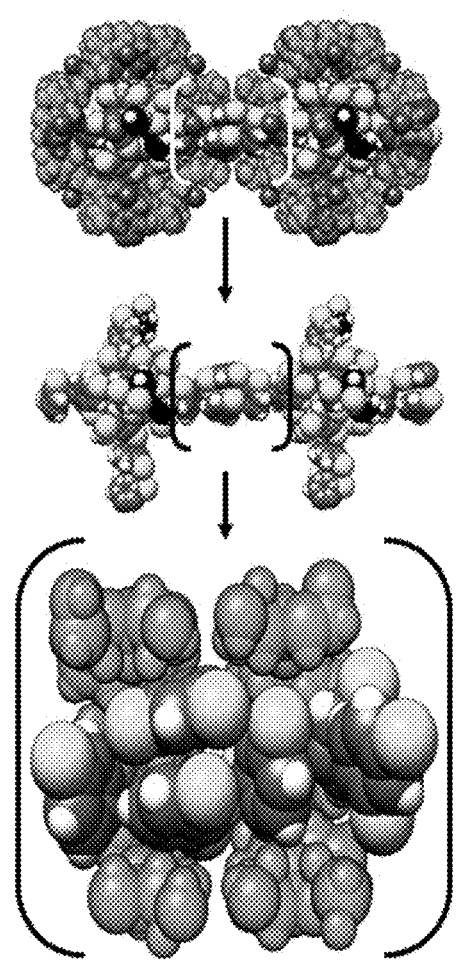
FIG. 19A depicts molecular simulation snapshots of the xylene isomers within the CD-MOF-2 framework viewed down the <1 0 0> axis. Equimolar mixture snapshots of xylene isomers meta-/para-xylene, with para- (black), meta-xylene (green) and their corresponding methyl-groups colored (yellow) for the sake of clarity.
Figure 19B:
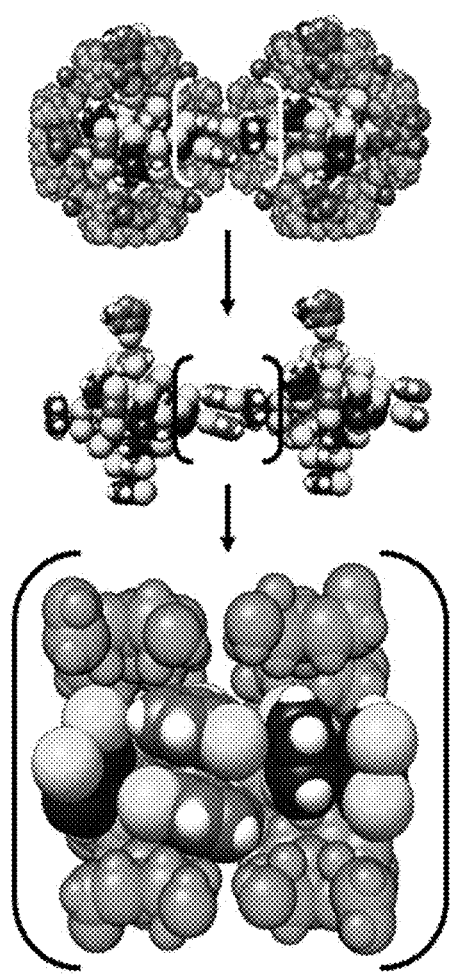
FIG. 19B depicts molecular simulation snapshots of the xylene isomers within the CD-MOF-2 framework viewed down the <1 0 0> axis. Equimolar mixture snapshots of xylene isomers ortho-/meta-xylene, with meta- (green) and ortho-xylene (blue) and their corresponding methyl-groups colored (yellow) for the sake of clarity.
Figure 19C:
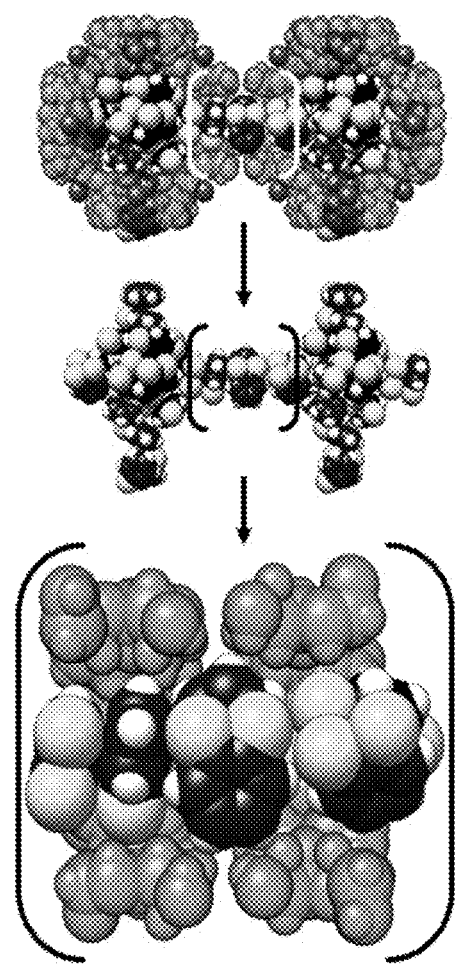
FIG. 19C depicts molecular simulation snapshots of the xylene isomers within the CD-MOF-2 framework viewed down the <1 0 0> axis. Equimolar mixture snapshots of xylene isomers ortho-/para-xylene, with para- (black) and ortho-xylene (blue) and their corresponding methyl-groups colored (yellow) for the sake of clarity.
Figure 20A:
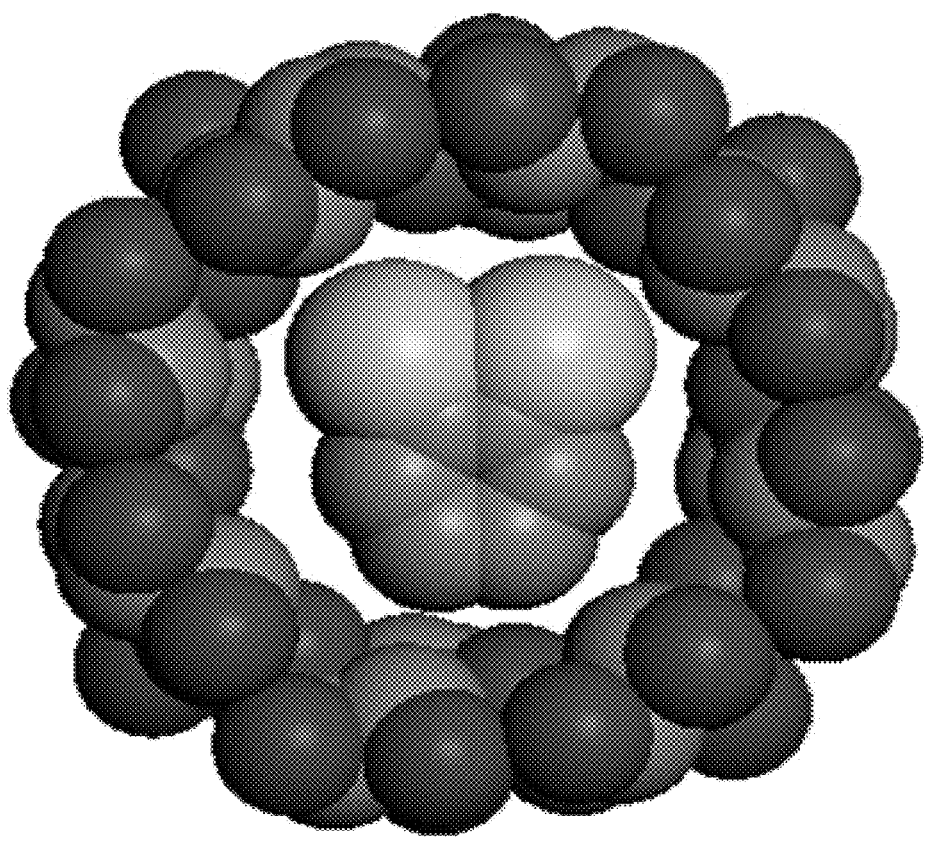
FIG. 20A depicts a schematic illustration of the γ-CD rings with ortho-xylene adsorbed in the ring. The methyl groups in xylenes are illustrated as single yellow spheres, carbons and oxygens are shown in grey and red, respectively. All hydrogen atoms are removed for the sake of clarity.
Figure 20B:
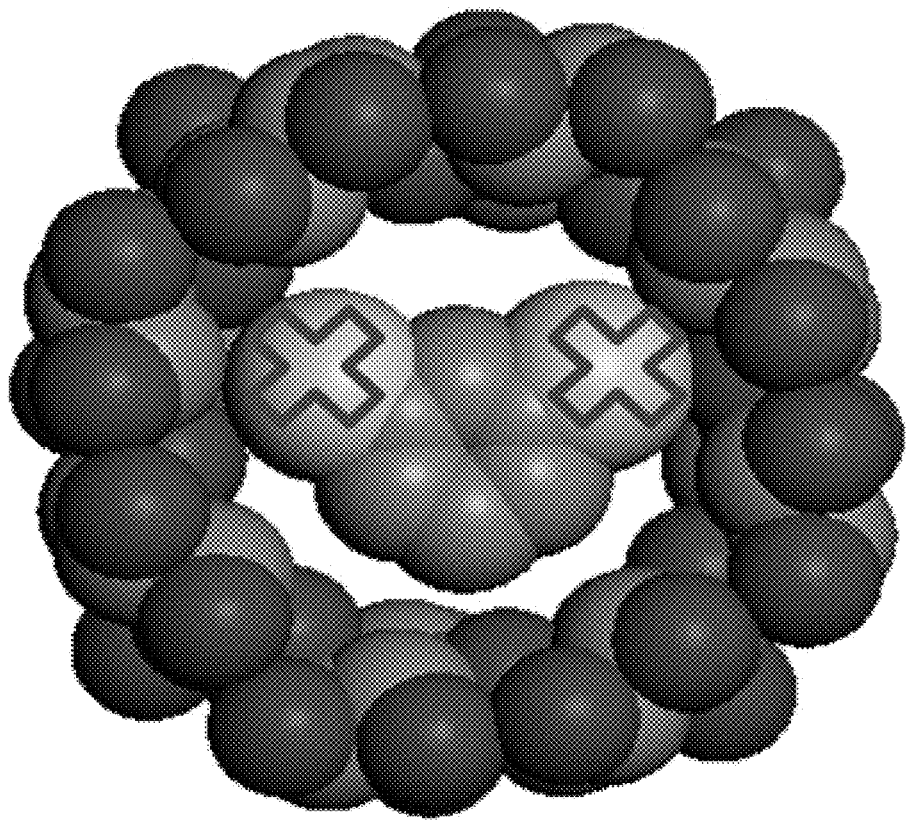
FIG. 20B depicts a schematic illustration of the γ-CD rings with meta-xylene adsorbed in the ring. Crosses emphasize that methyl groups may overlap with the ring atoms in this orientation. The methyl groups in xylenes are illustrated as single yellow spheres, carbons and oxygens are shown in grey and red, respectively. All hydrogen atoms are removed for the sake of clarity.
Figure 20C:
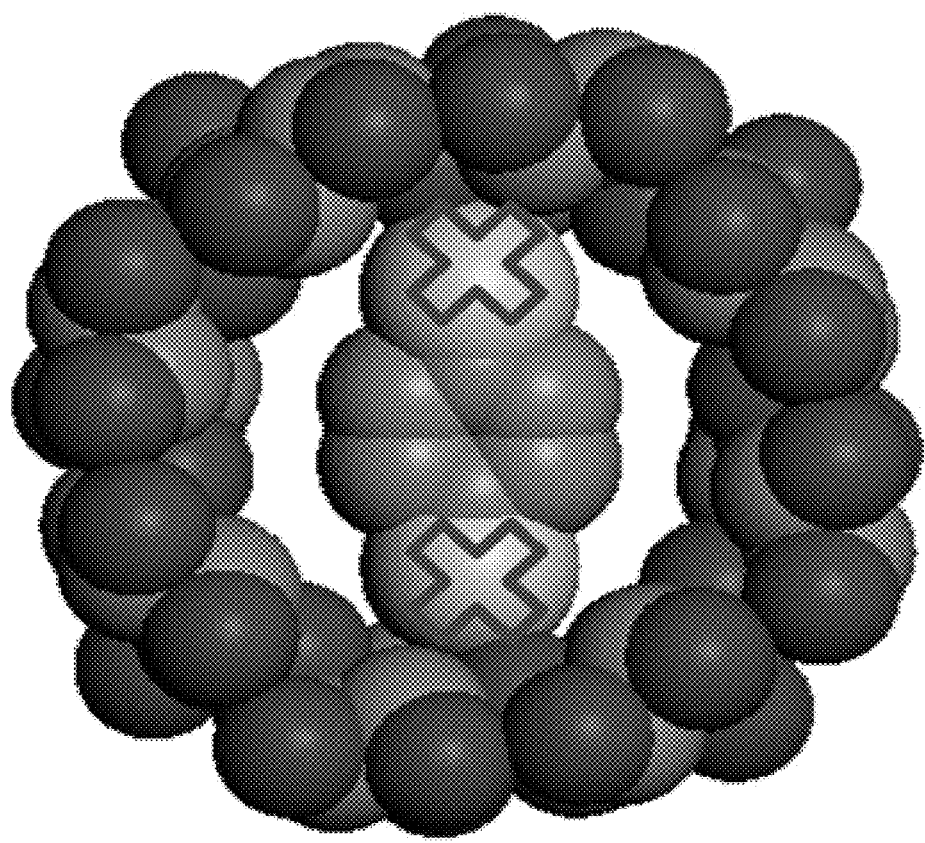
FIG. 20C depicts a schematic illustration of the γ-CD rings with para-xylene adsorbed in the ring. Crosses emphasize that methyl groups may overlap with the ring atoms in this orientation. The methyl groups in xylenes are illustrated as single yellow spheres, carbons and oxygens are shown in grey and red, respectively. All hydrogen atoms are removed for the sake of clarity.

Snapshots from simulations (FIG. 18) of the pure components and mixtures (FIG. 19) at saturation pressures reveal that o-xylene packs in the optimum slipped geometry, arranged in π-π stacking arrays within the transverse channels throughout the CD-MOF-2 framework. The siting analysis also reveals that the orientation of o-xylene maximizes its retention within CDMOF-2 by allowing interaction between both its methyl groups and the γ-CD rings. This particular stacking of o-xylene has been observed in AEL and AFI zeolites.[34] The constitution of methyl groups in m- and p-xylene, however, prevents similar positioning of them with respect to the γ-CD rings without partial overlap (steric interactions) with the framework (FIG. 20A-C). Therefore, m- and p-xylene adsorb primarily inside the larger cavities and pack in disordered arrays throughout the transverse nanopores. The simulation snapshots (FIG. 19) for the o-/m- and o-/p-xylene mixtures show that o-xylene adsorbs almost exclusively in the available space in γ-CD rings that constitute the transverse pores. The ability of o-xylene to dominate site occupancy throughout the framework explains the high o-xylene affinities with respect to m- and p-xylene observed in both the liquid- and gas-phase chromatographic experiments.

Cross Lennard-Jones parameters (Tables 13 and 14) were calculated using Lorentz-Berthelot mixing rules, and a cut-off distance of 12.8 Å was used for all Lennard-Jones interactions. The partial atomic charges for the framework were obtained from the EQeq (Wilmer, C. E.; Kim, K. C.; Snurr, R. Q. *J. Phys. Chem. Lett.*, 2012, 3, 2506) charge equilibrium method. Long range electrostatic interactions (Table 15) for adsorbate-adsorbate and adsorbent-adsorbate were calculated using the Wolf and the Ewald (Dufner, H.; Kast, S. M.; Brickmann, J.; Schlenkrich, M. *J. Comput. Chem.*, 1997, 18, 660) techniques, respectively.

TABLE 13

Lennard-Jones parameters for CD-MOF-2

| Atom | ε/k (K) | σ (Å) | Force field |
|---|---|---|---|
| Rb | 26.67 | 2.60 | UFF[13] |
| O | 30.19 | 3.11 | UFF |
| C | 52.83 | 3.43 | UFF |
| H | 22.14 | 2.57 | UFF |

TABLE 14

Lennard-Jones parameters and partial charges for xylene isomers

| Atom | ε/k (K) | σ (Å) | Charge (e) | Force field |
|---|---|---|---|---|
| C | 35.24 | 3.55 | −0.115 | OPLS[14] |
| H | 15.08 | 2.42 | 0.115 | OPLS |
| CH₃ | 85.47 | 3.80 | 0.115 | OPLS |

TABLE 15

Breakdown of interaction energies for equimolar xylene mixtures at 1 kPa and 298 K in CD-MOF-2

| | Potential energy kJ mol$^{-1}$ | | | |
|---|---|---|---|---|
| | vdW | Coulomb | vdW | Coulomb |
| | ortho-xylene | | para-xylene | |
| Adsorbate-Framework | −49.1 | −1.2 | −39.4 | −1.1 |
| Adsorbate-Adsorbate | −12.3 | 0.3 | −7.5 | −0.08 |

TABLE 15-continued

Breakdown of interaction energies for equimolar xylene mixtures at 1 kPa and 298 K in CD-MOF-2

| | Potential energy kJ mol$^{-1}$ | | | |
|---|---|---|---|---|
| | vdW | Coulomb | vdW | Coulomb |
| | ortho-xylene | | meta-xylene | |
| Adsorbate-Framework | −47.7 | −1.2 | −43.8 | −1 |
| Adsorbate-Adsorbate | −11.4 | 0.3 | −7.8 | 0.08 |
| | meta-xylene | | para-xylene | |
| Adsorbate-Framework | −47.3 | −0.9 | −43.2 | −0.9 |
| Adsorbate-Adsorbate | −10.7 | 0.01 | −8.2 | −0.13 |

6.1. Quantum Chemical Calculations

Figure 21:
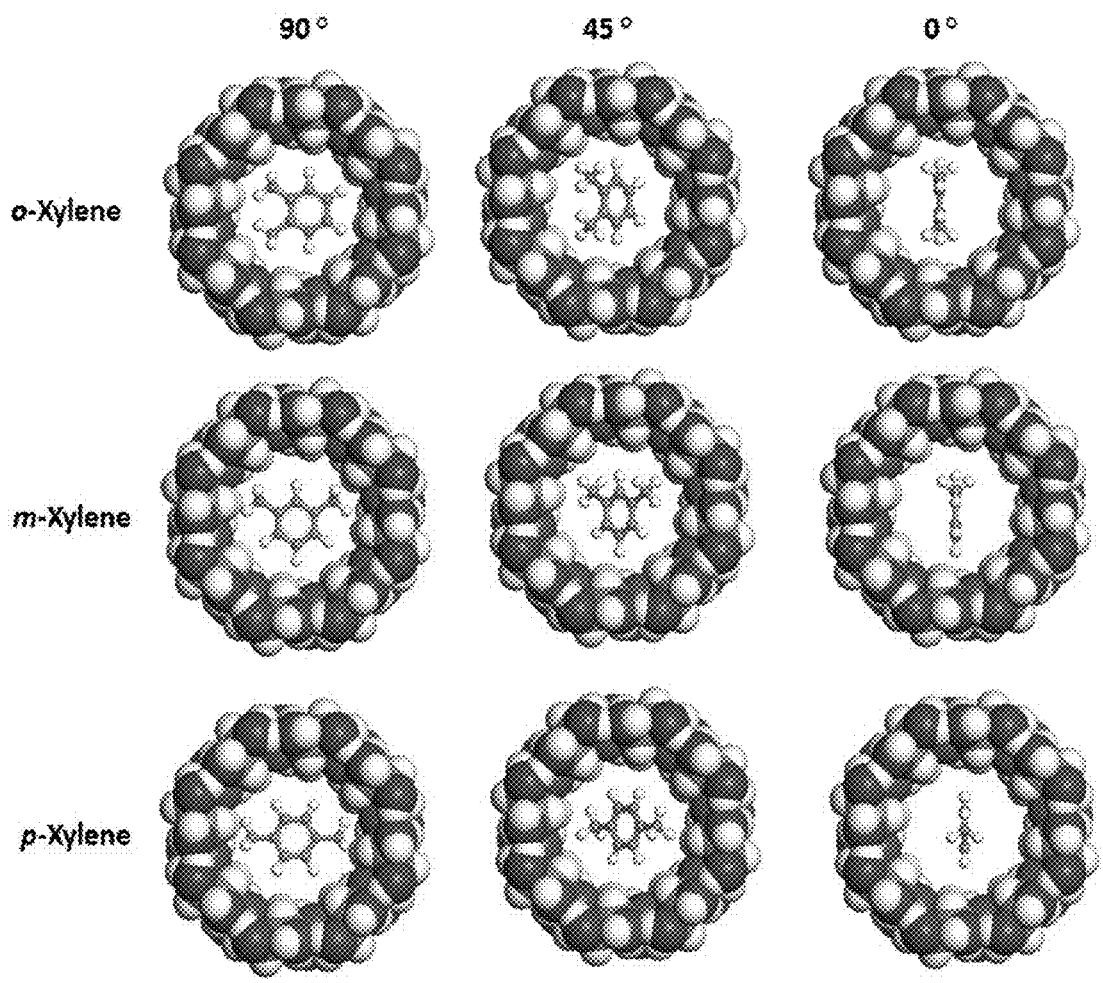
FIG. 21 depicts different orientations of xylene isomers inside the γ-CD rings.
Figure 22A:
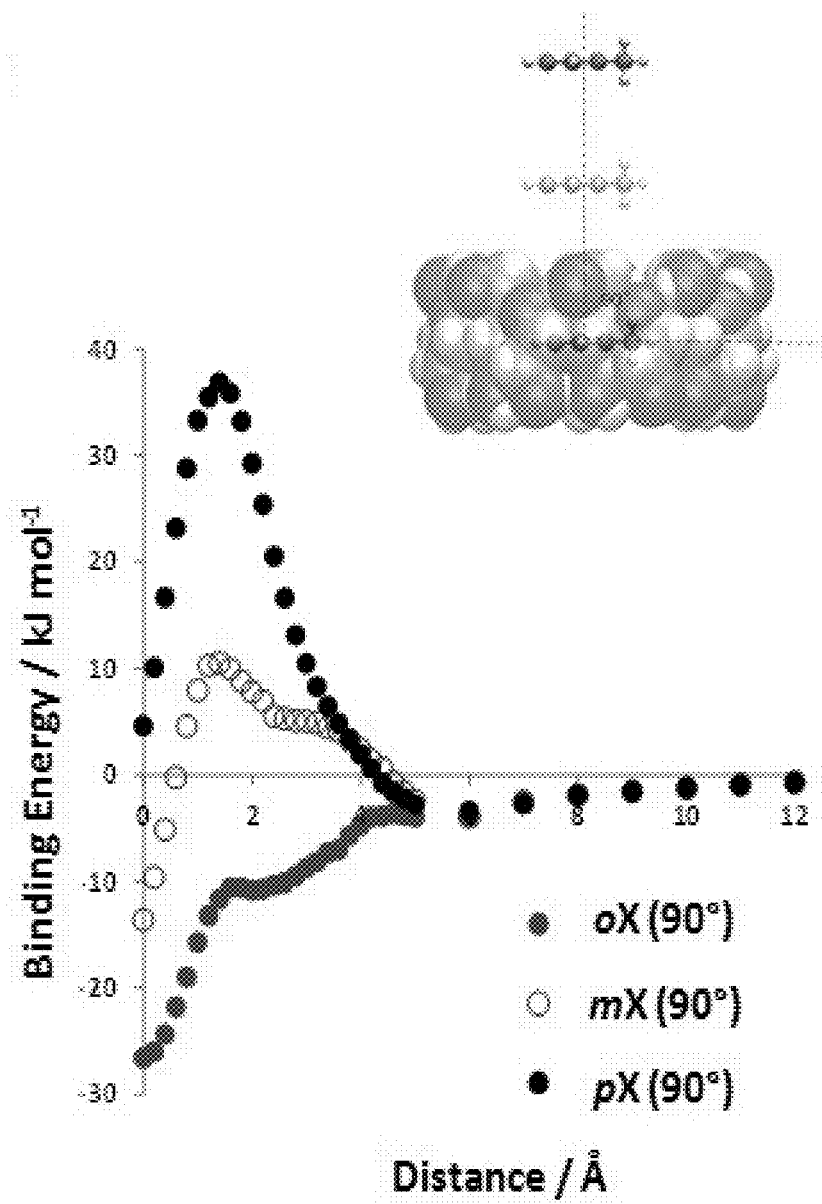
FIG. 22A depicts interaction energies for the xylene isomers for three different orientations of 90° with respect to the γ-CD ring. The schematic shows the scanned energy path for each orientation.
Figure 22B:
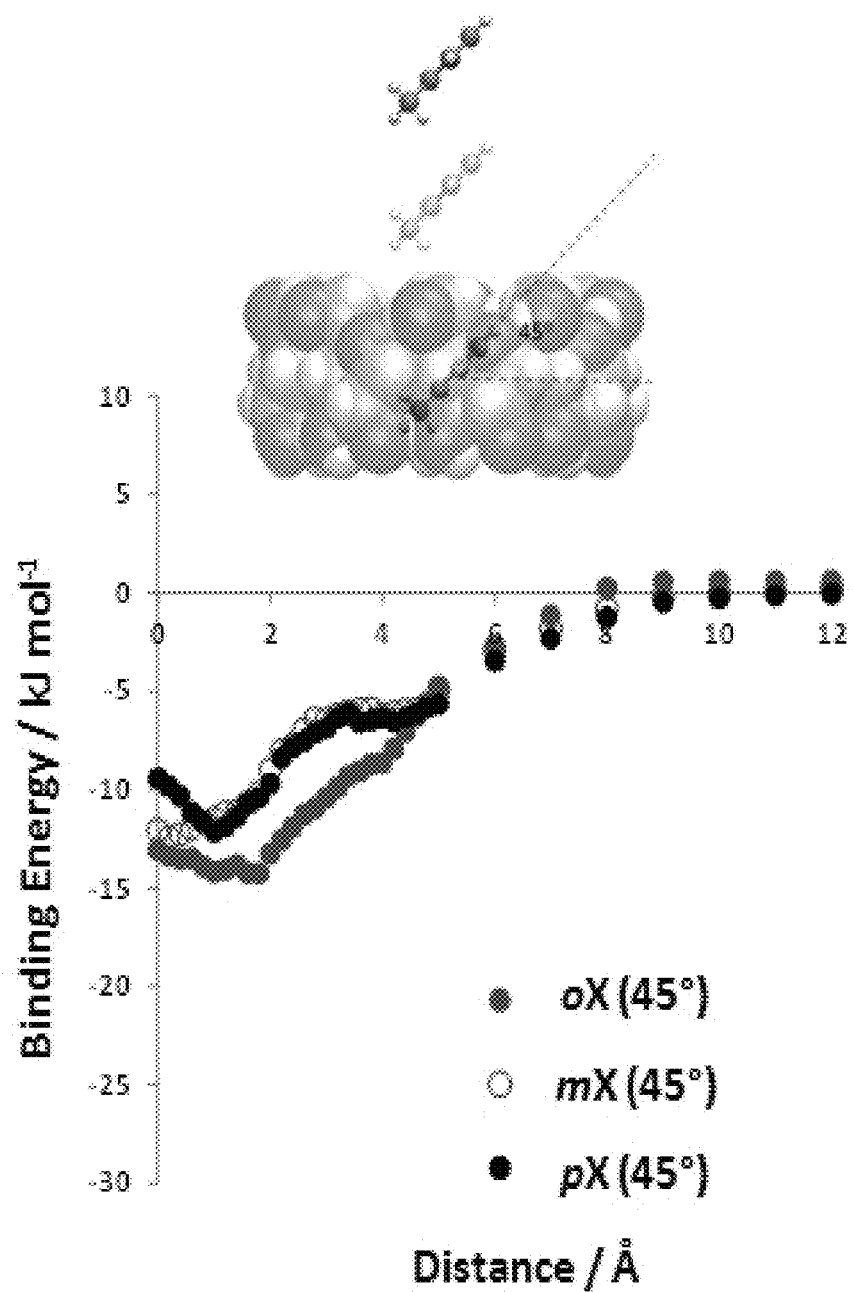
FIG. 22B depicts interaction energies for the xylene isomers for three different orientations of 45° with respect to the γ-CD ring. The schematic shows the scanned energy path for the orientation.
Figure 22C:
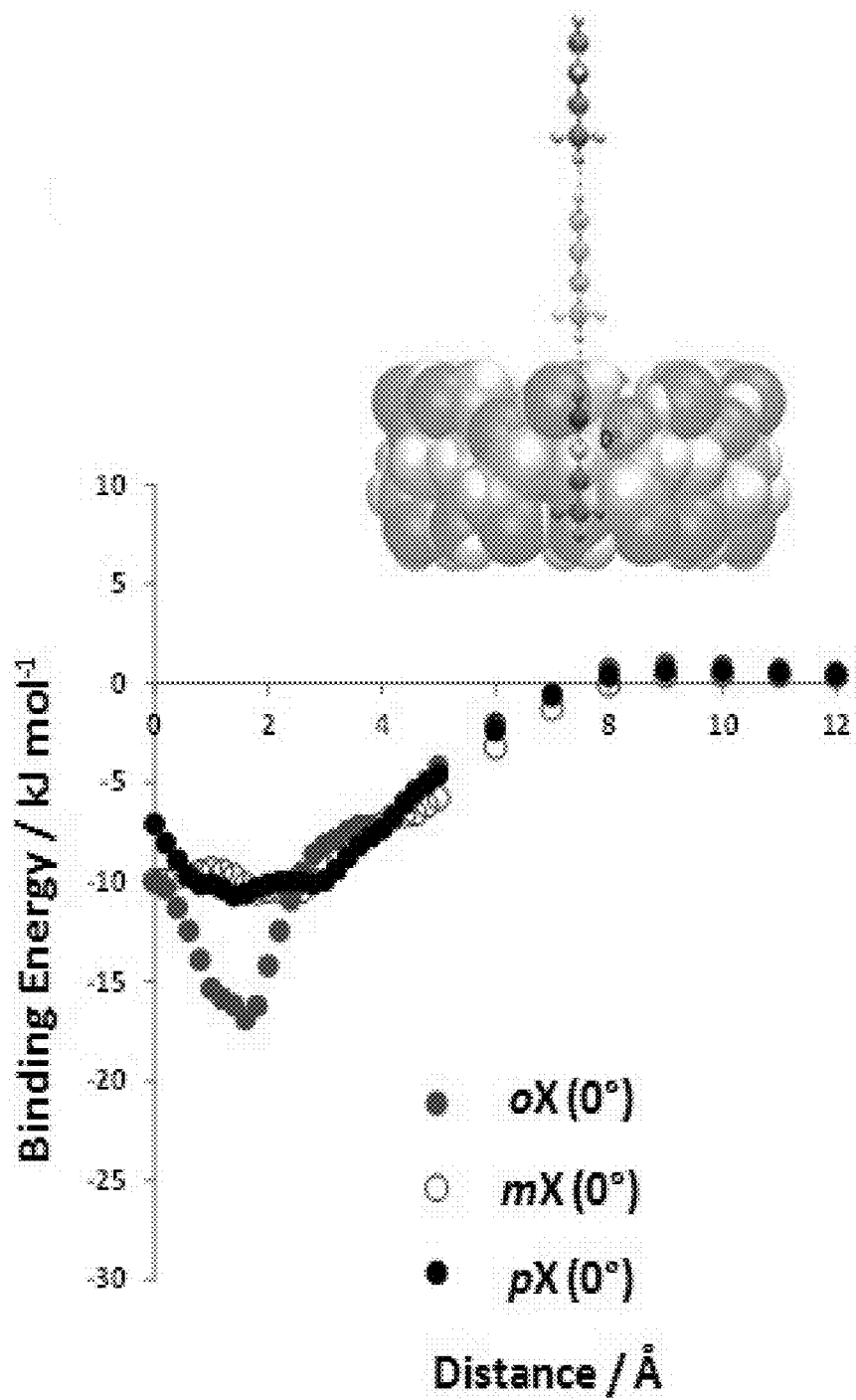
FIG. 22C depicts interaction energies for the xylene isomers for three different orientations of 0° with respect to the γ-CD ring. The schematic shows the scanned energy path for the orientation.

Single-point calculations at the M06/6-31G level of theory were performed for 32 points to sample interaction regions as each xylene isomer gradually moves away from the centre of γ-CD ring as represented in FIG. 21 and FIG. 22. In these calculations, the geometries of the γ-CD rings as well as the xylenes' geometries are held fixed at their isolated optimal geometries. To account for the orientation dependence of the binding energies, we repeated the above calculations for three different initial orientations of xylenes inside an isolated γ-CD ring. For each approach the orientation of xylene molecule is held fixed with respect to the γ-CD ring. All single point calculations were carried out with Gaussian 09 program package (Frisch, M. J.; Trucks, G. W.; Schlegel, H. B.; Scuseria, G. E.; Robb, M. A.; Cheeseman, J. R; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, J. A. Jr.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, M. J.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, Ö.; Foresman, J. B.; Ortiz, J. V.; Cioslowski, J.; Fox, D. J.; Gaussian, Inc., Wallingford Conn., (2009)).

Example 7

Vapor-Phase Adsorption Studies 7.1. Static Vapor Adsorption Studies

Single component isotherms were obtained for the adsorption of regioisomers of xylene on CD-MOF-2 in order to be able to investigate the mechanism of vapor-phase adsorption and separation. The mass relaxation profiles were analyzed with the Fickian, CBRD and stretched exponential (LDF) models in order to determine the rate limiting mass transfer step and also to determine diffusion coefficients.

7.1.1. Isotherms, Thermodynamics and Selectivities

Figure 23:
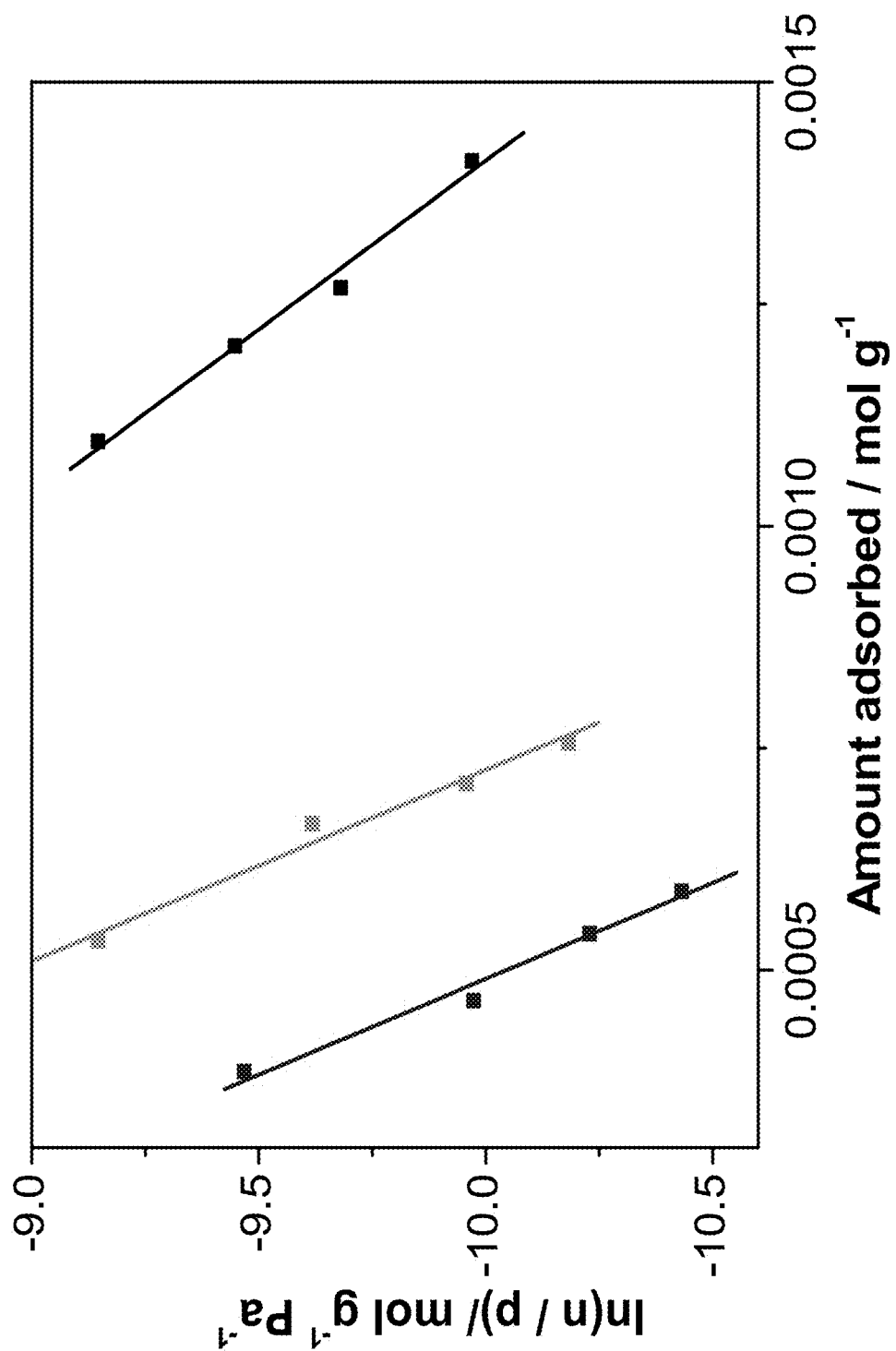
FIG. 23 depicts exemplary virial plots for the adsorption of xylene regioisomers on CD-MOF-2 in the low uptake region at 333 K, para-xylene (black), meta-xylene (green) and ortho-xylene (blue).

The adsorption isotherms (FIG. 23) were analyzed using virial analysis to determine adsorbate-adsorbate and adsorbate-adsorbent interactions (Table 16) and selectivity's (Table 17) based on Henry's Law, which is a fundamental measure of the interaction strength at zero surface coverage.

TABLE 16

Virial parameters for adsorption of xylene regioisomers on CD-MOF-2 at 333 K

| Regioisomer | $A_0$ (mol g$^{-1}$ Pa$^{-1}$) | $A_1$ (g mol$^{-1}$) | $K_H$ (×10$^{-3}$)/ (mol g$^{-1}$ Pa$^{-1}$) |
|---|---|---|---|
| Para-Xylene | −6.29 ± 0.26 | −2630.66 ± 209.09 | 1.86 |
| Meta-Xylene | −6.63 ± 0.34 | −4640.88 ± 498.74 | 1.31 |
| Ortho-Xylene | −7.73 ± 0.24 | −4627.51 ± 480.56 | 0.44 |

$A_0$ values are related to Henry's Law by the equation $KH=\exp(A_0)$, which quantifies the interaction strength at zero surface coverage.

TABLE 17

Xylene regioisomer selectivity on CD-MOF-2 based on Henry's constants at 333 K

| Ratio of Henry's constants | Selectivity |
|---|---|
| $K_{para}/K_{meta}$ | 1.42 |
| $K_{para}/K_{ortho}$ | 4.25 |
| $K_{meta}/K_{ortho}$ | 3.00 |

7.1.2. Adsorption Kinetics

Diffusion of molecules into pores may be influenced by molecular sieving through constrictions in the pore structure and surface chemistry and by surface diffusion via a site-to-site hopping mechanism. Molecular sieving depends on the critical dimension(s) of the adsorbate relative to the shape of the pore(s). In the case of slit shaped pores, one dimension is critical, whereas for pores with circular cross-section, two critical dimensions are significant. Surface diffusion is controlled by adsorbate-adsorbent and adsorbate-adsorbate interactions, and related to the enthalpy of adsorption.

Linear driving force (LDF) (Glueckauf, E.; Coates, J. I., *J. Chem. Soc.*, 1947, 1315; Glueckauf, E., *Trans. Faraday Soc.*, 1955, 51, 1540), combined barrier resistance/Fickian diffusion (Loughlin, K. F.; Hassan, M. M.; Fatehi, A. I.; Zahur, M., *Gas Sep. Purif.*, 1993, 7, 264), Fickian (Crank, J., *The mathematics of diffusion*; 2nd ed.; Clarendon Press: Oxford, 1975) and stretched exponential (Klafter, J.; Shlesinger, M. F., *Proc. Natl. Acad. Sci. U.S.A*, 1986, 83, 848) models have been used to describe diffusion of molecules into porous particles. Surface diffusion of molecules is an activated process involving hopping between adjacent sites and is affected by interaction between the adsorbed molecule and surface sites. In the case of small pores electrostatic interaction and steric effects become important and, may result in very large differences in molecular diffusivity for similar molecules. Klafter and Shlesinger showed (Klafter, J.; Shlesinger, M. F., *Proc. Natl. Acad. Sci. U.S.A*, 1986, 83, 848)) that the stretched exponential model is a common underlying mathematical structure relating the Forster direct-transfer mechanism (Forster, T., *Z. Naturforsch. Teil A*, 1949, 4, 321), which involves relaxation via parallel channels and the serial hierarchically constrained dynamics (Palmer, R. G.; Stein, D. L.; Abrahams, E.; Anderson, P. W., *Phys. Rev. Lett.*, 1984, 53, 958) and defect-diffusion models (Glarum, S. H., *J. Chem. Phys.*, 1960, 33, 1371; Bordewijk, P., *Chem. Phys. Lett.*, 1975, 32, 592; Shlesinger, M. F.; Montroll, E. W., *Proceedings of the National Academy of Sciences of the United States of America-Physical Sciences*, 1984, 81, 1280). The unifying mathematical feature of the models is a scale-invariant distribution of relaxation times. Surface diffusion of molecules constrained in pores has similar characteristics. The stretched exponential (SE) model is described by the following equation (4):

$$\frac{M_t}{M_e} = 1 - e^{-(kt)^\beta} \quad (4)$$

where $M_t$ is the mass at time t, $M_e$ is the mass at equilibrium, k is the mass transfer rate constant (s$^{-1}$) and t is the time(s). The exponent parameter β equilibrium is material dependent and reflects the width of the distribution of relaxation times. The SE model is 3-dimensional with a single relaxation time when β=1 (Linear Driving Force (LDF) model) ( ) and 1-dimensional with a distribution of relaxation times when β=0.5.

There are similarities in models based on molecular surface diffusion and macroscopic diffusion into particles. The stretched exponential model can describe the range of kinetic profiles with the exponent β quantifying the shape of the kinetic profile in comparison to Fickian (β~0.65 for spherical particles) and LDF (β=1). Furthermore, the SE model also provides a good description of Fickian diffusion into a one-dimensional slab of cylindrical particles. A stretched exponential model has been used to describe the adsorption and desorption kinetics of a wide range of gases and vapors on metal organic framework materials (Chen, B.; Zhao, X.; Putkham, A.; Hong, K.; Lobkovsky, E. B.; Hurtado, E. J.; Fletcher, A. J.; Thomas, K. M., *J. Am. Chem. Soc.*, 2008, 130, 6411; Fletcher, A. J.; Cussen, E. J.; Bradshaw, D.; Rosseinsky, M. J.; Thomas, K. M., *J. Am. Chem. Soc.*, 2004, 126, 9750) and activated carbons (Fletcher, A. J.; Thomas, K. M., *J. Phys. Chem. C*, 2007, 111, 2107; Fletcher, A. J.; Yuzak, Y.; Thomas, K. M., *Carbon*, 2006, 44, 989; Bell, J. G.; Zhao, X.; Uygur, Y.; Thomas, K. M., *J. Phys. Chem. C*, 2011, 115, 2776; Zhao, X.; Villar-Rodil, S.; Fletcher, A. J.; Thomas, K. M., *J. Phys. Chem. B*, 2006, 110, 9947). Hence, the SE model has a wide applicability for studying adsorption dynamics for porous materials with widely different particle shapes. This model can serve as a link between models based diffusion into particles and surface diffusion of molecules with a hierarchical scale invariant properties.

Previous studies of MOFs with windows in pores has shown that the adsorption kinetics can be described by either double exponential or double stretched exponential models corresponding to two processes a) diffusion through barriers due to narrow windows with a high activation energy and b) diffusion along the pores with a lower barrier to diffusion (Fletcher, A. J.; Cussen, E. J.; Bradshaw, D.; Rosseinsky, M. J.; Thomas, K. M., *J. Am. Chem. Soc.*, 2004, 126, 9750; Fletcher, A. J.; Cussen, E. J.; Prior, T. J.; Rosseinsky, M. J.; Kepert, C. J.; Thomas, K. M., *J. Am. Chem. Soc.*, 2001, 123, 10001) and also, diffusion along two types of pores with different shapes (Chen, B.; Zhao, X.; Putkham, A.; Hong, K.; Lobkovsky, E. B.; Hurtado, E. J.; Fletcher, A. J.; Thomas, K. M., *J. Am. Chem. Soc.*, 2008, 130, 6411).

In real systems, particle size distributions and irregular particle shapes may make the determination of diffusion coefficients difficult. The kinetic profiles for each adsorption isotherm pressure increment were measured for small pressure increments where the diffusivities may be considered constant, to understand the dynamics associated with the adsorption isotherms. All kinetic profiles were initially fit using the SE model. Based on the values of the exponent, the Fickian, CBRD or LDF mass transfer model was used in order to determine the diffusion coefficients.

The LDF model describes the adsorption/desorption kinetic profiles when diffusion through a surface layer is the rate determining process and is described by the following equation (5):

$$\frac{M_t}{M_e} = 1 - e^{-kt}, \tag{5}$$

where Mt is mass uptake at time t, Me is mass uptake at equilibrium and k is the mass transfer rate constant. The adsorption kinetics can be compared using the rate constants (k) determined either from the gradients of graphs of ln(1−Mt/Me) versus time or by fitting the adsorption uptake curves to equation (5). The values of the LDF intraparticle mass transfer coefficient (k) can be converted to effective intraparticle diffusion coefficients (Dc) using the equation (6) below (LeVan, M. D., *Adsorption Science and Technology, NATO ASI Series E Applied Science*; A. E. Rodriguez, LeVan, M. D., Eds.; Kluwer: Dordrecht, 1989, 158, 149):

$$k = 15D_c/r^2 \tag{6}$$

where r is the radius of the particle.

Diffusivity is measured when internal diffusion controls the adsorption process. Fick's law for isothermal diffusion into a homogeneous sphere is given by the following equation (7) (S21):

$$\frac{M_t}{M_e} = 1 - \frac{6}{\pi^2}\sum_{n=1}^{\infty}\left(\frac{1}{n^2}\right)\exp\left(\frac{-Dn^2\pi^2 t}{r^2}\right) \tag{7}$$

where Mt is mass uptake at time t, Me is mass uptake at equilibrium, D is diffusivity and r is radius of the particle. The series in the above equation converges very rapidly and a graph of ln(1−Mt/Me) versus time is close to linearity in the uptake region Mt/Me>0.6. Therefore, the graph only differs from the LDF model in the initial uptake region where Mt/Me<0.6. Fickian diffusion was only observed for para-xylene adsorption on CD-MOF-2 at low pressure.

The combined barrier resistance/diffusion (CBRD) model is based on the assumption of the presence of a surface barrier resistance and subsequent diffusion in a spherical microporous system by Fick's law. The partial differential equation (8), initial condition and boundary conditions for isothermal diffusion into a spherical particle are as follows (Loughlin, K. F.; Hassan, M. M.; Fatehi, A. I.; Zahur, M., *Gas Sep. Purif.*, 1993, 7, 264):

$$\frac{\partial C}{\partial t} = D\left[\left(\frac{\partial^2 C}{\partial r^2}\right) + \left(\frac{2}{r}\right)\left(\frac{\partial C}{\partial r}\right)\right] \tag{8}$$

where D is the crystallite diffusivity (cm$^2$ s$^{-1}$), C is the sorbate concentration in the crystallite (mmol m$^{-3}$), r), r is the radial co-ordinate and t is the time. The initial condition is $$C(r,0) = 0 \tag{9}.$$

The boundary condition at the surface of the particle is $$D\frac{\partial C(r_S t)}{\partial r} = k_b(C*(t) - C(r,t)), \tag{10}$$

while the boundary condition at the center is $$\frac{\partial C(r_c t)}{\partial r} = 0, \tag{11}$$

where D is the crystallite diffusivity (m$^2$ s$^{-1}$), kb is the surface barrier resistance (m s$^{-1}$), r), r is the radial co-ordinate, rs is the surface radial co-ordinate and rc is the center radial co-ordinate (m), t is time(s), C is the sorbate concentration in the crystallite (mol m$^{-3}$) and C* the surface concentration in equilibrium with the gas phase (mol m$^{-3}$). The parameters derived from the model are kb the barrier resistance constant and kd resistance due to diffusion in the pores. The partial differential equation was solved using MATLAB with PDEPE solver coupled with a non-linear least squares function in order to fit the PDE solution to the experimental kinetic profiles. The adjustable parameters were the diffusion coefficient kD and the surface barrier resistance constant kB.

The diffusion coefficients and surface barrier resistance constants for Fickian, CBRD and LDF for para-, meta-, and ortho-xylene vapor adsorption on CD-MOF-2 at 333 K are summarized in Tables 18, 19 and 20, respectively.

TABLE 18

Diffusion coefficients and surface barrier resistance constants for Fickian, CBRD and LDF for para-xylene vapor adsorption on CD-MOF-2 at 333 K.

| Pressure/ mbar | Amount Adsorbed/ mmol g$^{-1}$ | Diffusion Coefficient (D)/(m$^2$ s$^{-1}$) | Surface Barrier from CBRD model/k$_b$ (m s$^{-1}$) | Mass transfer model |
|---|---|---|---|---|
| 0.052 | 0.686 | | | UMP |
| 0.103 | 1.096 | | | UMP |
| 0.152 | 1.203 | 8.00 × 10$^{-11}$ | | FD |
| 0.203 | 1.269 | 2.74 × 10$^{-10}$ | 2.20 × 10$^{-5}$ | CBRD |
| 0.302 | 1.412 | 1.80 × 10$^{-10}$ | 6.45 × 10$^{-6}$ | CBRD |
| 0.402 | 1.556 | 4.04 × 10$^{-10}$ | 2.02 × 10$^{-6}$ | CBRD |
| 0.502 | 1.867 | | | UMP |
| 0.602 | 2.190 | 1.96 × 10$^{-10}$ | | LDF |
| 0.702 | 2.440 | 2.63 × 10$^{-10}$ | | LDF |
| 0.803 | 2.526 | | | UMP |
| 1.003 | 2.617 | 1.36 × 10$^{-9}$ | | LDF |
| 1.502 | 2.694 | 2.10 × 10$^{-9}$ | | LDF |
| 1.983 | 2.738 | | | UMP |
| 2.487 | 2.770 | | | UMP |

TABLE 19

Diffusion coefficients and surface barrier resistance constants for Fickian, CBRD and LDF for meta-xylene vapor adsorption on CD-MOF-2 at 333 K.

| Pressure/ mbar | Amount Adsorbed/ mmol g$^{-1}$ | Diffusion Coefficient (D)/ (m$^2$ s$^{-1}$) | Surface barrier from CBRD model/ k$_b$ (m s$^{-1}$) | Mass transfer model |
|---|---|---|---|---|
| 0.050 | 0.533 | 6.56 × 10$^{-11}$ | 9.26 × 10$^{-7}$ | CBRD |
| 0.100 | 0.665 | 5.86 × 10$^{-10}$ | | LDF |
| 0.150 | 0.710 | 6.70 × 10$^{-10}$ | | LDF |

TABLE 19-continued

Diffusion coefficients and surface barrier resistance constants for Fickian, CBRD and LDF for meta-xylene vapor adsorption on CD-MOF-2 at 333 K.

| Pressure/ mbar | Amount Adsorbed/ mmol g$^{-1}$ | Diffusion Coefficient (D)/ (m$^2$ s$^{-1}$) | Surface barrier from CBRD model/ $k_b$ (m s$^{-1}$) | Mass transfer model |
|---|---|---|---|---|
| 0.200 | 0.756 | 5.70 × 10$^{-10}$ | | LDF |
| 0.300 | 0.852 | 4.49 × 10$^{-10}$ | | LDF |
| 0.400 | 0.957 | 3.49 × 10$^{-10}$ | | LDF |
| 0.500 | 1.125 | | | UMP |
| 0.600 | 1.255 | | | UMP |
| 0.700 | 1.309 | 4.36 × 10$^{-10}$ | 5.37 × 10$^{-6}$ | CBRD |
| 0.800 | 1.354 | 4.36 × 10$^{-10}$ | 5.32 × 10$^{-6}$ | CBRD |
| 1.000 | 1.424 | 6.78 × 10$^{-10}$ | | LDF |
| 1.500 | 1.641 | | | UMP |
| 1.989 | 2.440 | 2.45 × 10$^{-10}$ | | LDF |
| 2.493 | 2.656 | 5.74 × 10$^{-10}$ | | LDF |
| 2.995 | 2.732 | | | UMP |

TABLE 20

Diffusion coefficients and surface barrier resistance constants for Fickian, CBRD and LDF for ortho-xylene vapor adsorption on CD-MOF-2 at 333 K.

| Pressure/ mbar | Amount Adsorbed/ mmol g$^{-1}$ | Diffusion Coefficient (D)/ (m$^2$ s$^{-1}$) | Surface barrier from CBRD model/ $k_b$ (m s$^{-1}$) | Mass transfer model |
|---|---|---|---|---|
| 0.050 | 0.386 | 7.96 × 10$^{-11}$ | | LDF |
| 0.100 | 0.466 | 1.27 × 10$^{-10}$ | 2.90 × 10$^{-6}$ | CBRD |
| 0.200 | 0.589 | 2.55 × 10$^{-10}$ | | LDF |
| 0.300 | 0.718 | 1.47 × 10$^{-10}$ | | LDF |
| 0.400 | 0.830 | 1.49 × 10$^{-10}$ | | LDF |
| 0.500 | 0.927 | 1.43 × 10$^{-10}$ | | LDF |
| 0.600 | 1.006 | 1.76 × 10$^{-10}$ | | LDF |
| 0.700 | 1.067 | 1.69 × 10$^{-10}$ | | LDF |
| 0.799 | 1.119 | 2.08 × 10$^{-10}$ | | LDF |
| 1.000 | 1.214 | 1.96 × 10$^{-10}$ | | LDF |
| 1.499 | 1.420 | 1.76 × 10$^{-10}$ | | LDF |
| 1.994 | 2.487 | 8.78 × 10$^{-11}$ | | LDF |
| 2.989 | 2.639 | 5.60 × 10$^{-10}$ | 4.37 × 10$^{-6}$ | CBRD |
| 3.495 | 2.667 | 6.43 × 10$^{-10}$ | | LDF |

7.2. Breakthrough Data

Figure 24:
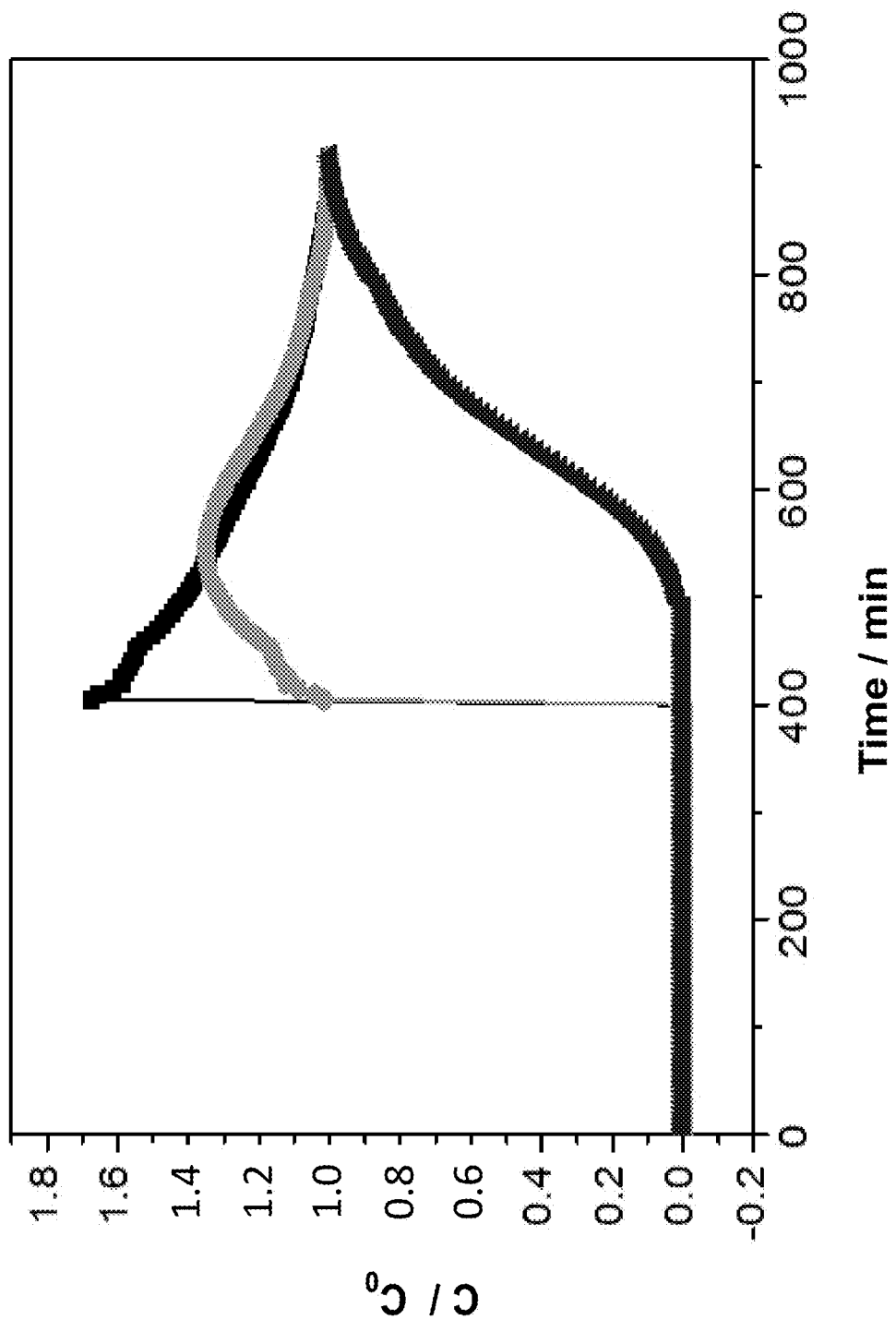
FIG. 24 depicts an exemplary concentration plot of the vapor-phase breakthrough experiment for xylene isomers at 333 K using $N_2$ as the carrier gas at 20 mL $min^{-1}$ through a CD-MOF-2 column, para-xylene (black), meta-xylene (green) and ortho-xylene (blue).

Breakthrough experiments were carried out in a 4-mm glass U-tube with CD-MOF-2 crystals. CD-MOF-2 (1.46 g) was used to fill the tube at a length of 16 cm. The sample was purged with dry $N_2$ at 333 K overnight to ensure the complete activation of the sample prior to breakthrough measurements. Dry $N_2$ at a rate of 20 mL min$^{-1}$ was bubbled through a mixture of xylene isomers (15 mL each) at atmospheric pressure. The effluent was passed through a VICI Valco 6-way sampling valve. An aliquot (0.25 mL) of gas was sampled every 5 min and delivered to a Perkin Elmer Clarus 500 Gas Chromatograph fitted with a Supelco SCOT capillary GC column (Sigma-Aldrich 23813-U, 50 ft long, 0.02 in. outside diameter) maintained at 363 K. The analyses were performed using an injector and detector (FID) temperature of 493 K and $N_2$ was used as the carrier gas that was maintained at an inlet pressure of 1.5 psi with a split ratio of 10:1. Baseline separation of xylene isomers was achieved and all peaks were easily integrated in the resulting GC trace shown in FIG. 24.

REFERENCES (1) (a) Hoskins, B. F.; Robson, R. J. Am. Chem. Soc. 1989, 111, 5962. (b) Hoskins, B. F.; Robson, R. J. Am. Chem. Soc. 1990, 112, 1546. (c) Fujita, M.; Kwon, Y. J.; Washizu, S.; Ogura, K. J. Am. Chem. Soc. 1994, 116, 1151. (d) Li, H.; Eddaoudi, M.; O'Keeffe, M.; Yaghi, O. M. Nature 1999, 402, 276. (e) Eddaoudi, M.; Moler, D. B.; Li, H.; Chen, B.; Reineke, T. M.; O'Keeffe, M.; Yaghi, O. M. Acc. Chem. Res. 2001, 34, 319. (f) Moulton, B.; Zaworotko, M. J. Chem. Rev. 2001, 101, 1629. (g) Eddaoudi, M.; Kim, J.; Rosi, N.; Vodak, D.; Wachter, J.; O'Keeffe, M.; Yaghi, O. M. Science 2002, 295, 469. (h) Kitagawa, S.; Kitaura, R.; Noro, S.-i. Angew. Chem., Int. Ed. 2004, 43, 2334. (i) Ferey, G. Chem. Soc. Rev. 2008, 37, 191. (j) Han, S.; Wei, Y.; Valente, C.; Forgan, R. S.; Gassensmith, J. J.; Smaldone, R. A.; Nakanishi, H.; Coskun, A.; Stoddart, J. F.; Grzybowski, B. A. Angew. Chem., Int. Ed. 2011, 50, 276. (k) Wei, Y.; Han, S.; Walker, D. A.; Fuller, P. E.; Grzybowski, B. A. Angew. Chem., Int. Ed. 2012, 51, 7435. (l) Bernini, M. C.; Jimenez, D. F.; Pasinetti, M.; Ramirez-Pastor, A. J.; Snurr, R. Q. J. Mater. Chem. B 2014, 2, 766. (m) Yoon, S. M.; Warren, S. C.; Grzybowski, B. A. Angew. Chem., Int. Ed. 2014, 53, 4437. (n) Fracaroli, A. M.; Furukawa, H.; Suzuki, M.; Dodd, M.; Okajima, S.; Gańdara, F.; Reimer, J. A.; Yaghi, O. M. J. Am. Chem. Soc. 2014, 136, 8863. (o) Furukawa, H.; Mueller, U.; Yaghi, O. M. Angew. Chem., Int. Ed. 2015, 54, 3417. (p) Fei, H.; Cohen, S. M. J. Am. Chem. Soc. 2015, 137, 2191.

(2) (a) Dinca; M.; Yu, A. F.; Long, J. R. J. Am. Chem. Soc. 2006, 128, 8904. (b) Latroche, M.; Surblé, S.; Serre, C.; Mellot-Draznieks, C.; Llewellyn, P. L.; Lee, J.-H.; Chang, J.-S.; Jhung, S. H.; Férey, G. Angew. Chem., Int. Ed. 2006, 45, 8227. (c) Liu, Y.; Eubank, J. F.; Cairns, A. J.; Eckert, J.; Kravtsov, V. C.; Luebke, R.; Eddaoudi, M. Angew. Chem., Int. Ed. 2007, 46, 3278. (d) Murray, L. J.; Dinca, M.; Long, J. R. Chem. Soc. Rev. 2009, 38, 1294. (e) Farha, O. K.; Eryazici, I.; Jeong, N. C.; Hauser, B. G.; Wilmer, C. E.; Sarjeant, A. A.; Snurr, R. Q.; Nguyen, S. T.; Yazaydin, A. O; Hupp, J. T. J. Am. Chem. Soc. 2012, 134, 15016. (f) Wang, H.; Cao, D. J. Phys. Chem. C 2015, 119, 6324. (g) Zhao, X.; Bu, X.; Zhai, Q. C.; Tran, H.; Feng, P. J. Am. Chem. Soc. 2015, 137, 1396.

(3) (a) Fletcher, A. J.; Thomas, K. M.; Rosseinsky, M. J. J. Solid State Chem. 2005, 178, 2491. (b) Matsuda, R.; Kitaura, R.; Kitagawa, S.; Kubota, Y.; Belosludov, R. V.; Kobayashi, T. C.; Sakamoto, H.; Chiba, T.; Takata, M.; Kawazoe, Y.; Mita, Y. Nature 2005, 436, 238. (c) Hayashi, H.; Cote, A. P.; Furukawa, H.; O'Keeffe, M.; Yaghi, O. M. Nat. Mater. 2007, 6, 501. (d) Keskin, S.; Sholl, D. S. J. Phys. Chem. C 2007, 111, 14055. (e) Li, B.; Wen, H.-M.; Wang, H.; Wu, H.; Tyagi, M.; Yildirim, T.; Zhou, W.; Chen, B. J. Am. Chem. Soc. 2014, 136, 6207. (f) Hu, J.; Sun, T.; Ren, X.; Wang, S. Microporous Mesoporous Mater. 2015, 204, 73.

(4) (a) Demessence, A.; D'Alessandro, D. M.; Foo, M. L.; Long, J. R. J. Am. Chem. Soc. 2009, 131, 8784. (b) Zheng, B.; Bai, J.; Duan, J.; Wojtas, L.; Zaworotko, M. J. J. Am. Chem. Soc. 2010, 133, 748. (c) Goeppert, A.; Czaun, M.; Surya Prakash, G. K.; Olah, G. A. Energy Environ. Sci. 2012, 5, 7833. (d) Yang, S.; Lin, X.; Lewis, W.; Suyetin, M.; Bichoutskaia, E.; Parker, J. E.; Tang, C. C.; Allan, D. R.; Rizkallah, P. J.; Hubberstey, P.; Champness, N. R.; Mark Thomas, K.; Blake, A. J.; Schroder, M. Nat. Mater. 2012, 11, 710. (e) Beyzavi, M. H.; Klet, R. C.; Tussupbayev, S.; Borycz, J.; Vermeulen, N. A.; Cramer, C. J.; Stoddart, J. F.; Hupp, J. T.; Farha, O. K. J. Am. Chem. Soc. 2014, 136, 15861. (f) Gassensmith, J. J.; Kim, J. Y.; Holcroft, J. M.; Farha, O. K.; Stoddart, J. F.; Hupp, J. T.; Jeong, N. C. J. Am. Chem. Soc. 2014, 136, 8277. (g) Sato, H.; Kosaka, W.; Matsuda, R.; Hori, A.; Hijikata, Y.; Belosludov, R. V.;

Sakaki, S.; Takata, M.; Kitagawa, S. Science 2014, 343, 167. (h) Al-Maythalony, B. A.; Shekhah, O.; Swaiden, R.; Belmabkhout, Y.; Pinnau, I.; Eddaoudi, M. J. Am. Chem. Soc. 2015, 137, 1754.

(5) (a) Maes, M.; Alaerts, L.; Vermoortele, F.; Ameloot, R.; Couck, S.; Finsy, V.; Denayer, J. F. M.; De Vos, D. E. J. Am. Chem. Soc. 2010, 132, 2284. (b) Herm, Z. R.; Wiers, B. M.; Mason, J. A.; van Baten, J. M.; Hudson, M. R.; Zajdel, P.; Brown, C. M.; Masciocchi, N.; Krishna, R.; Long, J. R. Science 2013, 340, 960.

(6) (a) Bradshaw, D.; Prior, T. J.; Cussen, E. J.; Claridge, J. B.; Rosseinsky, M. J. J. Am. Chem. Soc. 2004, 126, 6106. (b) Vaidhyana-than, R.; Bradshaw, D.; Rebilly, J.-N.; Barrio, J. P.; Gould, J. A.; Berry, N. G.; Rosseinsky, M. J. Angew. Chem., Int. Ed. 2006, 45, 6495. (c) Nuzhdin, A. L.; Dybtsev, D. N.; Bryliakov, K. P.; Talsi, E. P.; Fedin, V. P. J. Am. Chem. Soc. 2007, 129, 12958. (d) Liu, Y.; Xuan, W.; Cui, Y. Adv. Mater. 2010, 22, 4112. (e) Padmanaban, M.; Muller, P.; Lieder, C.; Gedrich, K.; Grunker, R.; Bon, V.; Senkovska, I.; Baumgartner, S.; Opelt, S.; Paasch, S.; Brunner, E.; Glorius, F.; Klemm, E.; Kaskel, S. Chem. Commun. 2011, 47, 12089. (f) Das, M. C.; Guo, Q.; He, Y.; Kim, J.; Zhao, C.-G.; Hong, K.; Xiang, S.; Zhang, Z.; Thomas, K. M.; Krishna, R.; Chen, B. J. Am. Chem. Soc. 2012, 134, 8703. (g) Wang, W.; Dong, X.; Nan, J.; Jin, W.; Hu, Z.; Chen, Y.; Jiang, J. Chem. Commun. 2012, 48, 7022. (h) Kuang, X.; Ma, Y.; Su, H.; Zhang, J.; Dong, Y.-B.; Tang, B. Anal. Chem. 2013, 86, 1277.

(7) (a) Mueller, U.; Schubert, M.; Teich, F.; Puetter, H.; Schierle-Arndt, K.; Pastre, J. J. Mater. Chem. 2006, 16, 626. (b) Li, J.-R.; Kuppler, R. J.; Zhou, H.-C. Chem. Soc. Rev. 2009, 38, 1477. (c) Jiang, H.-L.; Xu, Q. Chem. Commun. 2011, 47, 3351. (d) Lee, C. Y.; Bae, Y.-S.; Jeong, N. C.; Farha, 0. K.; Sarjeant, A. A.; Stern, C. L.; Nickias, P.; Snurr, R. Q.; Hupp, J. T.; Nguyen, S. T. J. Am. Chem. Soc. 2011, 133, 5228. (e) Bloch, E. D.; Queen, W. L.; Krishna, R.; Zadrozny, J. M.; Brown, C. M.; Long, J. R. Science 2012, 335, 1606. (f) He, Y.; Zhang, Z.; Xiang, S.; Fronczek, F. R.; Krishna, R.; Chen, B. Chem. Commun. 2012, 48, 6493.

(8) Keskin, S.; Kizilel, S. Ind. Eng. Chem. Res. 2011, 50, 1799.

(9) (a) Hulme, R.; Rosensweig, R. E.; Ruthven, D. M. Ind. Eng. Chem. Res. 1991, 30, 752. (b) Cottier, V.; Bellat, J.-P.; Simonot-Grange, M.-H.; Methivier, A. J. Phys. Chem. B 1997, 101, 4798. (c) Kulprathipanja, S. J.; James, R. B. Zeolites in Industrial Separation; Wiley-VCH: Weinheim, 2010. (d) Jee, S. E.; Sholl, D. S. J. Am. Chem. Soc. 2009, 131, 7896.

(10) (a) Cheremisinoff, P. N.; Ellerbush, F. Carbon Adsorption Handbook; Ann Arbor Science Publishers: Ann Arbor, Mich., 1978. (b) Mattson, J. S. M., Mark, H. B. Activated Carbon; Marcel Dekker: New York, 1971.

(11) (a) Ferey, G.; Serre, C. Chem. Soc. Rev. 2009, 38, 1380. (b) O'Keeffe, M. Chem. Soc. Rev. 2009, 38, 1215.

(12) (a) Minceva, M.; Rodrigues, A. E. AIChE J. 2007, 53, 138. (b) Othmer, K. Separation Technology, 2nd ed.; Wiley: Hoboken, N.J., 2008; two-volume set, Vol. 1.

(13) (a) Broughton, D. B.; Gerhold, C. G. U.S. Pat. No. 2,985,589, 1961. (b) Eccli, W. D.; Fremuth, A. D. S. U.S. Pat. No. 5,498,822A, 1996. (c) Lima, R. M.; Grossmann, I. E. AIChE J. 2009, 55, 354.

(14) Minceva, M.; Rodrigues, A. E. Chem. Eng. Res. Des. 2004, 82, 667.

(15) (a) Lindley, J.; McLeod, A. J. U.S. Pat. No. 3,959, 978A, 1976. (b) Hubbell, D. S.; Rutten, P. W. M., Patent: U.S. Pat. No. 5,811,629A, 1998.

(16) Lusi, M.; Barbour, L. J. Angew. Chem., Int. Ed. 2012, 51, 3928.

(17) (a) Tozawa, T.; Jones, J. T. A.; Swamy, S. I.; Jiang, S.; Adams, D. J.; Shakespeare, S.; Clowes, R.; Bradshaw, D.; Hasell, T.; Chong, S. Y.; Tang, C.; Thompson, S.; Parker, J.; Trewin, A.; Bacsa, J.; Slawin, A. M. Z.; Steiner, A.; Cooper, A. I. Nat. Mater. 2009, 8, 973. (b) Mitra, T.; Jelfs, K. E.; Schmidtmann, M.; Ahmed, A.; Chong, S. Y.; Adams, D. J.; Cooper, A. I. Nat. Chem. 2013, 5, 276.

(18) (a) Munch, A. S.; Mertens, F. O. R. L. J. Mater. Chem. 2012, 22, 10228. (b) Sarkisov, L. Phys. Chem. Chem. Phys. 2012, 14, 15438.

(19) Luebbers, M. T.; Wu, T.; Shen, L.; Masel, R. I. Langmuir 2010, 26, 11319.

(20) Alaerts, L.; Kirschhock, C. E. A.; Maes, M.; van der Veen, M. A.; Finsy, V.; Depla, A.; Martens, J. A.; Baron, G. V.; Jacobs, P. A.; Denayer, J. F. M.; De Vos, D. E. Angew. Chem., Int. Ed. 2007, 46, 4293.

(21) Alaerts, L.; Maes, M.; Giebeler, L.; Jacobs, P. A.; Martens, J. A.; Denayer, J. F. M.; Kirschhock, C. E. A.; De Vos, D. E. J. Am. Chem. Soc. 2008, 130, 14170.

(22) Alaerts, L.; Maes, M.; Jacobs, P. A.; Denayer, J. F. M.; De Vos, D. E. Phys. Chem. Chem. Phys. 2008, 10, 2979.

(23) Maes, M.; Vermoortele, F.; Boulhout, M.; Boudewijns, T.; Kirschhock, C.; Ameloot, R.; Beurroies, I.; Denoyel, R.; De Vos, D. E. Microporous Mesoporous Mater. 2012, 157, 82.

(24) Remy, T.; Ma, L.; Maes, M.; De Vos, D. E.; Baron, G. V.; Denayer, J. F. M. Ind. Eng. Chem. Res. 2012, 51, 14824.

(25) El Osta, R.; Carlin-Sinclair, A.; Guillou, N.; Walton, R. I.; Vermoortele, F.; Maes, M.; de Vos, D.; Millange, F. Chem. Mater. 2012, 24, 2781.

(26) Vermoortele, F.; Maes, M.; Moghadam, P. Z.; Lennox, M. J.; Ragon, F.; Boulhout, M.; Biswas, S.; Laurier, K. G. M.; Beurroies, I.; Denoyel, R.; Roeffaers, M.; Stock, N.; Düren, T.; Serre, C.; De Vos, D. E. J. Am. Chem. Soc. 2011, 133, 18526.

(27) Torres-Knoop, A.; Krishna, R.; Dubbeldam, D. Angew. Chem., Int. Ed. 2014, 53, 7774.

(28) Warren, J. E.; Perkins, C. G.; Jelfs, K. E.; Boldrin, P.; Chater, P. A.; Miller, G. J.; Manning, T. D.; Briggs, M. E.; Stylianou, K. C.; Claridge, J. B.; Rosseinsky, M. J. Angew. Chem., Int. Ed. 2014, 53, 4592.

(29) (a) Bender. M. L.; Komiyama, M. Cyclodextrin Chemistry; Springer-Verlag: New York, 1978. (b) Tamaki, T.; Kokubu, T. J. Incl. Phenom. Macrocycl. Chem. 1984, 2, 815. (c) Harada, A.; Li, J.; Kamachi, M. Macromolecules 1993, 26, 5267. (d) Harada, A.; Li, J.; Kamachi, M. Nature 1994, 370, 126. (e) Li, G.; McGown, L. B. Science 1994, 264, 249. (f) Wenz, G. Angew. Chem., Int. Ed. Engl. 1994, 33, 803. (g) Vajda, S.; Jimenez, R.; Rosenthal, S. J.; Fidler, V.; Fleming, G. R.; Castner, E. W. J. Chem. Soc., Faraday Trans. 1995, 91, 867. (h) Rekharsky, M. V.; Inoue, Y. Chem. Rev. 1998, 98, 1875. (i) Takei, M.; Yui, H.; Hirose, Y.; Sawada, T. J. Phys. Chem. A 2001, 105, 11395. (j) Douhal, A. Chem. Rev. 2004, 104, 1955. (k) Ikeda, H.; Nihei, T.; Ueno, A. J. Org. Chem. 2005, 70, 1237. (l) Wenz, G.; Han, B.-H.; Muller, A. Chem. Rev. 2006, 106, 782. (m) Sallas, F.; Darcy, R. Eur. J. Org. Chem. 2008, 957. (n) Harada, A.; Takashima, Y.; Yamaguchi, H. Chem. Soc. Rev. 2009, 38, 875. (o) van de Manakker, F.; Vermonden, T.; van Nostrum, C. F.; Hennink, W. E. Biomacromolecules 2009, 10, 3157. (p) Schneider, H.-J. Angew. Chem., Int. Ed. 2009, 48, 3924. (q) Ke, C.; Yang, C.; Mori, T.; Wada, T.; Liu, Y.; Inoue, Y. Angew. Chem., Int. Ed. 2009, 48, 6675. (p) Chen, Y.; Liu, Y. Chem. Soc. Rev. 2010, 39, 495. (r) Harada, A.;

Kobayashi, R.; Takashima, Y.; Hashidzume, A.; Yamaguchi, H. Nat. Chem. 2011, 3, 34. (s) Nakahata, M.; Takashima, Y.; Yamaguchi, H.; Harada, A. Nat. Commun. 2011, 2, 511. (t) Wang, H. M.; Wenz, G. Chem. Asian J. 2011, 6, 2390. (u) Nalluri, S. K. M.; Voskuhl, J.; Bultema, J. B.; Boekema, E. J.; Ravoo, B. J. Angew. Chem., Int. Ed. 2011, 50, 9747. (v) Wang, H. M.; Wenz, G. Beilstein J. Org. Chem. 2012, 8, 1644. (w) Harada, A.; Takashima, Y. Chem. Res. 2013, 13, 420. (x) Schmidt, B. V. K. J.; Hetzer, M.; Ritter, H.; Barner-Kowollik, C. Prog. Polym. Sci. 2014, 39, 235. (y) Ma, X.; Tian, H. Acc. Chem. Res. 2014, 47, 1971. (y) Harada, A.; Takashima, Y.; Nakahata, M. Acc. Chem. Res. 2014, 47, 2128. (aa) Yang, C.; Inoue, Y. Chem. Soc. Rev. 2014, 43, 4123.

(30) Smaldone, R. A.; Forgan, R. S.; Furukawa, H.; Gassensmith, J. J.; Slawin, A. M. Z.; Yaghi, 0. M.; Stoddart, J. F. Angew. Chem., Int. Ed. 2010, 49, 8630.

(31) Forgan, R. S.; Smaldone, R. A.; Gassensmith, J. J.; Furukawa, H.; Cordes, D. B.; Li, Q.; Wilmer, C. E.; Botros, Y. Y.; Snurr, R. Q.; Slawin, A. M. Z.; Stoddart, J. F. J. Am. Chem. Soc. 2011, 134, 406.

(32) Furukawa, Y.; Ishiwata, T.; Sugikawa, K.; Kokado, K.; Sada, K. Angew. Chem., Int. Ed. 2012, 51, 10566.

(33) (a) Cole, J. H.; Everett, D. H.; Marshall, C. T.; Paniego, A. R.; Powl, J. C.; Rodriguez-Reinoso, F. J. Chem. Soc., Faraday Trans. 1974, 70, 2154. (b) Reid, C. R.; Thomas, K. M. J. Phys. Chem. B 2001, 105, 10619. (c) Bell, J. G.; Zhao, X.; Uygur, Y.; Thomas, K. M. J. Phys. Chem. C 2011, 115, 2776. (d) Crank, J. The mathematics of diffusion, 2nd ed.; Clarendon Press: Oxford, 1975. (e) Glueckauf, E.; Coates, J. I. J. Chem. Soc. 1947, 1315. (f) Glueckauf, E. Trans. Faraday Soc. 1955, 51, 1540. (g) Loughlin, K. F.; Hassan, M. M.; Fatehi, A. I.; Zahur, M. Gas Sep. Purif. 1993, 7, 264. (h) Webster, C. E.; Drago, R. S.; Zerner, M. C. J. Am. Chem. Soc. 1998, 120, 5509. (i) Li, L. J.; Bell, J. G.; Tang, S. F.; Lv, X. X.; Wang, C.; Xing, Y. L.; Zhao, X. B.; Thomas, K. M. Chem. Mater. 2014, 26, 4679. (j) Wang, C.; Li, L.; Bell, J. G.; Lv, X. X.; Tang, S.; Zhao, X. B.; Thomas, K. M. Chem. Mater. 2015, 27, 1502.

(34) Lucena, S. M. P.; Snurr, R. Q.; Cavalcante, C. L., Jr. Adsorption 2007, 13, 477.

Holcroft, J. M. et al. "Carbohydrate-Mediated Purification of Petrochemicals," J. Am. Chem. Soc. 2015, 137:5706-5719 (including Supporting Information).

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A method of separating an aromatic compound from a mixture of hydrocarbons, comprising:
providing a separation medium consisting of a crystalline cyclodextrin metal-organic framework (CD-MOF) that is made according to a synthetic method consisting of the following steps (i) and (ii):
(i) preparing a first mixture comprising a cyclodextrin, an alkali metal salt, water, and an alcohol; and
(ii) stirring the first mixture and subsequently crystallizing the CD-MOF from the first mixture or adding an amount of a surfactant to the first mixture to form a second mixture and subsequently crystallizing the CD-MOF from the second mixture to produce the crystalline CD-MOF,
wherein the crystalline CD-MOF has a particle size in the range of from about 1 micron to about 25 microns,
contacting the mixture of hydrocarbons with the separation medium;
resolving the aromatic compound from the mixture of hydrocarbons; and
isolating the aromatic compound from the mixture of hydrocarbons.

2. The method of claim 1, wherein the aromatic compound is an alkylaromatic compound or a haloaromatic compound.

3. The method of claim 1, wherein the aromatic compound is an alkylaromatic compound.

4. The method of claim 3, wherein the alkylaromatic compound is selected from the group consisting of toluene, ethylbenzene, ortho-xylene, meta-xylene, para-xylene, styrene, α-methylstyrene, cumene, ethyltoluene, 2-methylstyrene, 3-methylstyrene, 4-methylstyrene, and a combination thereof.

5. The method of claim 1, wherein the aromatic compound is a haloaromatic compound.

6. The method of claim 5, wherein the haloaromatic compound is selected from the group consisting of fluorobenzene, chlorobenzene, bromobenzene, iodobenzene, 1,2-dibromobenzene, 1,3-dibromobenzene, 1,4-dibromobenzene, 1-bromo-2-iodobenzene, 1-bromo-3-iodobenzene, 1-bromo-4-iodobenzene, 1,2-diiodobenzene, 1,2-dichlorobenzene, α,α,α-trifluorotoluene, and a combination thereof.

7. The method of claim 1, wherein the resolving the aromatic compound from the mixture of hydrocarbons comprises using a liquid chromatography mobile phase.

8. The method of claim 7, wherein the liquid chromatography mobile phase comprises at least one compound selected from the group consisting of hexane, methylene chloride, methanol, and 2-propanol.

9. The method of claim 7, wherein the separation medium is disposed in a chromatography column.

10. The method of claim 9, wherein the chromatography column is configured for high performance liquid chromatography.

11. The method of claim 1, wherein the resolving the aromatic compound from the mixture of hydrocarbons comprises using a gas phase.

12. The method of claim 1, wherein the crystalline CD-MOF has a particle size selected from the group consisting of: a particle size in the range of from about 1 micron to about 10 microns; a particle size in the range of from about 5 microns to about 15 microns; a particle size in the range of from about 10 microns to about 15 microns; and a particle size of about 25 microns.

13. The method of claim 1, wherein the crystalline CD-MOF has a particle size in the range of from about 10 microns to about 15 microns.

* * * * *